US012643891B2

(12) United States Patent
Rinehart et al.

(10) Patent No.: US 12,643,891 B2
(45) Date of Patent: Jun. 2, 2026

(54) SPAK/OSR INHIBITORS AND METHODS OF USING SAME

(71) Applicants: YALE UNIVERSITY, New Haven, CT (US); MAYO FOUNDATION FOR MEDICAL EDUCATION AND RESEARCH, Rochester, MN (US)

(72) Inventors: Jesse Rinehart, Guilford, CT (US); Farren Isaacs, Stamford, CT (US); Andre Levchenko, Madison, CT (US); Denton Hoyer, West Haven, CT (US); Apiwat Wangweerawong, Bedford, MA (US); William Hungerford, Kenneth City, FL (US); Mark Plummer, Westbrook, CT (US); Alfredo Quinones-Hinojosa, Ponte Vedra Beach, FL (US); Paula Valentina Schiapparelli, Ponte Vedra Beach, FL (US)

(73) Assignee: Yale University, New Haven, CT (US)

( * ) Notice: Subject to any disclaimer, the term of this patent is extended or adjusted under 35 U.S.C. 154(b) by 650 days.

(21) Appl. No.: 17/756,890

(22) PCT Filed: Dec. 4, 2020

(86) PCT No.: PCT/US2020/063382

§ 371 (c)(1),
(2) Date: Jun. 3, 2022

(87) PCT Pub. No.: WO2021/113689

PCT Pub. Date: Jun. 10, 2021

(65) Prior Publication Data

US 2023/0227439 A1 Jul. 20, 2023

Related U.S. Application Data

(60) Provisional application No. 62/944,839, filed on Dec. 6, 2019.

(51) Int. Cl.

| | |
|---|---|
| ***C07D 413/12*** | (2006.01) |
| ***A61K 45/06*** | (2006.01) |
| ***A61P 35/00*** | (2006.01) |
| ***C07D 239/48*** | (2006.01) |
| ***C07D 403/12*** | (2006.01) |

(52) U.S. Cl.

CPC ............ *C07D 413/12* (2013.01); *A61K 45/06* (2013.01); *A61P 35/00* (2018.01); *C07D 239/48* (2013.01); *C07D 403/12* (2013.01)

(58) Field of Classification Search

CPC .. C07D 413/12; C07D 239/48; C07D 403/12; A61K 45/06; A61P 35/00

See application file for complete search history.

(56) References Cited

U.S. PATENT DOCUMENTS

| | | | | |
|---|---|---|---|---|
| 7,521,457 B2 * | 4/2009 | Stadtmueller | A61P 37/06 544/323 |
| 8,148,391 B2 * | 4/2012 | Ahmed | C07D 239/48 514/275 |
| 2003/0082720 A1 | 5/2003 | Lifton | |

FOREIGN PATENT DOCUMENTS

| | | | |
|---|---|---|---|
| WO | WO-2006021454 A2 * | 3/2006 | A61P 9/00 |
| WO | WO-2008092049 A1 * | 7/2008 | A61P 35/04 |
| WO | 2014058921 | 4/2014 | |
| WO | WO-2014058921 A2 * | 4/2014 | A61P 35/00 |
| WO | 2016033100 | 3/2016 | |
| WO | WO-2016033100 A1 * | 3/2016 | A61P 9/10 |

OTHER PUBLICATIONS

Halder, et al.; Cancer Research, v67, pp. 10976-10983 (2007). (Year: 2007).*
Ward, et al.; Journal of Medicinal Chemistry, v56, pp. 7025-7048—Supporting Information (2013). (Year: 2013).*
Ward, et al.; Journal of Medicinal Chemistry, v56, pp. 7025-7048 (2013). (Year: 2013).*
Barreiro, et al., Chemical Reviews, v111, pp. 5215-5246; 2011 (Year: 2011).*
Patani, G. A., LaVoie, E. J .; Chemical Reviews, v96, pp. 3147-3176; 1996 (Year: 1996).*
Brown; Bioisosteres in Medicinal Chemistry, Wiley-VCH, 2012 (Year: 2012).*
Eriko, et al.; Journal of the American Society of Nephrology, v26, pp. 1525-1536; 2015 (Year: 2015).*
Lietha, et al.; PLoS One, v3(11), pp. 1-7; 2008 (Year: 2008).*
Milkiewicz, et al.; Expert Opinion on Therapeutic Patents, v20, pp. 1653-1681; 2010 (Year: 2010).*
Roskoski Jr., R.; Pharmacological Research, v100, pp. 1-23; 2015 (Year: 2015).*
Yang, et al.; European Journal of Medicinal Chemistry, v56, pp. 30-38; 2012 (Year: 2012).*
Barber, Karl W., and Jesse Rinehart. “The abcs of ptms.” Nature chemical biology 14.3 (2018): 188-192.
Cuddapah, V. A., and H. Sontheimer. “Ion channels and transporters in cancer. 2. Ion channels and the control of cancer cell migration (vol. 301, p. C541, 2011).” American Journal of Physiology-Cell Physiology 301.6 (2011): C1479-C1479.

(Continued)

*Primary Examiner* — Jeffrey S Lundgren
*Assistant Examiner* — W. Justin Youngblood
(74) *Attorney, Agent, or Firm* — Saul Ewing LLP; Domingos J. Silva; Kathryn Doyle

(57) ABSTRACT

The present disclosure provides SPAK/OSR inhibitors. In certain embodiments, the compounds of the disclosure can be used to treat, ameliorate, and/or prevent certain cancers in a subject.

20 Claims, 48 Drawing Sheets

Specification includes a Sequence Listing.

(56) References Cited

OTHER PUBLICATIONS

Cuddapah, Vishnu Anand, and Harald Sontheimer. "Ion channels and transporters [corrected] in cancer. 2. Ion channels and the control of cancer cell migration." American journal of physiology. Cell physiology 301.3 (2011): C541-9.
Delpire, Eric, and Kenneth BE Gagnon. "SPAK and OSR1: STE20 kinases involved in the regulation of ion homeostasis and volume control in mammalian cells." Biochemical Journal 409.2 (2008): 321-331.
Dowd, Brian FX, and Biff Forbush. "PASK (proline-alanine-rich STE20-related kinase), a regulatory kinase of the Na—K—CI cotransporter (NKCC1)." Journal of Biological Chemistry 278.30 (2003): 27347-27353.
Doyle, Andrew D., et al. "One-dimensional topography underlies three-dimensional fibrillar cell migration." Journal of cell biology 184.4 (2009): 481-490.
Dranchak, Patricia, et al. "Profile of the GSK published protein kinase inhibitor set across ATP-dependent and- independent luciferases: implications for reporter-gene assays." PloS one 8.3 (2013): e57888.
Filippi, Beatrice M., et al. "MO25 is a master regulator of SPAK/OSR1 and MST3/MST4/YSK1 protein kinases." The EMBO journal 30.9 (2011): 1730-1741.
Flemmer, Andreas W., et al. "Activation of the Na—K—CI cotransporter NKCC1 detected with a phospho-specific antibody." Journal of Biological Chemistry 277.40 (2002): 37551-37558.
Galli, Rossella, et al. "Isolation and characterization of tumorigenic, stem-like neural precursors from human glioblastoma." Cancer research 64.19 (2004): 7011-7021.
Garzon-Muvdi, Tomas, et al. "Regulation of brain tumor dispersal by NKCC1 through a novel role in focal adhesion regulation." PLoS biology 10.5 (2012): e1001320.
Giménez, Ignacio. "Molecular mechanisms and regulation of furosemide-sensitive Na—K—Cl cotransporters." Current opinion in nephrology and hypertension 15.5 (2006): 517-523.
Grimm, P. Richard, et al. "SPAK isoforms and OSR1 regulate sodium-chloride co-transporters in a nephron-specific manner." Journal of Biological Chemistry 287.45 (2012): 37673-37690.
Haas, Brian R., and Harald Sontheimer. "Inhibition of the sodium-potassium-chloride cotransporter isoform-1 reduces glioma invasion." Cancer research 70.13 (2010): 5597-5606.
Huberfeld, Gilles, and Charles J. Vecht. "Seizures and gliomas—towards a single therapeutic approach." Nature Reviews Neurology 12.4 (2016): 204-216.
Hutti, Jessica E., et al. "A rapid method for determining protein kinase phosphorylation specificity." Nature methods 1.1 (2004): 27-29.
International Search Report and Written Opinion issued in App. No. PCT/US2020/063382, mailing date Mar. 24, 2021, 12 pages.
Isaacs, Farren J., et al. "Precise manipulation of chromosomes in vivo enables genome-wide codon replacement." Science 333.6040 (2011): 348-353.
Kim, Tae Kyung, and James H. Eberwine. "Mammalian cell transfection: the present and the future." Analytical and bioanalytical chemistry 397 (2010): 3173-3178.
Lajoie, Marc J., et al. "Genomically recoded organisms expand biological functions." science 342.6156 (2013): 357-360.
Miller, Martin Lee, et al. "Linear motif atlas for phosphorylation-dependent signaling." Science signaling 1.35 (2008): ra2-ra2.
Moriguchi, Tetsuo, et al. "WNK1 regulates phosphorylation of cation-chloride-coupled cotransporters via the STE20-related kinases, SPAK and OSR1." Journal of Biological Chemistry 280.52 (2005): 42685-42693.
Naguro, Isao, et al. "ASK3 responds to osmotic stress and regulates blood pressure by suppressing WNK1-SPAK/OSR1 signaling in the kidney." Nature communications 3.1 (2012): 1285.
Park, Hee-Sung, et al. "Expanding the genetic code of *Escherichia coli* with phosphoserine." Science 333.6046 (2011): 1151-1154.
Piechotta, K., and E. Delpire. "Characterization of the interaction between cation-chloride cotransporters and tire stress-activated serine-threonine-kinases SPAK and OSR1." FASEB Journal. vol. 16. No. 4. 9650 Rockville Pike, Bethesda, MD 20814-3998 USA: Federation Amer Soc Exp Biol, 2002.
Pirman, Natasha L., et al. "A flexible codon in genomically recoded *Escherichia coli* permits programmable protein phosphorylation." Nature communications 6.1 (2015): 8130.
Rafiqi, Fatema H., et al. "Role of the WNK-activated SPAK kinase in regulating blood pressure." EMBO molecular medicine 2.2 (2010): 63-75.
Rinehart, Jesse, et al. "Sites of regulated phosphorylation that control K—Cl cotransporter activity." Cell 138.3 (2009): 525-536.
Schiapparelli, Paula, et al. "NKCC1 regulates migration ability of glioblastoma cells by modulation of actin dynamics and interacting with cofilin." EBioMedicine 21 (2017): 94-103.
Smith, Chris L., et al. "Migration phenotype of brain-cancer cells predicts patient outcomes." Cell reports 15.12 (2016): 2616-2624.
Szewczuk, Lawrence M., Mary Katherine Tarrant, and Philip A. Cole. "Protein phosphorylation by semisynthesis: from paper to practice." Methods in enzymology 462 (2009): 1-24.
Thastrup, Jacob O., et al. "SPAK/OSR1 regulate NKCC1 and WNK activity: analysis of WNK isoform interactions and activation by T-loop trans-autophosphorylation." Biochemical Journal 441.1 (2012): 325-337.
Vitari, Alberto C., et al. "Functional interactions of the SPAK/OSR1 kinases with their upstream activator WNK1 and downstream substrate NKCC1." Biochemical Journal 397.1 (2006): 223-231.
Vitari, Alberto C., et al. "The WNK1 and WNK4 protein kinases that are mutated in Gordon's hypertension syndrome phosphorylate and activate SPAK and OSR1 protein kinases." Biochemical Journal 391.1 (2005): 17-24.
Wang, Zhaohong, Chao-Ling Yang, and David H. Ellison. "Comparison of WNK4 and WNK1 kinase and inhibiting activities." Biochemical and biophysical research communications 317.3 (2004): 939-944.
Wilson, Frederick H., et al. "Human hypertension caused by mutations in WNK kinases." Science 293.5532 (2001): 1107-1112.
Zagórska, Anna, et al. "Regulation of activity and localization of the WNK1 protein kinase by hyperosmotic stress." The Journal of cell biology 176.1 (2007): 89-100.

* cited by examiner

SPAK Targets

| | | | |
|---|---|---|---|
| mNCC | 55 | LYMRTF...GYNTIDV | SEQ ID NO:8; SEQ ID NO:9 |
| hNCC | 57 | FCMRTF...GYNTIDV | SEQ ID NO:10 |
| mNKCC1 | 208 | YYLRTF...GHNTMDA | SEQ ID NO:11, SEQ ID NO:12 |
| hNKCC1 | 214 | YYLRTF...GHNTMDA | |
| mNKCC2 | 98 | YYLQTF...GHNTMDA | SEQ ID NO:13 |
| hNKCC2 | 102 | YYLQTF...GHNTMDA | |
| hKCC3 | 987 | TYERTL...VHMTWTK | SEQ ID NO:14; SEQ ID NO:15 |
| mKCC3 | 987 | TYERTL...VHMTWTK | |
| hKCC2 | 902 | TYEKTL...VHLTWTK | SEQ ID NO:16 |
| mKCC2 | 902 | TYEKTL...VHLTWTK | |
| hKCC1 | 922 | TYERTL...IQMTWTR | SEQ ID NO:17 |
| mKCC1 | 922 | TYERTL...IQMTWTR | |

Inh. A, Inh. B
(7a)

(7a)
Inh. A/B (7b)

FIG. 18A

| Gene | Yale Reference Number | Antibiotic | Primers | Cloning Strategy | Restriction Sites |
|---|---|---|---|---|---|
| WT WNK1 (1-661) | B18 | AMP | N/A | N/A | |
| WT WNK1 (1-483) | B43 | AMP | For 5′-<br>ACCCCAGAGTTCATGGCCCC (SEQ ID NO: 24)<br>Rev 5′- CCGCTCGAGTTATGTTTCCTCTTGGAAGAAGG<br>(SEQ ID NO: 25) | PCR amplification from B18 | SphI-XhoI |
| $1S^P$ WNK1 (1-661) | B34 | AMP | For 5′-<br>GGGCTTCTTTTGCCAAGTAGGTGATAGGTACCCCAG<br>Rev 5′-<br>CTGGGGTACCTATCACCTACTTGGCAAAAGAAGCCC<br>FOR: SEQ ID NO: 26<br>REV: SEQ ID NO: 27 | Mutagenesis from B18 | |
| $1S^P$ WNK1 (1-483) | B44 | AMP | For 5′-<br>ACCCCAGAGTTCATGGCCCC<br>Rev 5′- CCGCTCGAGTTATGTTTCCTCTTGGAAGAAGG | PCR amplification from B34 | SphI-XhoI |
| $2S^P$ WNK1 (1-661) | B42 | AMP | For 5′-<br>CCTGAAGCGGGCTTAGTTTGCCAAGTAGGTG<br>Rev 5′-<br>CACCTACTTGGCAAACTAAGCCCGCTTCAGG | Mutagenesis from B34 | |
| | | | FOR: SEQ ID NO: 28<br>REV: SEQ ID NO: 29 | | |
| $2S^P$ WNK1 (1-483) | B45 | AMP | For 5′-<br>ACCCCAGAGTTCATGGCCCC<br>Rev 5′- CCGCTCGAGTTATGTTTCCTCTTGGAAGAAGG | PCR amplification from B42 | SphI-XhoI |

FIG. 18B

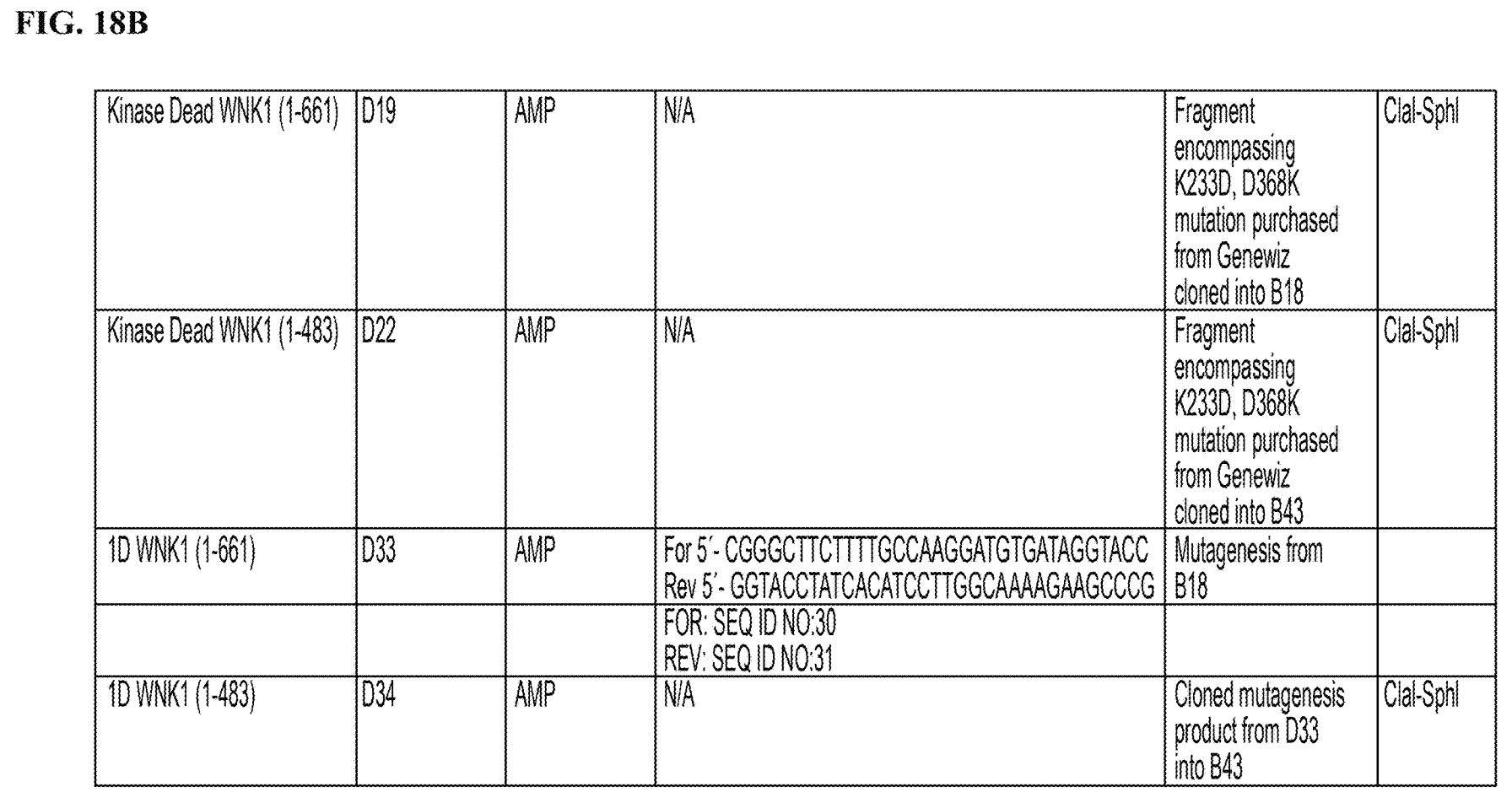

| | | | | | |
|---|---|---|---|---|---|
| Kinase Dead WNK1 (1-661) | D19 | AMP | N/A | Fragment encompassing K233D, D368K mutation purchased from Genewiz cloned into B18 | ClaI-SphI |
| Kinase Dead WNK1 (1-483) | D22 | AMP | N/A | Fragment encompassing K233D, D368K mutation purchased from Genewiz cloned into B43 | ClaI-SphI |
| 1D WNK1 (1-661) | D33 | AMP | For 5′- CGGGCTTCTTTTGCCAAGGATGTGATAGGTACC<br>Rev 5′- GGTACCTATCACATCCTTGGCAAAAGAAGCCCG | Mutagenesis from B18 | |
| | | | FOR: SEQ ID NO:30<br>REV: SEQ ID NO:31 | | |
| 1D WNK1 (1-483) | D34 | AMP | N/A | Cloned mutagenesis product from D33 into B43 | ClaI-SphI |

FIG. 18C

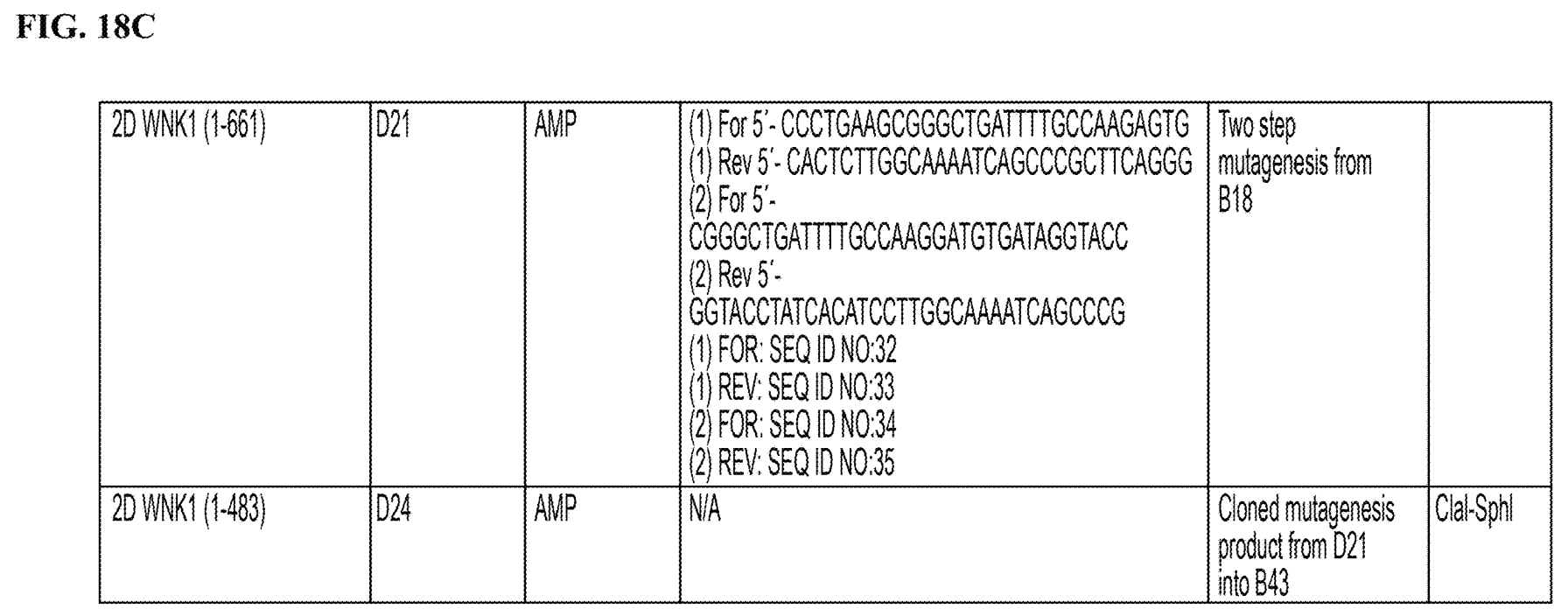

| | | | | | |
|---|---|---|---|---|---|
| 2D WNK1 (1-661) | D21 | AMP | (1) For 5′- CCCTGAAGCGGGCTGATTTTGCCAAGAGTG<br>(1) Rev 5′- CACTCTTGGCAAAATCAGCCCGCTTCAGGG<br>(2) For 5′-<br>CGGGCTGATTTTGCCAAGGATGTGATAGGTACC<br>(2) Rev 5′-<br>GGTACCTATCACATCCTTGGCAAAATCAGCCCG<br>(1) FOR: SEQ ID NO:32<br>(1) REV: SEQ ID NO:33<br>(2) FOR: SEQ ID NO:34<br>(2) REV: SEQ ID NO:35 | Two step mutagenesis from B18 | |
| 2D WNK1 (1-483) | D24 | AMP | N/A | Cloned mutagenesis product from D21 into B43 | ClaI-SphI |

(6b)

Viability of GBM Cell lines

(6a) dose response

| | QNS 120 | 965 | 612 | QNS108 | GBM1A |
|---|---|---|---|---|---|
| [Inhibitor] vs. normalized response -- Variable slope | | | | | |
| Best-fit values | | | | | |
| IC50 | 0.7640 | 8.654 | 3.443 | 15.72 | 0.4308 |
| HillSlope | -0.3113 | -4.133 | -0.4243 | -0.8064 | -0.6490 |
| logIC50 | -0.1169 | 0.9372 | 0.5369 | 1.197 | -0.3656 |
| 95% CI (profile likelihood) | | | | | |
| IC50 | 0.5950 to 0.9701 | 7.401 to 9.763 | 2.717 to 4.347 | 13.05 to 18.75 | 0.3709 to 0.5004 |
| HillSlope | -0.3408 to -0.2832 | -7.937 to -3.007 | -0.4690 to -0.3829 | -0.9626 to -0.6824 | -0.7068 to -0.5968 |
| logIC50 | -0.2255 to -0.01320 | 0.8693 to 0.9896 | 0.4341 to 0.6382 | 1.116 to 1.273 | -0.4307 to -0.3007 |
| Goodness of Fit | | | | | |
| Degrees of Freedom | 51 | 52 | 52 | 52 | 52 |
| R squared | 0.9251 | 0.9496 | 0.9293 | 0.9342 | 0.9695 |
| Sum of Squares | 1503 | 5812 | 2564 | 3671 | 1467 |
| Sy.x | 5.429 | 10.57 | 7.022 | 8.402 | 5.311 |

Subcutaneous tumor
IP administration

Low-dose (6a)
(0.05 mg/kg daily injections)

Annexin V-PI

SPAK/OSR INHIBITORS AND METHODS OF USING SAME

CROSS-REFERENCE TO RELATED APPLICATIONS

The present application is a 35 U.S.C. § 371 national stage application from, and claims priority to, International Application No. PCT/US2020/063382, which claims priority under 35 U.S.C. § 119(e) to U.S. Provisional Application No. 62/944,839, filed Dec. 6, 2019, the contents of which are incorporated herein by reference in their entireties.

STATEMENT REGARDING FEDERALLY SPONSORED RESEARCH

This invention was made with government support under NS070024 and CA209992 awarded by National Institutes of Health. The government has certain rights in the invention.

BACKGROUND

Many of the protein signaling networks that are critical for the emergence and progression of cancers are difficult to target due to incomplete biochemical characterization of their regulatory mechanisms. Among the numerous knowledge gaps is the role of post-translational modification, and barriers to their biochemical synthesis is a major road-block. Recently, synthetic and chemical biology based tools have provided exciting new solutions for post-translational modifications that were seemingly biochemically intractable. Several signaling pathways have been directly implicated in mechanisms of cell migration, of which, cell volume control has been recognized as an essential component.

The family of WNK (With-No-Lysine (K)) kinases and SPAK/OSR1 (STE20/SPS1-related proline/alanine-rich kinase/oxidative stress response) kinases play a key role in the maintenance of cell volume by controlling the phosphorylation of ion co-transporters, particularly NKCC1 ($Na^+$—$K^+$—$Cl^-$ co-transporter 1). Glioblastoma multiforme (GBM), one of the most invasive and aggressive human cancers, manipulates cellular volume through alterations in the activity of ion co-transporters to facilitate migration through the extracellular matrix. In GBM, higher SPAK expression levels and/or higher OSR expression levels lead to decreased patient survival. Together, these observations suggest that inhibition of kinases in the WNK-SPAK regulatory network and subsequent reduction in ion co-transporter activity may provide an effective strategy to prevent infiltration of GBM cells. Given that the effective treatment of GBM will require new compounds and therapeutic innovations, bringing new synthetic biology-based strategies to target the WNK-SPAK kinase network is particularly compelling.

Small molecule inhibitors are essential tool compounds for drug target validation, mechanistic exploration, and inevitably serve as potential leads in discovery of clinical inhibitors. The barrier to identification of tool compounds is the capacity to conduct screens, as screens require active kinase. While bacterial over-expression systems are a gold standard for protein production, there are barriers to expression of active, post-translationally modified human kinases. Heterologous systems typically lack the signaling proteins or physiological context required to activate kinases. Often the precise mechanisms of kinase activation, mostly via phosphorylation, are poorly understood and further limit heterologous production. Acidic amino acid substitutions of aspartate or glutamate for phosphoserine, for example, often fail to recapitulate biological activity. One can enable the heterologous expression of authentically phosphorylated proteins by using a genomically recoded strain of *E. coli* (Isaacs, et al., 2011, Science 333:348-353; Lajoie, et al., 2013, Science 342:357-360) paired with a phosphoserine orthogonal translation system (pSerOTS) (Park, et al., 2011, Science 333:1151-1154; Pirman et al., 2015, Nature communications 6:8130). The pSerOTS uses a phosphoseryl-tRNA synthetase (pSerRS) to aminoacylate pSer onto a UAG-decoding $tRNA^{pSer}$ and an engineered elongation factor Tu (EF-pSer) to deliver pSer84 $tRNA^{pSer}$ to the ribosome, thus permitting recombinant expression of proteins with site-specific authentic phosphorylation (FIG. 1A).

Although the role of WNK1 in activating SPAK to modulate ion-co-transporters has been established, the upstream activators of WNK1 remain unknown. In addition, an inability to access and produce high yields of physiologically phosphorylated WNK and SPAK/OSR1 has hindered direct investigation of the underlying mechanisms.

There still remains a need in the art for small molecule inhibitors of SPAK activity. In certain embodiments, such inhibitors can be used for treating, ameliorating, and/or preventing cancer cell migration and/or metastasis. The present disclosure satisfies this need in the art.

BRIEF SUMMARY OF THE DISCLOSURE

The present disclosure provides a compound of formula (I), or a salt, solvate, isotopically labelled derivative, stereoisomer, tautomer, or geometric isomer thereof:

(I)

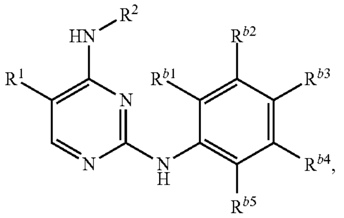

wherein $R^1$, $R^2$, $R^{b1}$, $R^{b2}$, $R^{b3}$, $R^{b4}$, and $R^{b5}$ are described elsewhere herein. The present disclosure further provides a method of preparing a compound of the disclosure. The present disclosure further provides a pharmaceutical composition comprising at least one pharmaceutically acceptable excipient and a compound of the disclosure.

The present disclosure provides a method of inhibiting SPAK and/or OSR activity in a subject, the method comprising administering to the subject a therapeutically effective amount of a compound of the disclosure. The present disclosure further provides a method of treating, ameliorating, and/or preventing cancer in a subject, the method comprising administering to the subject a therapeutically effective amount of a compound of the disclosure. The present disclosure further provides a method of treating, ameliorating, and/or preventing cancer cell migration and/or invasion in a subject, the method comprising administering to the subject a therapeutically effective amount of a compound of the disclosure. The present disclosure further provides a method of reducing or reversing growth and/or viability of a cancer in a subject, the method comprising administering to the subject a therapeutically effective amount of a compound of the disclosure. The present disclosure further provides a method of reducing volume of a cancerous tumor in a subject, the method comprising administering to the subject a therapeutically effective amount of a compound of the disclosure. The present disclosure further provides a method of extending survival in a subject afflicted with a cancer, the method comprising administering to the subject a therapeutically effective amount of a compound of the disclosure.

BRIEF DESCRIPTION OF THE DRAWINGS

The following detailed description of exemplary embodiments of the disclosure will be better understood when read in conjunction with the appended drawings. For the purpose of illustrating the disclosure, non-limiting embodiments are shown in the drawings. It should be understood, however, that the disclosure is not limited to the precise arrangements and instrumentalities of the embodiments shown in the drawings.

FIG. 1A: Phosphoserine technology. (Top) SepRS charges phosphoserine onto $tRNA^{pSer}$, which directs phosphoserine incorporation at UAG stop codons. Human phosphoprotein can be produced in *E. coli* by placing TAG at any position in the recombinant DNA. (Bottom) Depiction of genetically encoded phosphoserine in WNK1 yielding physiologically phospho-activated SPAK and subsequent phosphorylation of NKCC1 on its physiologically relevant sites. FIG. 1B: Schematic representation of WNK1 and SPAK displaying the domains used in this study. The T643 loop phosphorylation sites for each protein are highlighted in red. FIG. 1C: WNK1 variants containing (1-661) or lacking (1-483) the autoinhibitory domain (AID) were expressed in EcAR7 containing the Sep-OTS. The key active site residues S382 ($1S^P$), and S378/S382 ($2S^P$) of WNK1 were mutated to TAG for Sep incorporation. WT SPAK was expressed alone, or co-expressed with the $S382S^P$ WNK1 variant (denoted in red). Samples were purified using GST-affinity chromatography and eluted with GST649 prescission protease. Phosphoserine incorporation at residue S382 in WNK1 was confirmed by immunoblotting with a phosphospecific antibody. FIG. 1D: Identified SPAK kinase motif sequence logo representing the amino acid preferences at different positions relative to the phosphorylation site. FIG. 1E: Sequence alignment of ion co-transporters regulated by phosphorylation at the highlighted red T. Residues highlighted in grey are conserved residues throughout the co-transporters that were shown to have high amino acid preference at that given position from the phosphorylation site in the motif analysis. FIG. 1F: Analysis of WNK1 and SPAK kinase activity. WNK1 variants and SPAK either singly (black) or co-expressed (red) were reacted in vitro with NKCC1 substrate. Kinase activity was monitored by immunoblotting with phosphospecific antibody recognizing phosphorylated NKCC1, TPNKCC1. Immunoblotting with Streptactin was used to verify equal loading of the strep-tagged NKCC1 substrate. Immunoblotting with Anti-SPAK, and WNK1 SP382 was used to show enzyme loading in each reaction. This data revealed that only co-expressed Sep-activated WNK1/WT SPAK samples were able to phosphorylate the NKCC1 substrate.

FIG. 2A: 320 compounds from the GSK published inhibitor set (PKISI) were evaluated in a preliminary in vitro ELISA screen, where reduction in NKCC1 phosphorylation was monitored by the phosphospecific antibody, $T^P$NKCC1. At least one lead compound was extracted from the screen with a reduction in NKCC1 phosphorylation at inhibitor concentrations of 27 μM compared to vehicle controls. FIG. 2B: Structures of a selected identified compound from the ELISA inhibitor screen. FIG. 2C: Dose dependent inhibition with Inh.A/Inh.B (7a) was further evaluated using both NKCC1 and KCC as substrates and immunoblotting with $T^P$NKCC1, and $T^P$KCC; respectively. FIG. 2D: mDCT15 cells were incubated with a lead inhibitor compound, and a reduction in NKCC1 phosphorylation from the cell lysates were monitored using the $T^P$NKCC1 antibody. Data shown is representative of duplicate experiments. FIG. 2E: mDCT15 cells were incubated with a serial dilution of (7a), and the reduction of NKCC1 phosphorylation as a function of inhibitor concentration from the cell lysates was monitored using the $T^P$NKCC1 antibody. Each experiment was performed in quadruplicate. The densitometry values were calculated using Bio-Rad Image Lab software and are plotted as mean±s.d. Replicate 4 was compromised and thus not included in the reported densitometry values. FIG. 2F: Co-expressed phospho-activated WNK4/SPAK and WNK1/OSR1 yield highly active kinase preparations and are inhibited by (7a). In vitro assessment of kinase activities and (7a) inhibition of the WNK1 and SPAK homologs (WNK4 and OSR1) evaluated via western blot.

FIG. 3A: Analysis of NKCC1 expression and activity in cultured GBM primary cell lines. NKCC1 expression and activity was monitored by immunoblotting with antibodies recognizing total NKCC1 and phosphorylated $T^P$NKCC1. SPAK expression was assessed using a SPAK specific antibody and immunoblot using GAPDH specific antibody was used as a loading control. FIG. 3B: Inhibitory effect of (7a) on primary GBM cell line 499. The phosphorylation states of NKCC1 and KCC was assessed by immunoblotting with $T^P$NKCC1 and $T^P$KCC specific antibodies, respectively. FIG. 3C: Schematic representation of migration assay employing a tissue-mimetic nanopatterned substrate coated with extracellular matrix components promoting brain cancer cell migration. FIG. 3D: Duplicate time course experiments of GB 499 cells incubated with 20 μM (7a), 40 μM (7a), or equivalent volume of DMSO vehicle for 1 hr, 2 hr, 3 hr. NKCC1 phosphorylation was monitored using the $T^P$NKCC1 antibody and compared to total NKCC1 and actin loading control. FIG. 3E: Histograms and box plots of distribution of number of cells with respect to average migration speed for GB 499 cells comparing cells treated with 20 μM or 40 μM (7a) and the equivalent vehicle control. FIG. 3F: Comparison of average migration speed over 10 hours of GB 499 cells treated with 20 μM or 40 μM (7a) compared to the equivalent DMSO vehicle control. FIG. 3G: Comparison of average migration speed over 10 hours of primary cell lines 499, 965, and GBM1A cells treated with 5 μM, 20 μM, or 40 μM (7a) compared to the equivalent DMSO vehicle control. Error bars represent standard error mean (SEM). Statistical significance was determined using a Wilcoxon rank-sum test (*$p<0.05$, $p<0.01$, *$p<0.001$).

FIG. 4A: Illustration of ion transporter mediated invasion of extracellular matrix. FIG. 4B: GBM1A cells were incubated with 20 μM (7a) or equivalent volume of DMSO vehicle for a 1 hr. After incubation the cells were imaged by confocal microscopy at 40× across the z-axis at increments of 0.28 microns. Cell volume was calculated using 3D reconstruction of the z-stack in ImageJ. FIG. 4C: Dose-dependent inhibition of GBM proliferation in multiple cell lines. FIG. 4D: Inhibition of GBM1A subcutaneous tumor growth in athymic nude mice (n=5 per group) in response to daily intraperitoneal injections of 0.1 mg/kg (7a).

FIG. 5A: NKCC1 phosphorylation with $^{32}P$ was monitored by autoradiography following in vitro kinase reactions with 1× and 10× WT, T233E SPAK±MO25α expressed alone or with WNK1 variants containing (1-661) or lacking (1-483) the auto inhibitory domain (AID). NKCC1 phosphorylation with $^{32}P$ was monitored by autoradiography following in vitro kinase reactions. FIG. 5B: Each sample was further analyzed by isolating the band corresponding to the NKCC1 substrate and quantifying $^{32}P$ incorporation by Cernekov counting. The reported concentration of $^{32}P$ incorporated is the average of duplicate experiments.

FIG. 8A: Illustration depicting assay conditions and observed result. FIG. 8B: SPAK kinase screen using the positional scanning peptide library (PSPL) bearing the denoted amino acid at defined positions relative to a central S/T phosphor-acceptor site.

FIG. 12A: Structures of (7a) and analog (7b). FIG. 12B: In vitro dose-dependent inhibition comparing (7a) and (7b) evaluated by western blot using $T^{P}$NKCC1. FIG. 12C: Western blot analysis of NKCC1 phospho-depletion in mDCT15 cells under various conditions. FIG. 12D: mDCT15 cells were incubated with 40 μM (7a), 40 μM Cabozantinib (XL-184), or equivalent volume of DMSO vehicle for 1 hr, 2 hr, 3 hr, and 4 hr. NKCC1 phosphorylation was monitored using the $T^{P}$NKCC1 antibody and compared to total NKCC1. FIG. 12E: HEK 293 induced to express KCC were incubated with 40 μM (7a), 40 μM Cabozantinib (XL-184), or equivalent volume of DMSO vehicle for 1 hr, and 2 hr time points. KCC phosphorylation was monitored using the $T^{P}$KCC antibody and compared to total KCC using C-Myc antibody. FIG. 12F: mDCT15 cells were incubated with 40 μM (7a), 40 μM Cabozantinib (XL-184), or equivalent volume of DMSO vehicle for a 1 hr, 2 hr, 3 hr, and 4 hr time course. After incubation the cells were imaged using 20× bright field microscopy. 1 hr and 4 hr time points are shown.

FIG. 14A: The phosphorylation states of NKCC1 and KCC was assessed by immunoblotting with $T^{P}$NKCC1 and $T^{P}$KCC specific antibodies, respectively. FIG. 14B: Comparison of average migration speed over 10 hours of GBM1A cells treated with 20 μM or 40 μM (7a) compared to the equivalent DMSO vehicle control. FIG. 14C: Histograms and box plots of distribution of number of cells with respect to average migration speed for GBM cell line GBM1A comparing treatment with 20 μM or 40 μM (7a) and the equivalent vehicle control. Error bars represent standard error mean (SEM). Statistical significance was determined using a Wilcoxon rank-sum test (*$p<0.05$, $p<0.01$, *$p<0.001$).

FIG. 15A: The phosphorylation states of NKCC1 and KCC was assessed by immunoblotting with $T^{P}$NKCC1 and $T^{P}$KCC specific antibodies, respectively. FIG. 15B: Comparison of average migration speed over 10 hours of GB 965 cells treated with 20 μM or 40 μM (7a) compared to the equivalent DMSO vehicle control. FIG. 15C: Histograms and box plots of distribution of number of cells with respect to average migration speed for GBM cell line 965 comparing treatment with 20 μM or 40 μM (7a) and the equivalent vehicle control. Error bars represent standard error mean (SEM). Statistical significance was determined using a Wilcoxon rank-sum test (*$p<0.05$, $p<0.01$, *$p<0.001$).

FIG. 18 illustrates primers for WNK1 constructs.

FIG. 22A: Western of (7a) and (6a) activity. FIG. 22B: Cell based assays validate (6a) and (7a) on target activity.

FIG. 22C: Primary human GBM cell based assays (GBM612) validate (6a) on target activity.

FIG. 22D: Human derived GBM cell based assays (GBM1A) validate (6a) on target activity.

FIG. 23A: Pathway expression analysis in primary human GBM cells.

FIG. 23B: Primary human GBM cell based assays (GBM612) validate (6a) on target activity.

FIG. 32A: Schematic of the human GMB intracranial xenograft. FIG. 32B: Tumor growth profiles at two (6a) doses.

FIG. 38A: Example cell cycle FACS data for 612 cells treated with 2 μM of (6a). FIG. 38B: Cell cycle analysis of GBM cell lines treated with 2 μM of (6a).

FIG. 40A: GBM cells were pretreated for 24 hs with 1 μM (6a) or vehicle control and irradiated. After 72 hs, cells were re-plated to study clonogenicity. 15 days after treatment clonogenic potential was the lowest in the combination treatment in vitro. FIG. 40B: Western blot shows decrease full length PARP-1 upon (6a) treatment after 24 hs. FIG. 40C: Expression of DNA damage response genes by RNAseq in cells treated with (6a) for 6 hs (dashed line delimits $p<0.05$). Graph bar shows mean and SEM*p=0.03*p<0.0002; **p<0.0001.

DETAILED DESCRIPTION OF THE DISCLOSURE

Figure 1A:
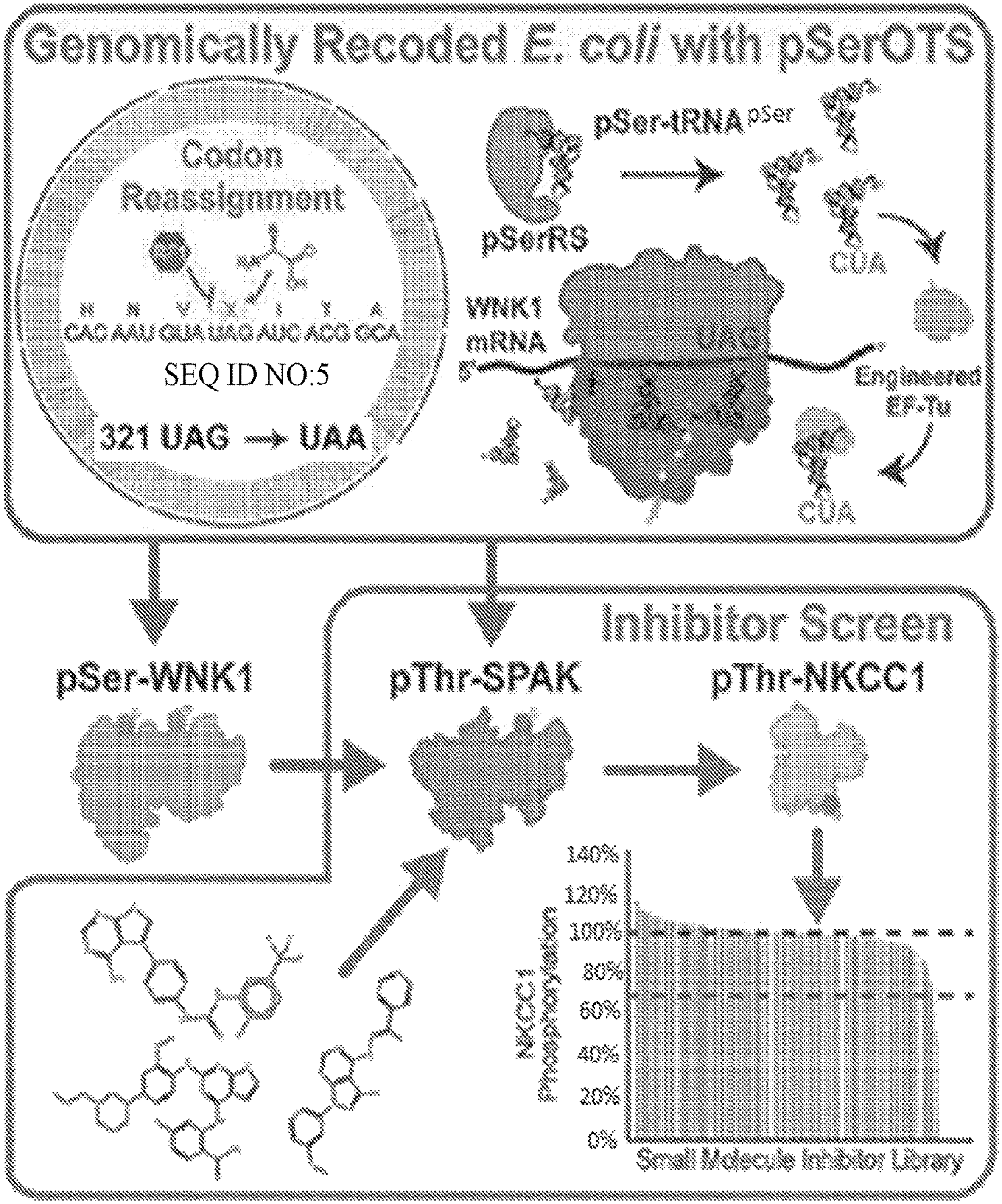
FIGS. 1A-1F illustrate the finding that co-expressed phospho-activated WNK1/SPAK yield highly active kinase preparations.

The present disclosure relates in part to the identification of novel SPAK inhibitors. In certain embodiments, the compounds of the disclosure can be used to inhibit, prevent, and/or minimize proliferation, viability, movement, migration, invasion, and/or cell volume change of certain cancer cells, such as but not limited to glioblastoma multiforme cancer cells and advanced stage cancer cells. In certain embodiments, the cancer comprises melanoma, pancreatic cancer, thyroid cancer, lung cancer, breast cancer, colorectal cancer, and other invasive and metastatic cancers. In certain embodiments, the advanced stage is at least grade III. In certain embodiments, the advanced stage is grade IV.

Cellular signaling and regulatory cascades often rely on post-translational modification (PTM) of proteins to efficiently modulate protein activity and transduce signals in response to environmental cues. Of all PTMs, protein phosphorylation is one of the most common and critical, governing the majority of signaling cascades in humans. Despite their important role in cellular processes, efforts to understand the function of phosphorylation sites are hindered by the apparent complexity of the phosphoproteome. Many kinases are themselves activated by phosphorylation in their kinase domain activation loops, limiting the generation of active, recombinant kinases to the relatively small pool of kinases for which the upstream activating kinase is known. These limitations are highlighted in a large-scale study that showed that the majority of human kinases expressed in bacteria are inactive. Given that these signaling networks form the basis for regulating most physiological processes, there exists a continued scientific interest in understanding these complex networks and connecting specific kinases to their downstream targets.

Ion cotransporters are involved in the invasion of healthy brain tissue by migratory GBM cells. This migratory activity is ultimately regulated through posttranslational phosphorylation, in which the family of WNK kinases have emerged as an important mediator. In addition to this observation, the identification of causal mutations in WNK kinases, which result in hereditary forms of hypertension and hyperkalemia, has guided the focus of many studies toward elucidation of the WNK signaling pathway and downstream substrates. As a result, WNK1 has been shown to regulate the STE20-related kinases SPAK/OSR1, which, in turn, phosphorylate NKCC1 to facilitate cell-volume regulation. Although these studies recognized that WNK-SPAK signaling pathway comprised potential therapeutic targets for controlling aberrant activation of ion co-transporters (as in the case of GBM and hypertension), direct methods for identifying small molecule inhibitors against the physiologically relevant forms of these kinases was technically infeasible. Despite decades of research on GBM, most treatments of this aggressive brain cancer are palliative in nature and the prognosis remains dismal. The poor prognosis is a result of a high proliferation capacity, and more importantly, a highly infiltrative behavior leading to the dissemination of tumor cells throughout the brain.

Malignant cells can modulate cell migration through the extracellular matrix by harnessing complex mechanisms controlling invasive cell spread. Upregulation of ion co-transporter activity has been shown to positively correlate with increased infiltration of migratory glioblastoma (GBM) cells. The activity of some ion co-transporters is directly regulated by the WNK/SPAK/OSR1 kinase network to maintain cellular volume homeostasis. In certain embodiments, inhibition of this signaling network can block invasive GBM migration by compromising cell volume regulation.

As shown herein, the pSerOTS system can be used to produce multiple forms of phosphorylated, active WNK1 kinase to recapitulate the WNK1-SPAK signaling cascade in recoded *E. coli* (without the need for the unknown, upstream activators), allowing for WNK1-dependent phospho-activation of SPAK. Biochemical characterization of the physiologically phosphorylated SPAK demonstrated that the system yields active kinase, and a physiologically active, completely heterologous WNK-SPAK-NKCC1 regulatory network. The overexpressed physiologically activated SPAK reacted with its regulatory accessory protein MO25α. This unique preparation of a druggable kinase pathway enabled a rapid in vitro drug inhibitor screen that yielded a small molecule SPAK kinase inhibitor. This compound showed robust network inhibition in vitro, in model cell lines, and in primary human GBM cell lines. It also arrested tumor growth in subcutaneous xenografts of human GBM cells in vivo. This work not only establishes the physiological basis for targeting aggressive GBM migration as a therapeutic strategy, but also paves a potential path forward toward constructing other phosphoprotein networks as scaffolds for drug discovery. In other words, the SPAK kinase motif provides insight into potential new SPAK substrates that have yet to be identified.

More broadly, the approach to use a heterologous expression system to generate an active, authentically modified human signaling network has the potential to unlock other important signaling pathways for substrate discovery and drug development. Increasing the understanding of kinase functions and their underlying network connectivity present new avenues for the development of therapeutics.

The skilled artisan will understand that the disclosure is not limited to the exemplary therapies discussed herein. Further, the skilled artisan will understand that one or more therapies can be administered alone or in any combination. Still further, the skilled artisan will understand that one or more therapies can be administered in combination with any other type of therapy.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, selected methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, and so forth) from those organisms, tissues, cells or components thereof that display the "normal" (expected) respective characteristic. Characteristics that are normal or expected for one cell or tissue type might be abnormal for a different cell or tissue type.

A disease or disorder is "alleviated" if the severity of a symptom of the disease or disorder, the frequency with which such a symptom is experienced by a patient, or both, is reduced.

As used herein, the term "specifically bind" or "specifically binds," as used herein, is meant that a first molecule (e.g., a target protein or a phosphatase) preferentially binds to a second molecule (e.g., a target protein ligand or a phosphatase ligand, respectively), but does not necessarily bind only to that second molecule. In certain embodiments, the binding is reversible. In other embodiments, the binding is irreversible (or non-reversible).

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount," and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect ($E_{max}$) achieved within an assay.

As used herein, an "instructional material" includes a publication, a recording, a diagram, or any other medium of expression which can be used to communicate the usefulness of a compound, composition, vector, or delivery system of the disclosure in the kit for effecting alleviation of the various diseases or disorders recited herein. Optionally, or alternately, the instructional material can describe one or more methods of alleviating the diseases or disorders in a cell or a tissue of a mammal. The instructional material of the kit of the disclosure can, for example, be affixed to a container which contains the identified compound, composition, vector, or delivery system of the disclosure or be shipped together with a container which contains the identified compound, composition, vector, or delivery system.

Alternatively, the instructional material can be shipped separately from the container with the intention that the instructional material and the compound be used cooperatively by the recipient.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, trifluoroacetic acid, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the disclosure include, for example, ammonium salts, metallic salts including alkali metal, alkaline earth metal and transition metal salts such as, for example, calcium, magnesium, potassium, sodium, and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine), and procaine. All of these salts may be prepared from the corresponding compound by reacting, for example, the appropriate acid or base with the compound.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the patient. Supplementary active compounds may also be incorporated into the compositions. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject, or individual is a human.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the disclosure (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, $—NH_2$, $—N(CH_3)_2$, —C(═O)OH, trifluoromethyl, —C≡N, —C(═O)O($C_1$-$C_4$)alkyl, $—C(═O)NH_2$, $—SO_2NH_2$, $—C(═NH)NH_2$, and $—NO_2$, preferably containing one or two substituents selected from halogen, —OH, alkoxy, —$NH_2$, trifluoromethyl, —$N(CH_3)_2$, and —C(═O)OH, more preferably selected from halogen, alkoxy and —OH. Examples of substituted alkyls include, but are not limited to, 2,2-difluoropropyl, 2-carboxycyclopentyl and 3-chloropropyl.

The term "alkylene" refers to a diradical of an alkyl group. Exemplary alkylene groups include —$CH_2$—, —$CH_2CH_2$—, and —$CH_2C(H)(CH_3)CH_2$—. The term "—($C_0$ alkylene)-" refers to a bond. Accordingly, the term "—($C_{0-3}$ alkylene)-" encompasses a bond (i.e., $C_0$) and a —($C_{1-3}$ alkylene) group.

As used herein, the term "haloalkyl" means alkyl as defined above, substituted by one, two or three substituents selected from the group consisting of F, Cl, Br, and I.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized or substituted. The heteroatom(s) may be placed at any position of the heteroalkyl group, including between the rest of the heteroalkyl group and the fragment to which it is attached, as well as attached to the most distal carbon atom in the heteroalkyl group. Examples include: —$OCH_2CH_2CH_3$, —$CH_2CH_2CH_2OH$, —$CH_2CH_2NHCH_3$, —$CH_2SCH_2CH_3$, —NH—$(CH_2)_m$—OH (m=1-6), —$N(CH_3)$—$(CH_2)_m$—OH (m=1-6), —NH—$(CH_2)_m$—$OCH_3$ (m=1-6), and —$CH_2CH_2$—S(═O)—$CH_3$. Up to two heteroatoms may be consecutive, such as, for example, —$CH_2NH$—$OCH_3$, or —$CH_2CH_2$—S—S—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "cycloalkyl" refers to a mono cyclic or polycyclic non-aromatic radical, wherein each of the atoms forming the ring (i.e. skeletal atoms) is a carbon atom. In certain embodiments, the cycloalkyl group is saturated or partially unsaturated. In other embodiments, the cycloalkyl group is fused with an aromatic ring. Cycloalkyl groups include groups having from 3 to 10 ring atoms. Illustrative examples of cycloalkyl groups include, but are not limited to, the following moieties:

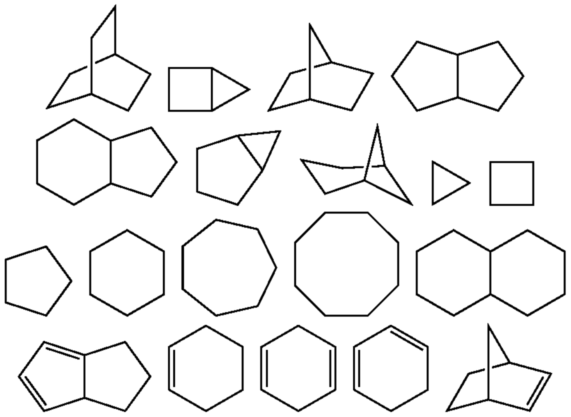

-continued

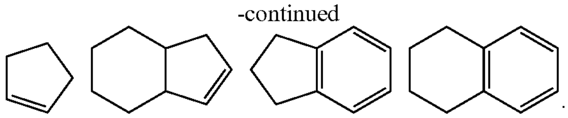

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

The term "carbocyclyl" refers to a saturated or unsaturated carbocyclic ring system containing one or more rings (typically one, two or three rings). In certain embodiments, the carbocyclyl is a 3-12 membered carbocyclic ring, a 3-8 membered carbocyclic ring, or a 3-6 membered carbocyclic ring.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

The term "heteroalkylene" refers to an alkylene group in which one or more carbon atoms has been replaced by a heteroatom (e.g., N, O, or S). Exemplary heteroalkylene groups include —$CH_2O$—, —$CH_2OCH_2$—, and —$CH_2CH_2O$—. The heteroalkylene group may contain, for example, from 2-4, 2-6, or 2-8 atoms selected from the group consisting of carbon and a heteroatom (e.g., N, O, or S).

As used herein, the term "heterocycloalkyl" or "heterocyclyl" refers to a heteroalicyclic group containing one to four ring heteroatoms each selected from O, S and N. In certain embodiments, each heterocycloalkyl group has from 4 to 10 atoms in its ring system, with the proviso that the ring of said group does not contain two adjacent O or S atoms. In other embodiments, the heterocycloalkyl group is fused with an aromatic ring. In certain embodiments, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

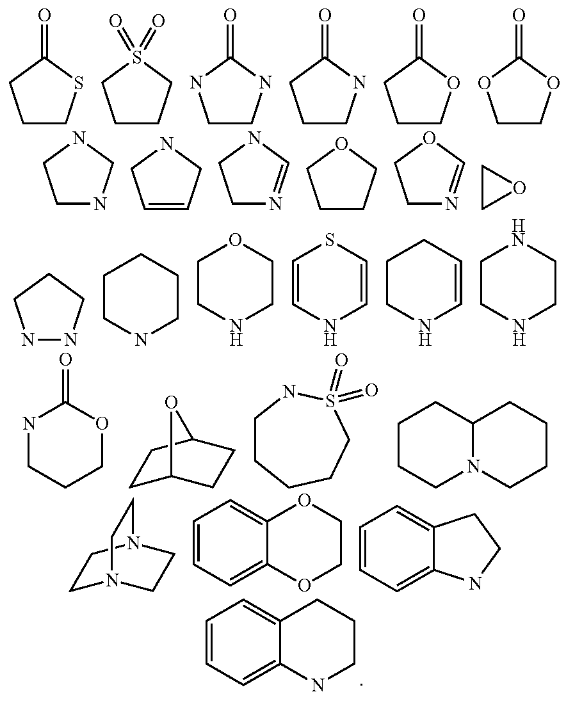

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "heteroaryl" or "heteroaromatic" refers to a heterocycle having aromatic character. A polycyclic heteroaryl may include one or more rings that are partially saturated. Examples include the following moieties:

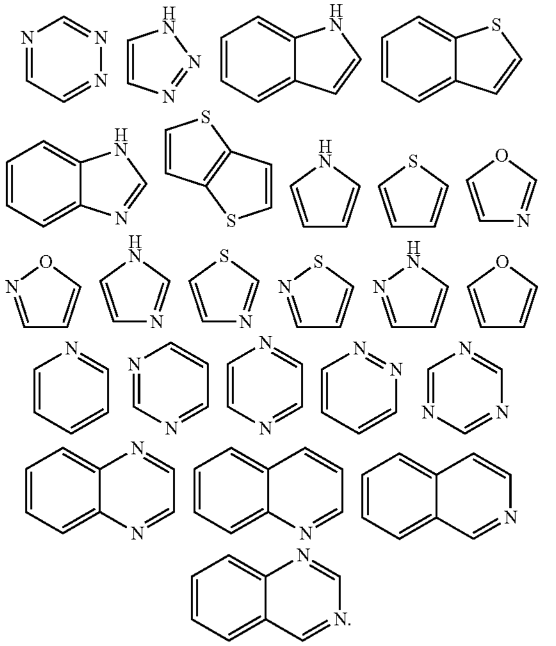

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthenyl, carbazolyl, carbolinyl, acridinyl, pyrrolizidinyl, and quinolizinyl.

The term "heteroarylene" refers to a multi-valent (e.g., di-valent or trivalent) aromatic group that comprises at least one ring heteroatom. An exemplary "heteroarylene" is pyridiylene, which is a multi-valent radical of pyridine. For example, a divalent radical of pyridine is illustrated by the formula

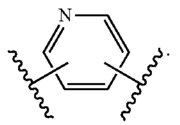

In certain embodiments, the "heteroarylene" is a divalent, 5-6 membered heteroaromatic group containing 1, 2, or 3 ring heteroatoms (e.g., O, N, or S).

The term "phenylene" refers to a multivalent radical (e.g., a divalent or trivalent radical) of benzene. To illustrate, a divalent radical of benzene is illustrated by the formula

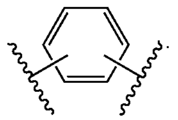

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two.

As used herein, the term "optionally substituted" means that the referenced group may be substituted or unsubstituted. In certain embodiments, the referenced group is optionally substituted with zero substituents, i.e., the referenced group is unsubstituted. In other embodiments, the referenced group is optionally substituted with one or more additional group(s) individually and independently selected from groups described herein.

In certain embodiments, the substituents are independently selected from the group consisting of oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, $S(=O)_2$ alkyl, —C(=O)NH[substituted or unsubstituted alkyl, or substituted or unsubstituted phenyl], —C(=O)N[H or alkyl]2, —OC(=O)N[substituted or unsubstituted alkyl]2, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C($NH_2$)[substituted or unsubstituted alkyl]$_2$. In other embodiments, by way of example, an optional substituent is selected from oxo, fluorine, chlorine, bromine, iodine, —CN, —$NH_2$, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —$S(=O)_2$—$CH_3$, —$C(=O)NH_2$, —C(=O)—$NHCH_3$, —NHC(=O)$NHCH_3$, —C(=O)$CH_3$, and —C(=O)OH. In yet one embodiment, the substituents are independently selected from the group consisting of $C_{1-6}$ alkyl, —OH, $C_{1-6}$ alkoxy, halo, amino, acetamido, oxo and nitro. In yet other embodiments, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

In certain embodiments, an optional substituent is selected from the group consisting of $C_1$-$C_6$ alkyl, $C_3$-$C_8$ cycloalkyl, phenyl, $C_1$-$C_6$ hydroxyalkyl, ($C_1$-$C_6$ alkoxy)-$C_1$-$C_6$ alkyl, $C_1$-$C_6$ haloalkyl, $C_1$-$C_6$ haloalkoxy, halogen, —CN, —$OR^b$, —$N(R^b)(R^b)$, —$NO_2$, —C(=O)$N(R^b)(R^b)$, —$S(=O)_2N(R^b)(R^b)$, acyl, and $C_1$-$C_6$ alkoxycarbonyl, wherein each occurrence of $R^b$ is independently H, $C_1$-$C_6$ alkyl, or $C_3$-$C_8$ cycloalkyl, wherein in $R^b$ the alkyl or cycloalkyl is optionally substituted with at least one selected from the group consisting of halogen, —OH, $C_1$-$C_6$ alkoxy, and heteroaryl; or substituents on two adjacent carbon atoms combine to form —$O(CH_2)_{1-3}O$—.

In certain embodiments, an optional substituent is selected from the group consisting of $C_1$-$C_6$ alkyl, $C_3$-$C_8$ cycloalkyl, phenyl, $C_1$-$C_6$ hydroxyalkyl, ($C_1$-$C_6$ alkoxy)-$C_1$-$C_6$ alkyl, $C_1$-$C_6$ haloalkyl, $C_1$-$C_6$ haloalkoxy, halogen, —$OR^b$, and —C(=O)$N(R^b)(R^b)$, wherein each occurrence of $R^b$ is independently H, $C_1$-$C_6$ alkyl, or $C_3$-$C_8$ cycloalkyl, wherein in $R^b$ the alkyl or cycloalkyl is optionally substituted with at least one selected from the group consisting of halogen, —OH, $C_1$-$C_6$ alkoxy, and heteroaryl; or substituents on two adjacent carbon atoms combine to form —$O(CH_2)_{1-3}O$—.

In certain embodiments, an optional substituent is selected from the group consisting of $C_1$-$C_6$ alkyl, —OH, $C_1$-$C_3$ haloalkyl, $C_1$-$C_6$ alkoxy, $C_3$-$C_8$ cycloalkyl, $C_3$-$C_8$ cycloalkoxy, halo, and —CN.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

The disclosure provides a compound of formula (I), or a salt, solvate, isotopically labelled derivative, stereoisomer, tautomer, or geometric isomer thereof:

(I)

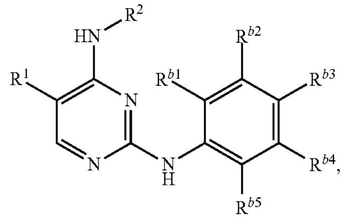

wherein:

$R^1$ is selected from the group consisting of H, F, Cl, Br, I, $C_1$-$C_6$ alkyl, $C_1$-$C_6$ alkoxy, CN, nitro, and $CF_3$;

$R^2$ is selected from the group consisting of:

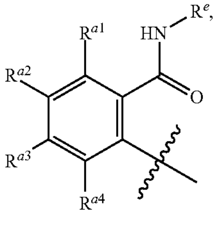

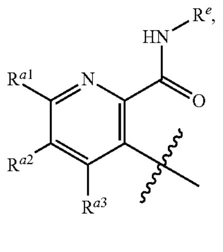

-continued

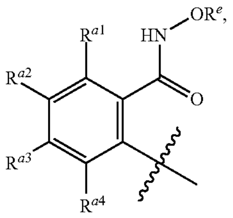

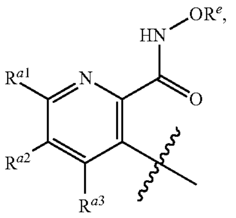

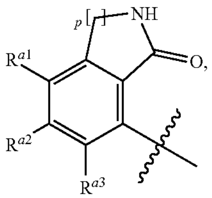

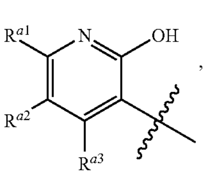

,

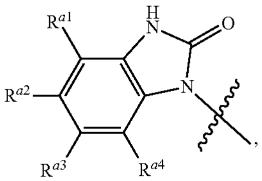

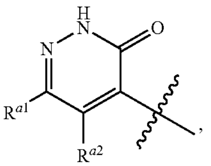

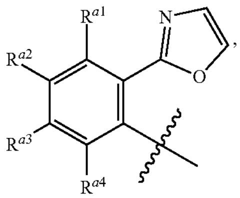

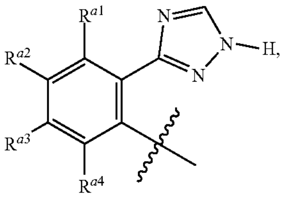

and

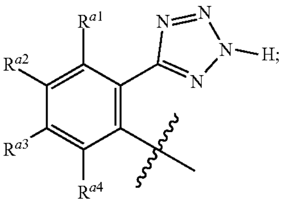

each occurrence of $R^{a1}$, $R^{a2}$, $R^{a3}$, and $R^{a4}$ is independently selected from the group consisting of H, F, Cl, Br, I, $C_1$-$C_6$ alkyl, $C_3$-$C_8$ cycloalkyl, phenyl, $C_1$-$C_6$ hydroxyalkyl, $C_1$-$C_6$ haloalkyl, $C_1$-$C_6$ haloalkoxy, ($C_1$-$C_6$ alkoxy)-$C_0$-$C_6$ alkylene, —$NR^cR^c$, —$OR^c$, —C(═O)$OR^c$, and —C(═O)N($R^c$)($R^c$), wherein each occurrence of $R^c$ is independently H, $C_1$-$C_6$ alkyl, or $C_3$-$C_8$ cycloalkyl, or two $R^c$ bound to the same N atom combine with the N atom to form optionally substituted 3- to 8-membered heterocyclyl;

$R^{b1}$, $R^{b2}$, $R^{b3}$, $R^{b4}$, and $R^{b5}$ are independently selected from the group consisting of H, F, Cl, Br, I, $C_1$-$C_6$ alkyl, $C_3$-$C_8$ cycloalkyl, phenyl, $C_1$-$C_6$ hydroxyalkyl, $C_1$-$C_6$ haloalkyl, $C_1$-$C_6$ haloalkoxy, ($C_1$-$C_6$ alkoxy)-$C_0$-$C_6$ alkylene, —$(CH_2)_{0-3}$—$NR^dR^d$, —$O(CH_2)_{2-3}$—$NR^dR^d$, —$OR^d$, —C(═O)$OR^d$, and —C(═O)N($R^d$)($R^d$), wherein each occurrence of $R^d$ is independently H, $C_1$-$C_6$ alkyl, or $C_3$-$C_8$ cycloalkyl, or two $R^d$ bound to the same N atom combine with the N atom to form optionally substituted 3- to 8-membered heterocyclyl;

each occurrence of $R^e$ is independently $C_1$-$C_6$ alkyl; and p is 1, 2, or 3.

In certain embodiments, $R^1$ is H. In certain embodiments, $R^1$ is F. In certain embodiments, $R^1$ is Cl. In certain embodiments, $R^1$ is Br. In certain embodiments, $R^1$ is I. In certain embodiments, $R^1$ is $C_1$-$C_6$ alkyl (such as but not limited to methyl, ethyl, n-propyl, isopropyl, n-butyl, isobutyl, sec-butyl, tert-butyl, n-pentyl, sec-pentyl, iso-pentyl, neo-pentyl, n-hexyl, sec-hexyl, and so forth). In certain embodiments, $R^1$ is $C_1$-$C_6$ alkoxy (such as but not limited to methoxy, ethoxy, n-propoxy, isopropoxy, n-butoxy, isobutoxy, sec-butoxy, tert-butoxy, n-pentoxy, sec-pentoxy, iso-pentoxy, neo-pentoxy, n-hexoxy, sec-hexoxy, and so forth). In certain embodiments, $R^1$ is CN. In certain embodiments, $R^1$ is nitro. In certain embodiments, $R^1$ is $CF_3$;

In Certain Embodiments, in (I) $R^2$ is

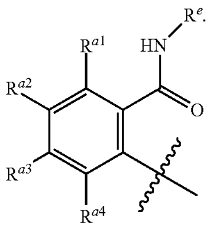

In certain embodiments, in (I) $R^2$ is

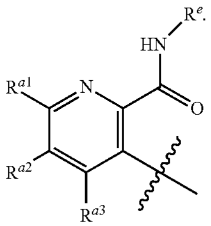

In certain embodiments, in (I) $R^2$ is

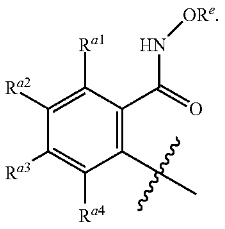

In certain embodiments, in (I) $R^2$ is

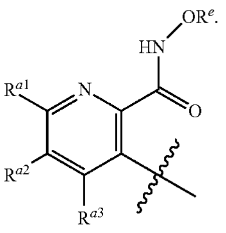

In certain embodiments, in (I) $R^2$ is

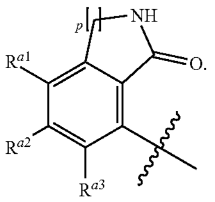

In certain embodiments, in (I) $R^2$ is

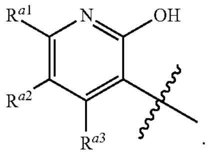

In certain embodiments, in (I) $R^2$ is

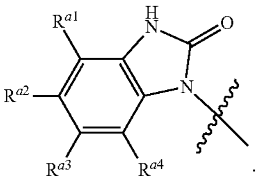

In certain embodiments, in (I) $R^2$ is

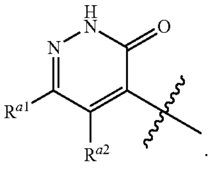

In certain embodiments, in (I) $R^2$ is

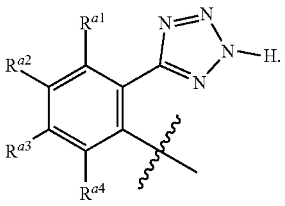

In certain embodiments, occurrence of Ra, $R^{a2}$, $R^{a3}$, and $R^{a4}$ is H.

In certain embodiments, one of $R^{b1}$, $R^{b2}$, $R^{b3}$, $R^{b4}$, and $R^{b5}$ is —$OCH_3$. In certain embodiments, one of $R^{b1}$, $R^{b2}$, $R^{b3}$, $R^{b4}$, and $R^{b5}$ is

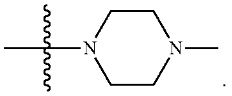

In certain embodiments, $R^{b3}$ is —$OCH_3$, $R^{b4}$ is

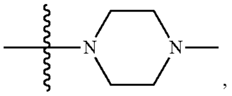 [SMILES: *N1CCN(C)CC1]

and each of $R^{b1}$, $R^{b2}$, and $R^{b5}$ are H.

In some embodiments, the compound of formula (I) is (6b)

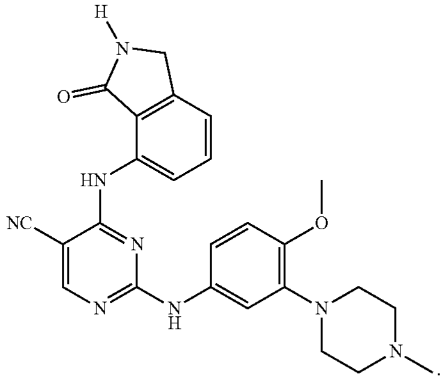

In some embodiments, the compound of formula (I) is (6c)

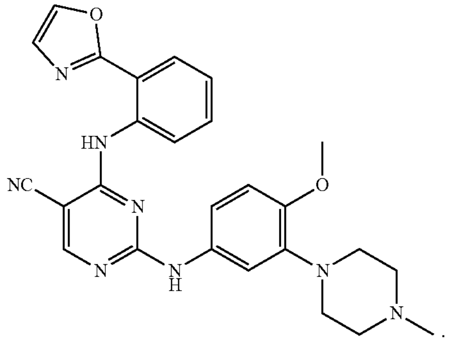

In some embodiments, the compound of formula (I) is (6d)

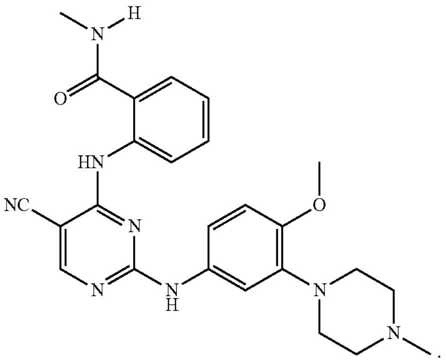

In some embodiments, the compound of formula (I) is (6e)

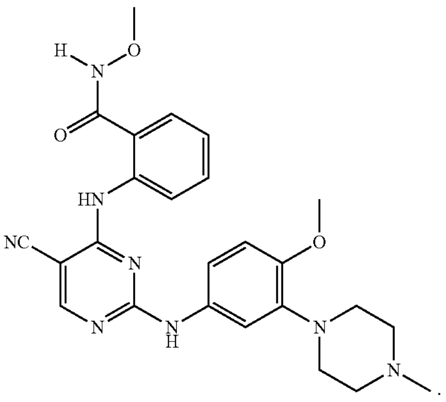

In some embodiments, the compound of formula (I) is (6f)

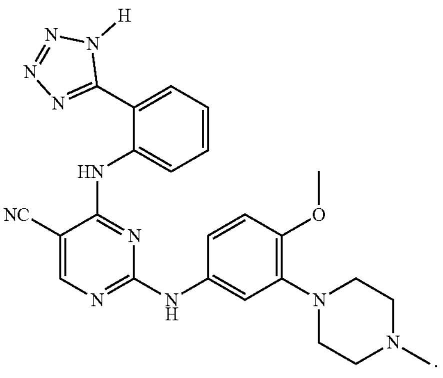

In some embodiments, the compound of formula (I) is

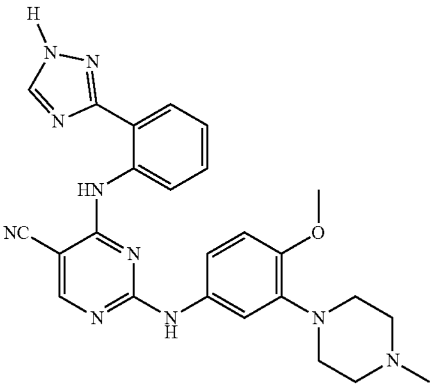

Compounds of the disclosure can be prepared by the general schemes and/or procedures described herein, using the synthetic method known by those skilled in the art.

The compounds of the disclosure may possess one or more stereocenters, and each stereocenter may exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the disclosure, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the disclosure may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the disclosure are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, the compounds of the disclosure are prepared according to the following synthetic scheme:

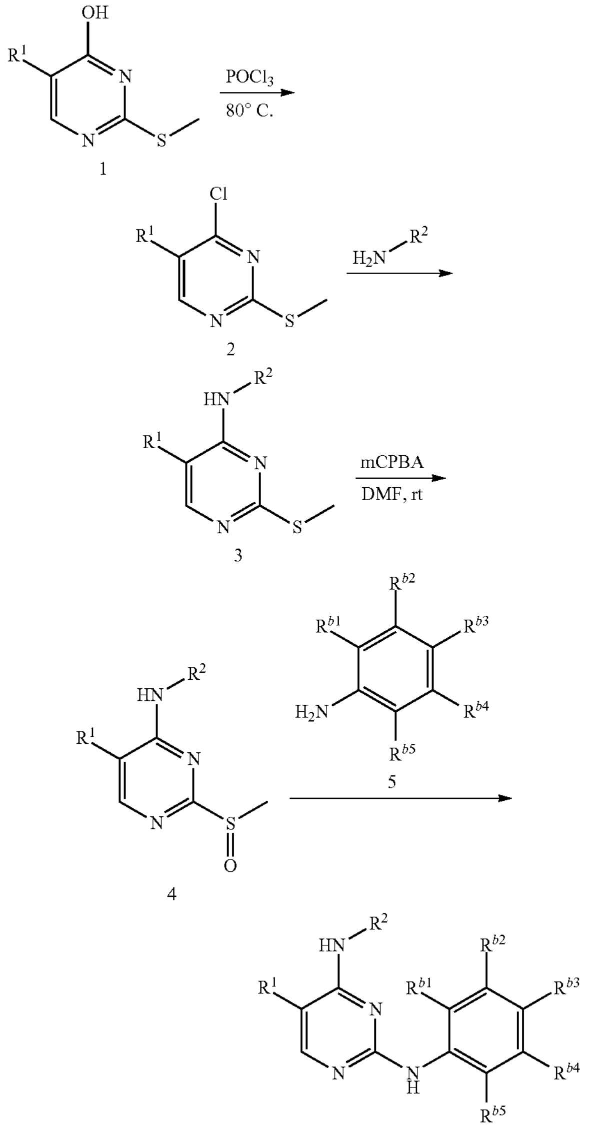

1 2 3 4 5 6

4-Hydroxy pyrimidine compound (1) can be converted to the corresponding 4-chloro pyrimidine compound (2) using a chlorinating reagent, such as but not limited to phosphoryl chloride or phosphorous pentachloride. Reaction of (2) with amine $R^2$—$NH_2$ allows for displacement on the 4-chloro group in (2) so as to form (3). The sulfide in (3) can be oxidized using an oxidant such as meta-chloroperbenzoic acid to yield the corresponding sulfoxide (4), which can be reacted with aniline (5) to form compound (6).

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically Blocking/Protecting Groups May be Selected from:

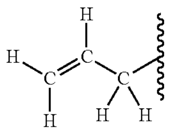
allyl

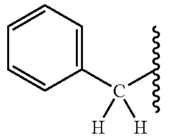
Bn

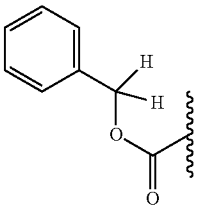
Cbz

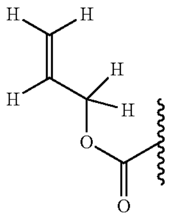
Alloc

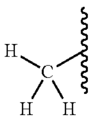
Me

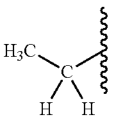
Et

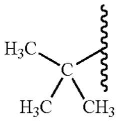
t-butyl

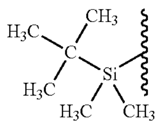
TBDMS

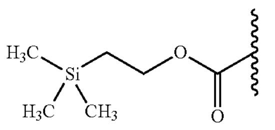
Teoc

-continued

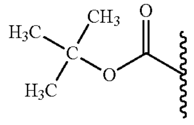
Boc

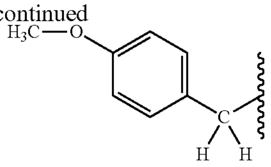
PMB

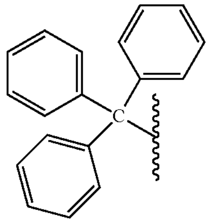
trityl

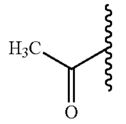
acetyl

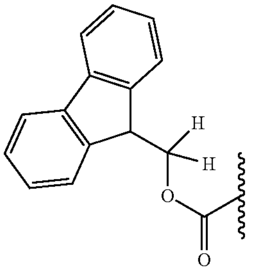
FMOC

.

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Compositions

The disclosure includes a pharmaceutical composition comprising at least one compound of the disclosure and at least one pharmaceutically acceptable carrier. In certain embodiments, the composition is formulated for an administration route such as oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Methods

The disclosure provides compositions and methods for inhibiting SPAK and/or OSR activity. The disclosure further provides compositions and methods for treating, ameliorating, and/or preventing cancer cell migration. The disclosure further provides compositions and methods for reducing or reversing growth of a cancer in a subject. The disclosure further provides compositions and methods for reducing volume of a cancerous tumor in a subject. The disclosure further provides compositions and methods for extending survival in a subject afflicted with a cancer. In certain embodiments, the cancer comprises advanced stage cancer. In certain embodiments, the cancer comprises glioblastoma. In certain embodiments, the cancer comprises melanoma. In certain embodiments, the cancer comprises pancreatic cancer. In certain embodiments, the cancer comprises thyroid cancer. In certain embodiments, the cancer comprises lung cancer. In certain embodiments, the cancer comprises breast cancer. In certain embodiments, the cancer comprises colorectal cancer. In certain embodiments, the cancer comprises invasive and metastatic cancers. In certain embodiments, the advanced stage is at least grade III. In certain embodiments, the advanced stage is grade IV.

In certain embodiments, the method comprises administering to the subject a therapeutically effective amount of a compound of the disclosure.

Vertebrate animals include, but are not limited to, fish, amphibians, birds, and mammals. Mammals include, but are not limited to, rats, mice, cats, dogs, horses, sheep, cattle, cows, pigs, rabbits, non-human primates, and humans. In a specific embodiment, the mammal is human.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this disclosure may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

Compounds of the disclosure for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the disclosure is from about 1 mg and about 2,500 mg. In some embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the disclosure) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present disclosure is directed to a packaged pharmaceutical composition comprising a container holding a therapeutically effective amount of a compound or conjugate of the disclosure, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Pharmaceutical Compositions

The present disclosure provides a pharmaceutical composition comprising at least one nucleic acid molecule of the present disclosure and a pharmaceutically acceptable carrier. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as non-human primates, cattle, pigs, horses, sheep, cats, and dogs.

Pharmaceutical compositions that are useful in the methods of the disclosure may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the disclosure may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the disclosure may further comprise one or more additional pharmaceutically active agents. Other active agents useful in the present disclosure include anti-inflammatories, including corticosteroids, and immunosuppressants, chemotherapeutic agents, antibiotics, antivirals, anti-fungals, and the like.

Controlled- or sustained-release formulations of a pharmaceutical composition of the disclosure may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the disclosure. Thus, single unit dosage forms suitable for oral administration, such as tablets, capsules, gel-caps, and caplets, which are adapted for controlled-release are encompassed by the present disclosure.

In certain embodiments, the formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the disclosure may be administered in the form of microparticles, for example, by injection or in the form of wafers or discs by implantation.

In a preferred embodiment of the disclosure, the compounds of the disclosure are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences (1985, Genaro, ed., Mack Publishing Co., Easton, PA), which is incorporated herein by reference.

Routes of administration of any of the compositions of the disclosure include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. The formulations and compositions that would be useful in the present disclosure are not limited to the particular formulations and compositions that are described herein.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e. powder or granular) form for reconstitution with a suitable vehicle (e.g. sterile pyrogen-free water) prior to parenteral administration of the reconstituted composition.

Kits

The disclosure also provides kits including a compound and/or a composition of the disclosure, and optionally another therapeutic agent, as described herein elsewhere, and instructions for its use. The instructions will generally include information about the use of the compositions in the kit for the treating, ameliorating, and/or preventing the diseases and disorders contemplated here. The instructions may be printed directly on a container inside the kit (when present), or as a label applied to the container, or as a separate sheet, pamphlet, card, or folder supplied in or with the container.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction and/or treatment conditions, with art-recognized alternatives and using no more than routine experimentation, are within the scope of the present application.

EXPERIMENTAL EXAMPLES

The disclosure is further described in detail by reference to the following experimental examples. These examples are provided for purposes of illustration only, and are not intended to be limiting unless so specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the preferred embodiments of the present disclosure, and are not to be construed as limiting in any way the remainder of the disclosure.

Methods:

Synthesis and Structural Characterization:

Unless noted, all reagents, starting materials, and solvents were obtained from commercial suppliers and used without further purifications. Heating, stirring, and reaction workup of the reactions were carried out using standard techniques.

Compounds on TLC were visualized either by UV or staining with $KMnO_4$. Flash-column chromatography was performed using Biotage Isolera One purification system equipped with normal phase silica column (SNAP Ultra) or reverse phase C18 column. $^1H$ and $^{13}C\{^1H\}$ characterization data were collected at room temperature, and chemical shifts are reported in parts per million relative to $CDCl_3$ ($^1H$ NMR; 7.26 ppm, $^{13}C\{^1H\}$ NMR; 77.16 ppm) or DMSO-$d_6$ ($^1H$ NMR; pentet, 2.50 ppm). Mass spectra (MS) were obtained using electrospray ionization (ESI) on a time-of-flight (TOF) mass spectrometer of the LC-MS instrument.

Recombinant Protein Expression and Purification:

Protein Expression: All *E. coli* strains used in this study were made chemically competent using a standard $RbCl_2$ method. EcAR7 cells were co-transformed with plasmids encoding for WNK1 and SPAK variants. Combinations requiring SEP-activation of WNK1 were sequentially made chemically competent and the SEP-OTS plasmid was then transformed. Glycerol stocks were made from the transformed cells containing the correct antibiotic resistance. All cultures were started from a freshly streaked glycerol stock on LB agar plates with the appropriate combination of antibiotics and 0.08% glucose. Pre-cultures were inoculated with 5-20 colonies and grown overnight to confluency in LB media containing 0.08% glucose, and antibiotics. Precultures were diluted to OD600 of 0.15 AU into 100 mL LB media containing 0.08% glucose, antibiotics and 2 mM SEP and were incubated and shaken at 30° C., 230 rpm to an OD600 0.8 AU. Protein expression was then induced with 1 mM IPTG and expressed at 20° C., 230 rpm for ~20-22 hrs. After expression, the cultures were harvested at 4000 g, 20 min, 4° C. All media was decanted, and pellets were stored at −80° C.

Protein Purification: Thawed cell pellets were re-suspended in 5 mL of lysis buffer (50 mM Tris/HCl pH 7.4, 500 mM NaCl, 0.5 mM EDTA, 0.5 mM EGTA, 5 mM DTT, 1 mg/mL lysozyme, 50 mM NaF, 1 mM $NaVO_4$, 10% glycerol, Roche protease inhibitor tablet), and incubated on ice for 30 min, followed by sonication. The lysates were centrifuged at 22,000 g, 15 min, 4° C. and the clarified lysate was transferred to a 15 mL falcon tube, and centrifuged under the same conditions again to remove all remaining insoluble material. The clarified lysate was transferred to 200 μL bed volume of Glutathione Hi-Cap Matrix (Qiagen Valencia, Ca) that was pre-equilibrated in lysis buffer and incubated at 4° C. on a rotisserie shaker for 1 hr. The resin/lysate was centrifuged at 500 g, 5 min 4° C. The lysate was gently removed with ~200 μL of the lysate still above the resin, the lysate slurry mixture was re-suspended and transferred to a Pierce spin column (ThermoScientific Waltham, Ma). The column was washed with 6 mL of GST column wash buffer (50 mM Tris/HCl pH 7.4, 500 mM NaCl, 0.5 mM EDTA, 0.5 mM EGTA, 5 mM DTT, 50 mM NaF, 1 mM $NaVO_4$, 10% glycerol). 200 μL of GST column elution buffer (50 mM Tris/HCl pH 7.4, 500 mM NaCl, 0.5 mM EDTA, 0.5 mM EGTA, 5 mM DTT, 50 mM NaF, 1 mM $NaVO_4$, 10% glycerol, 20 U GST-Prescission™ protease (GE Healthcare Pittsburgh, PA)) was added to the top of the resin. The column was capped and the resin/buffer slurry was incubated at 4° C. on the rotisserie shaker overnight. The 200 μL elution was collected in a clean Eppendorf tube. Two additional 200 μL elutions were collected by adding GST column wash buffer to the top of the column via syringe without disturbing the resin. Expression and purity of each fraction was assessed by SDS-page.

The validated elutions were pooled, concentrated and buffer exchanged into protein storage buffer (50 mM Tris/HCl pH 7.4, 150 mM NaCl, 1 mM DTT, 20% glycerol) using a 0.5 mL amicon ultra centrifugal filter (Millipore Billerica, MA) and the protein was stored at −20° C. The protein concentration was estimated by comparing known quantities of BSA standards on an SDS-page gel. The plasmid encoding for WT-SPAK was transformed into chemically competent BL21 (DE3) cells, and protein was expressed following the same protocol as elsewhere herein, with a few exceptions. Cells were grown at 37° C. prior to induction, and no additives that are required for SEP-Tech were supplemented in the media.

SPAK Kinase Assay Measured by Immunoblotting with $T^P$NKCC1:

Kinase activity of purified WNK1, SPAK and co-expressed WNK1/SPAK variants were evaluated by measuring NKCC1 phosphorylation using the $T^P$NKCC1. Reactions containing different combinations of the following kinases and substrates were reacted for 1 hr at 37° C. in immunoblotting kinase assay buffer (50 mM Tris/HCl pH 7.4, 150 mM NaCl, 1 mM DTT, 20% glycerol, 10 mM $MgCl_2$, 0.2 mM ATP) at a final assay volume of 15 μL: 0.1-20 μM WNK1, 0.5-1 μM SPAK, and 5 μM strep-tagged NKCC1. The reaction was quenched with 15 μL of 2× Laemmli sample buffer, heated to 95° C. for 5 min. Half of the quenched reaction was analyzed on two SDS-Page gels, and the samples were subjected to the immunoblotting procedure described elsewhere herein. Each membrane was cut at the 50 kDa protein marker and the bottom half of one membrane was immunoblotted for $T^P$NKCC1, and the other for Strep-tactin-HRP. The top half of the membranes were immunoblotted for Anti-SPAK, and WNK1 SP382; respectively.

Small Molecule Inhibitor ELISA Screen:

The GlaxoSmithKline published kinase inhibitor set, PKIS (Dranchak, et al., 2013, Plos One 8), was used to evaluate potential SPAK drug inhibitor candidates. The pilot inhibitor screen tested the capability of 320 compounds to inhibit the kinase activity of purified co-expressed SP382 WNK1 (1-661)/WT SPAK using an ELISA based screen monitoring a reduction in NKCC1 phosphorylation with the NKCC1 phospho-specific antibody, $T^P$NKCC1. 10 nL of each inhibitor compound (final concentration 20 μM) or DMSO vehicle controls were added to dry 384 well-flat bottom low volume non-binding assay plates (Corning) using an Echo 550 Acoustic dispenser (Labcyte). 125 nM SPAK (from the co-expressed variant), and 100 nM GST-NKCC1 were mixed with Kinase reaction buffer (50 mM Tris HCl pH 7.5, 150 mM NaCl, 20 mM $MgCl_2$, 2 mM DTT, 0.1% BSA) that did not contain ATP, and 4 μL of the mixture was distributed into each well of the assay plate. The assay plates were centrifuged at 200 g for 1 min, then incubated at RT for 30 min. Following inhibitor incubation, the kinase reaction was initiated with 1 μL of 50 μM ATP (final concentration 10 uM) or 1 μL of Kinase reaction buffer for negative controls and reacted for 1 hr at 37° C. The reaction was then quenched with 5 μL Kinase Stop buffer (100 mM Tris pH 8, 300 mM NaCl, 40 mM EDTA) and incubated for 1 min with shaking at 450 rpm. 2 μL of each quenched reaction was added to 18 μL TBS (50 mM Tris pH 8, 150 mM NaCl) in white 384-well Nunc Maxisorp plates (Thermo Scientific) using a PlateMate Plus (Thermo Scientific). The plate was shaken for 1 min at 450 rpm, sealed and incubated at 4° C. overnight to allow the protein contents of the reaction to bind to the Maxisorp plate. The next morning the solution was removed, and the plates were then subjected to 3 washes in TBST (50 mM Tris pH 7.5, 150 mM NaCl. 0.05% Tween 20) for 5 min each wash with shaking at 400 rpm. The plates were blocked with TBST buffer containing 3% BSA (w/v) at RT for 2 hrs at RT. The blocking buffer was removed, and the plates were immunoblotted with 1:50,000 dilution of $T^P$NKCC1 in blocking buffer for 2 hrs at RT. The plates were then subjected to 3 washes in TBST for 5 min each wash with shaking at 400 rpm, followed by incubating with 1:10,000 dilution of 2° DAR-HPR antibody in blocking buffer for 1 hr at RT. The plates were washed again 3 times in TBST for 5 min each wash with shaking at 400 rpm. Signal was detected by SuperSignal ELISA Pico Chemiluminescent substrate (ThermoScientific), and read on an EnVision multi-label plate reader (Perkin-Elmer).

Cell Culture, Stimulation and Lysis:

Mouse distal convoluted tubule (mDCT15) cells (Naguro, et al., 2012, Nature comm. 3:1285) were cultured in DMEM/Ham's F-12 media supplemented with 1% PSN and 5% FBS. Before each set of experiments $2\times10^5$ cells/well were plated in 24-well plates treated with 100 ug/mL poly-D-lysine and grown at 37° C. in 5% $CO_2$ to ~95% confluency. The culture media was removed and replaced with 250 μL of pre-warmed media containing 1 μL of inhibitor compound at each specific concentration or 100% DMSO vehicle control and incubated for 2 hrs at 37° C. in 5% $CO_2$. To stimulate hyperosmotic conditions, a 5 M NaCl stock was spiked into the media at a final concentration of 0.5 M NaCl and incubated for 10 min at 37° C. in 5% $CO_2$. Following the 10 min incubation the media was removed, and replaced with 1 mL of hypotonic buffer (10 mM Hepes pH 7.4, 70 mM sodium gluconate, 0.5 mM magnesium gluconate, 2.5 mM potassium gluconate, 0.5 mM calcium gluconate, 0.5 mM $Na_2HPO_4$, 0.5 mM $Na_2SO_4$, 5 mM dextrose), to stimulate hypo-osmotic conditions for 30 min at 37° C. in 5% $CO_2$. All media was removed and 100 μL of cell culture lysis buffer (100 mM Tris/HCl pH 7.4, 300 mM NaCl, 5 mM EDTA, 5 mM EGTA, 2 mM DTT, 10% glycerol, 2% triton X-100, Roche protease inhibitor, and phosphatase inhibitor cocktail 3 (Sigma-Aldrich St. Louis, MO)) was added to each well, transferred to a clean 1.5 mL Eppendorf tube, and incubated on ice for a minimum of 10 min. The cell lysates were centrifuged at 21,000 G for 10 min. The clarified lysate was stored at −80° C.

Glioblastoma Cell Migration:

Cell culture: All primary cell lines were derived from intraoperative tissue samples from patients treated surgically for newly diagnosed glioblastoma multiforme without prior treatment. Primary cells were cultured in Dulbecco's Modified Eagle Medium: Nutrient Mixture F-12, B27 serum free supplement (Gibco), 20 ng/mL epidermal growth factor (EGF), and 20 ng/ml fibroblast-derived growth factor (FGF).

Nanogrooved pattern cell migration assay: Migration of glioma cells was quantified using a novel directional migration assay using nano-ridges/grooves of 400 nm in groove width, 400 nm in ridge width, and 500 nm in depth, constructed of transparent poly(urethane acrylate) (PUA), and fabricated using UV-assisted capillary lithography (Kim & Eberwine, 2010, Anal. Bioanl. Chem. 397:3173-3178). Cells were cultured on glass covered with a nanogrooved pattern substratum, which was previously glued onto the bottom surface of the custom-made Mat-tek dish (P35G-20-C). Prior to plating cells, nanogrooved substrata were coated with poly-L-ornithine (10 ug/ml concentration) for 15 minutes and laminin (10 ug/ml concentration) for 1 hour. These topographically patterned cell substrata, caused cells to align with and move along the direction of the nanogrooves. Cell migration was quantified using time-lapse microscopy using a motorized inverted microscope (Olympus IX81) equipped with a Cascade 512B II CCD camera and temperature and gas controlling environmental chamber. Phase-contrast and epi-fluorescent cell images were automatically recorded under 4*1.6× objective using the Slidebook 4.1 (Intelligent Imaging Innovations, Denver, CO) for 10 hours at 10 minute intervals.

Quantitative analysis of cell migration: A custom-made MATLAB script was used calculate cell speed and persistence using time-lapse microscopy data as described previously (Garzon-Muvdi, et al., 2012b, Plos Biology 10). Average speeds of individual cells were calculated from the total distance moved throughout the entire cell trajectory and the total time the cell was tracked. Persistence was obtained by calculating the ratio of the shortest distance between start and end points, divided by the total distance moved.

Cell Proliferation:

Glioblastoma cells were plated in triplicates in 96-well plates at a cell density of 10,000 cells per well and incubated with increasing concentrations of (7a) inhibitor for 72 hs. Cell viability was determined by Thiazolyl Blue Tetrazolium Bromide (MTT) assay (Sigma) according to manufacturer instructions. $IC_{50}$ was determined using GraphPad software by non-linear regression analysis (log (inh) vs. normalized response).

Tumor Xenograft:

8-week male nude mice (athymic nude Foxn1nu, Jackson Laboratories, USA) were injected subcutaneously in the right flank with $2\times10^6$ primary glioblastoma cells (previously transduced with lentiviral particles to constitutively express GFP-Luciferase gene). Cells were resuspended in 200 μL of 1:1 mixture of DMEM F12:Matrigel matrix (Corning). Tumors were allowed to grow to 100 $mm^3$ and then mice were randomized into individual treatment groups: the control vehicle group received PBS-0.025% DMSO (270 μL/dose), and the treated group received 0.1 mg/kg (7a) in PBS-0.025% DMSO (270 μL/dose). Daily treatment was given by intraperitoneal injections for 17 days. Tumor growth was assessed by Bioluminescence imaging.

Bioluminescence Imaging:

In vivo bioluminescence images of tumor-implanted mice were obtained using the IVIS Spectrum System. Before imaging, D-luciferin (XenoLight D-Luciferin-$K^+$ Salt Bioluminescent Substrate Perkin Elmer) was injected I.P., at a dose of 10 mg/kg and allowed to distribute for 10 min. Mice were imaged once a week after tumor engrafting. Data acquisition and analysis were performed using the Living Image Software. For quantitation of the detected light, regions of interest were drawn and the light emitted was recorded as the total flux (number of photons per second). Statistical analysis was performed using GraphPad software by 2-way RM ANOVA and Sidak multiple comparisons test.

Plasmid Constructs:

The following plasmids were provided from the Division of Signal Transduction (DSTT), Dundee: WT-WNK1 (DU6025), WT-SPAK (DU6040), Kinase Dead D212A-HA SPAK (DU6013), WT OSR1 (DU41905), and WT-MO25α (DU2945) in the pGEX-6P-1 backbone. All WNK and SPAK/OSR1 variants used in this study were made either by cloning, mutagenesis, or PCR and are derived from the DSTT plasmids following standard procedures. A zeocin antibiotic marker cassette was subcloned in place of the ampicillin antibiotic marker of the pGEX-6P-1 vector backbones for WT SPAK and WT OSR1 that were co-expressed with WNK1 variants. Each WNK1 variant derived from DU6025 is described in FIG. 18.

The pSerOTS was constructed by combining the pSepT and pKD-SepRS-EFSep plasmids to create an all-in-one orthogonal translation system (OTS). The 250 bp $tRNA^{sep}$ cassette was PCR amplified from the pSepT plasmid using primers tRNA$^{sep}$-F (5'-ACC GCG GCC GCA AAA AAA ATC cttagctttcg-3'; SEQ ID NO: 1) and tRNAsep-R (5'-AAA GCG GCC GCG CTT CTT TG agcgaac-3'; SEQ ID NO: 2). The PCR primers added NotI restriction sites to each end of the PCR product. The pKD-SepRS-EFSep plasmid was linearly digested with NotI and five copies of the tRNAsep cassette were ligated sequentially.

N-terminal Strep-tagged human NKCC1 (Residues 1-260) was codon-optimized for *E. coli* and synthesized by Genewiz (South Plainfield, NJ). The gene fragment was subcloned into in pGEX-6P-1 using a 5' and 3' BamHI restriction site.

Antibodies:

WNK1 $S^P$382 a rabbit polyclonal, phospho-specific antibody for $S^P$382 WNK1 was gifted from Richard Lifton, Yale University. To produce the antibody specific to WNK kinases phosphorylated at S382, the human WNK peptide acetyl-CGLATLKRASFAKS*VIG-cysteine (*phosphor-Ser) (SEQ ID NO: 3), was coupled to keyhole limpet hemocyanin, and rabbits were immunized by the phosphopeptide (Covance Research Products). Pooled serum was depleted of nonspecific antibodies with the cognate non-phosphopeptide, and specific antibody was purified with the immunizing phosphopeptide. The antibody was used at a dilution of 1:10,000. $T^P$NKCC1 (R5), a rabbit polyclonal phospho-specific antibody for aphospho-NKCC (Flemmer J B C 2002) was gifted from Biff Forbush, Yale University and used at a dilution of 1:10,000 for both immunoblotting and ELISA. Strep-Tactin HRP conjugate was purchased from Iba-Life Sciences and used at a dilution of 1:50,000. Anti-SPAK a sheep polyclonal for total SPAK was purchased from the DSTT, Dundee used at a dilution if 1 μg/mL. Donkey Anti-Rabbit-RP (DAR-RP) and Donkey Anti-Sheep HRP (DASh-RP) were purchased from Jackson ImmunoResearch and used at a dilution of 1:10,000.

Immunoblotting:

Protein samples were subjected to electrophoresis on polyacrylamide gels and transferred to PVDF membranes. The membranes were incubated overnight in TBST blocking buffer containing 5% milk (w/v) (for the antibodies raised in sheep) or 3% BSA (w/v) (for all other antibodies). The membranes were immunoblotted with one of the following 1° antibodies in the appropriate blocking buffer for the denoted amount of time at RT: $S^P$WNK1 S382 (2 hrs), $T^P$NKCC1 (2 hrs), Strep-Tactin-RP (1.5 hrs), or Anti-SPAK (1 hr). The membrane was then subjected to 3 washes in TBST for 5 min each, followed by the appropriate 2° antibody in blocking buffer for 1 hr at RT. The membranes were washed again 3 times in TBST for 5 min each. Signal was detected by enhanced chemiluminescence (Bio-rad) imaged on a ChemiDoc™ XRS+ CCD camera.

SPAK Sample Preparation for Mass Spectrometric Analysis:

Roughly 200 ng of the purified SPAK or co-expressed SPAK kinases were loaded on a 4-12% Bis-Tris Invitrogen gel for SDS-page analysis. The gel was stained with Instant Blue™ (Expedeon, Harston Cambridgeshire, UK) for 1 hr followed by destain in $dH_2O$ overnight. The protein bands at the molecular weight corresponding to SPAK were excised and the gel pieces were cut into 1 mm cubes and put into clean 1.5 mL eppendorf tubes. Each sample was then sequentially washed for 10 min in 0.5 mL of each of the following solutions $H_2O$, 50% acetonitrile/$H_2O$, 0.1 M $NH_4HCO_3$ and finally 50% acetonitrile/50 mM $NH_4HCO_3$ aspirating the liquid between each wash step. Next, the samples were "in gel" alkylated by adding 75 μL of 10 mM DTT/0.1 M $NH_4HCO_3$ to each sample and incubating at 37° C. for 20 min. The liquid was aspirated, and 75 μL of 50 mM iodoacetamide/0.1 M $NH_4HCO_3$ was added to each sample and incubated at room temperature in the dark for 20 min. The liquid was aspirated, and the samples were further washed for 10 min in 0.5 mL 50 mM $NH_4HCO_3$ followed by 50% acetonitrile/50 mM $NH_4HCO_3$. The gel pieces were shrunk with 0.3 mL acetonitrile for 15 min. The liquid was aspirated and the samples were dried by SpeedVac. The dried gel pieces were incubated with 50 μL of 25 mM triethylammonium bicarbonate containing 5 μg/ml of Trypsin shaking at 30° C. overnight. Following the digestion, 50 μL of acetonitrile was added to the samples and they were incubated for 15 minutes. The supernatant was collected in a clean 1.5 mL Eppendorf tube and dried by SpeedVac. 100 μl of 50% acetonitrile/2.5% formic acid was added to the gel bands and incubated for 15 minutes. For mass spectrometry fingerprint analysis, the supernatant from the second extract was combined with the dried first extract then dried completely in a SpeedVac. The dried sample was stored at −20° C. for analysis.

Mass Spectrometric Analysis:

MS analysis was performed by LC-MS-MS using a linear ion trap-orbitrap hybrid mass spectrometer (Orbitrap-Classic, Thermo) equipped with a nanoelectrospray ion source (Thermo) and coupled to a Proxeon EASY-nLC system. Peptides were injected onto a Thermo (Part No. 160321) Acclaim PepMap100 reverse phase C18 3 μm column, 75 μm×15 cm, with a flow of 300 nl/min and eluted with a 45 min linear gradient of 95% solvent A (2% Acetonitrile, 0.1% formic acid in $H_2O$) to 40% solvent B (90% acetonitrile, 0.08% formic acid in $H_2O$), followed by a rise to 80% B at 48 min. The instrument was operated with the "lock mass" option to improve the mass accuracy of precursor ions and data were acquired in the data-dependent mode, automatically switching between MS and MS-MS acquisition. Full scan spectra (m/z 340-1800) were acquired in the orbitrap with resolution R=60,000 at m/z 400 (after accumulation to an FTMS Full AGC Target; 1,000,000; MSn AGC Target; 100,000). The 5 most intense ions, above a specified minimum signal threshold (5,000), based upon a low resolution (R=15,000) preview of the survey scan, were fragmented by collision induced dissociation and recorded in the linear ion trap, (Full AGC Target; 30,000. MSn AGC Target; 5,000). Multi-Stage-Activation was used to provide an MS3 scan of any parent ions showing a neutral loss of 48.9885, 32.6570, 24.4942, allowing for 2+, 3+ and 4+ ions respectively. The resulting MS3 scan was automatically combined with the relevant MS2 scan prior to data analysis. RAW files containing only CID data from the Orbitrap-Classic were analysed both by using RAW2msm (Matthias Mann, Max-Planck Institute) followed by Mascot (matrixscience dot com) searching against an in house database containing the relevant sequences and analysed directly by using Proteome Discoverer 1.4 and phosphoRS 3.1 (Thermo), searching against the same database.

Kinase Motif Peptide Screen:

The peptide library (Kinase Substrates Library, Groups I and II, Anaspec, Inc.) has been described previously (Mok, et al., 2010, Sci. Signaling 3:ra12-ra12) and it consists of 198 peptide sets of the form Y-A-X-X-X-X-X—S/T-X-X-X-X-G-A-K—K (biotin) (SEQ ID NO: 4), where, for each set, 8 of the 9 positions labeled X are degenerate mixtures of all 20 amino acids except serine, threonine, and cysteine. The other X position is fixed as one of the 20 standard amino acids or either phosphothreonine or phosphotyrosine, and the S/T represents an equimolar mixture of serine and threonine at the phosphorylation site. These 22 fixed amino acids at 9 positions comprise 198 peptide sets. The library also contains three peptides of the same form but with all the 9× positions degenerate and only serine, threonine, or tyrosine at the phosphorylation site. These 201 peptide sets were assayed with SPAK in reaction buffer (50 mM Tris, pH 7.5, 10 mM $MgCl_2$, 1 mM EGTA in 0.1% tween) at final concentrations of 51 μM peptide library substrate, 10 nM SPAK or SPAK (kinase dead), 23 nM GST-M025, 82 ng/μl BSA, and 45 μM ATP (including 0.027 μCi/μL [γ-$^{33}$P]ATP). The remaining transfer and washing steps of the assay were completed as previously described (Miller and Turk, 2016, Rapid Identification of Protein Kinase Phosphorylation Site Motifs Using Combinatorial Peptide Libraries. In Kinase Screening and Profiling: Methods and Protocols, H. Zegzouti, and S. A. Goueli, eds. (New York, NY: Springer New York), pp. 203-216). The kinase dead control of SPAK prepared with active Wnk gave no detectible signal. After phosphorimager scanning (Molecular Imager FX Pro Plus, Bio-Rad), the median intensity of each spot was extracted. These values were then background corrected by subtracting the average signal of the 19 wells that contained kinase but no peptide. These background corrected data were then normalized by dividing them by the average intensity of all the 20 standard amino acids at the same fixed position. SPAK was assayed in duplicate, and the normalized data for each run were averaged. A Logo was created by inputting the positive values following log 2 transformations of these normalized, background corrected intensities into an online server (benoslab dot pitt dot edu/cgi-bin/enologos/enologos dot cgi)(Workman, et al., 2005, Nucleic Acids Res 33:W389-W392).

SPAK Kinase Assay Measured by $^{32}$P Radioactivity:

30 nM SPAK, 2 μM GST-NKCC1 (DU6146), +1 μM GST-MO25α (DU30906) were reacted at 30° C. in a Thermomixer at 1000 rpm from times ranging from 0-20 min in $^{32}$P radioactive kinase assay buffer (50 mM Tris/HCl pH 7.4, 0.1 mM EGTA, 10 mM $MgCl_2$, 0.1 mM [$^{32}$P]-ATP (~200 c.p.m/pmol), 1 μM ovalbumin) at a final volume of 20 μL. The reactions were quenched with 20 μL of 2× Laemmli sample buffer, heated to 70° C. for 10 min. The samples were subjected to electrophoresis on polyacrylamide gels, and stained with Instant Blue™ for 1 hr followed by destain in $dH_2O$ for 1 hr. The gels were rinsed in $dH_2O$ containing 5% glycerol and then sandwiched between two sheets of cellophane clamped to a gel-drying apparatus and dried in a GelAir Dryer (Bio-Rad Hercules, CA). Once dry, the gels were placed in an autoradiography cassette and exposed to GE Hyperfilm MP X-ray film overnight. The films were then developed using a Konica automatic developer. Following autoradiography, the bands corresponding to NKCC1 were excised from the dried gel, transferred to microcentrifuge tubes and $^{32}$P-radioactivity incorporation was quantified by Cerenkov counting.

Histological Staining:

Mouse tumors were dissected and fixed overnight at 4° C. in 4% paraformaldehyde. Tissues were then processed for dehydration, clearing, and embedded in paraffin. Tissue sections (10 μm thick) were obtained and stained with H & E. Images were obtained using an upright light microscope (Axioscope, Zeiss).

Figure 1B:
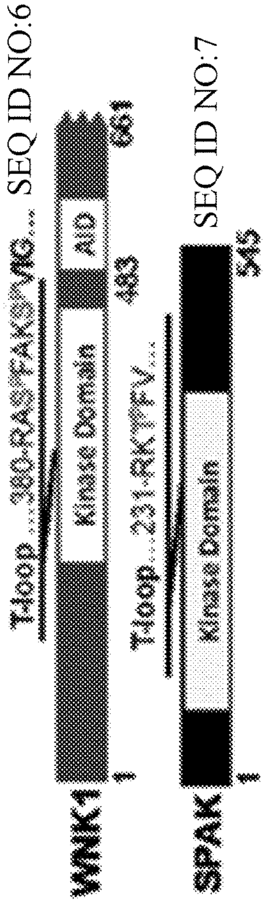
Figure 1C:
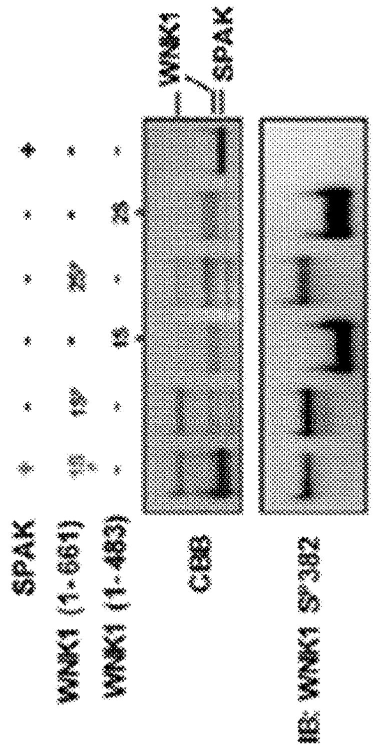
Figure 1D:
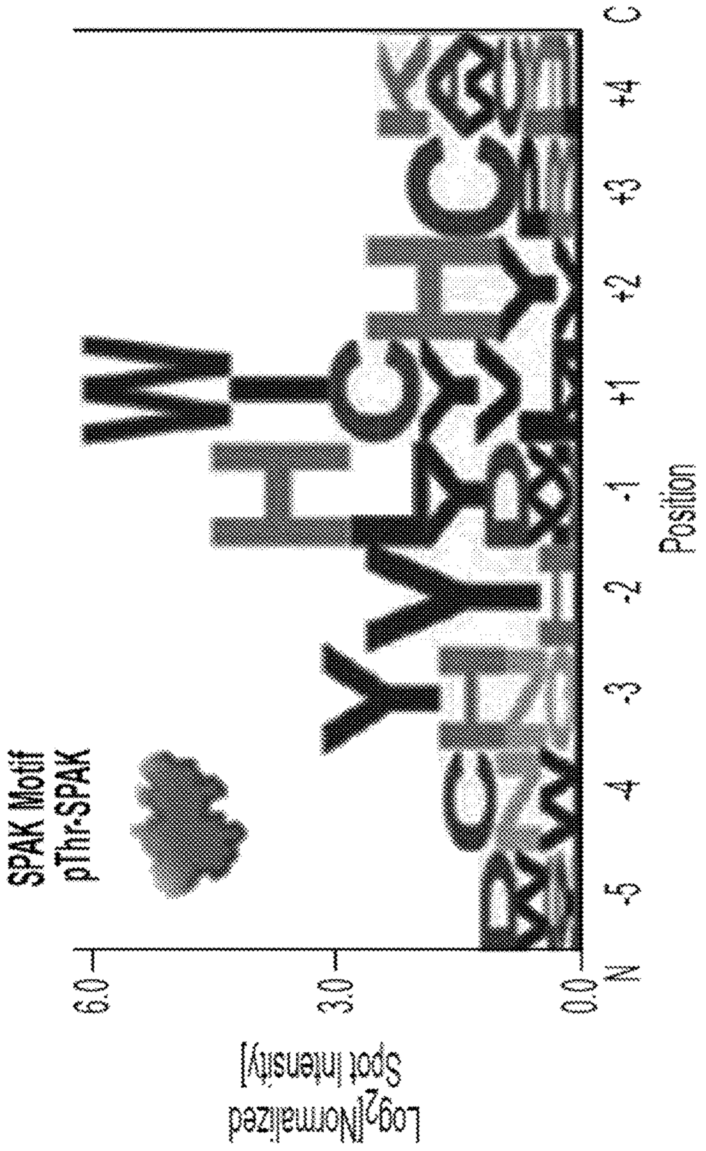
Figures 1E, 1F:
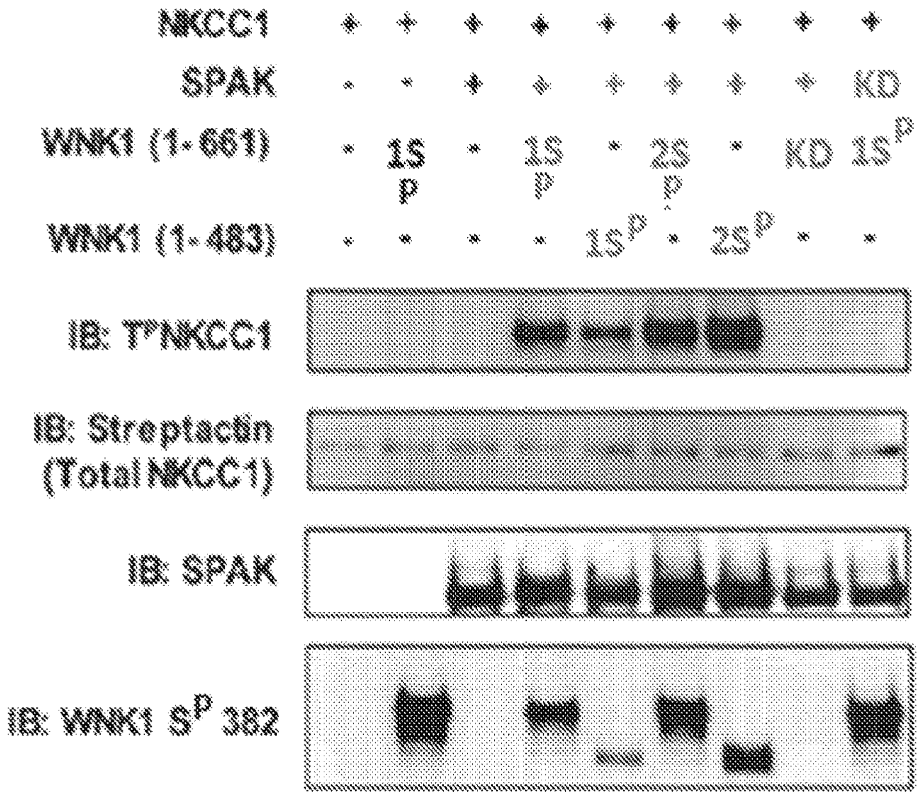
Figures 1, 7A:
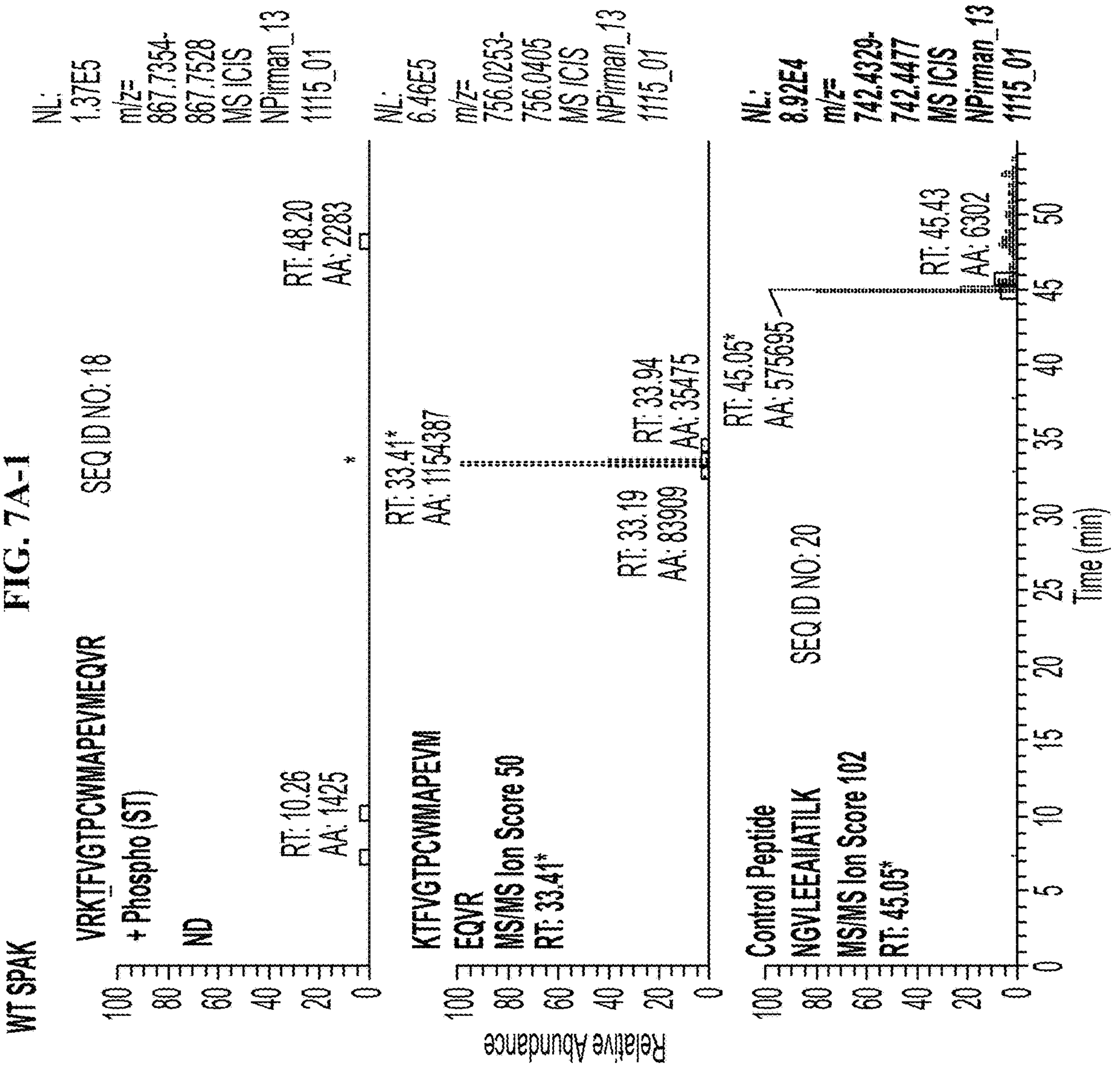
FIGS. 7A-7B illustrate the finding that mass spectrometry analysis of phosphorylated SPAK. WNK1-mediated SPAK phosphorylation at (FIG. 7A) T233 and (FIG. 7B) S373 was validated by mass spec analysis.
Figures 2, 7A:
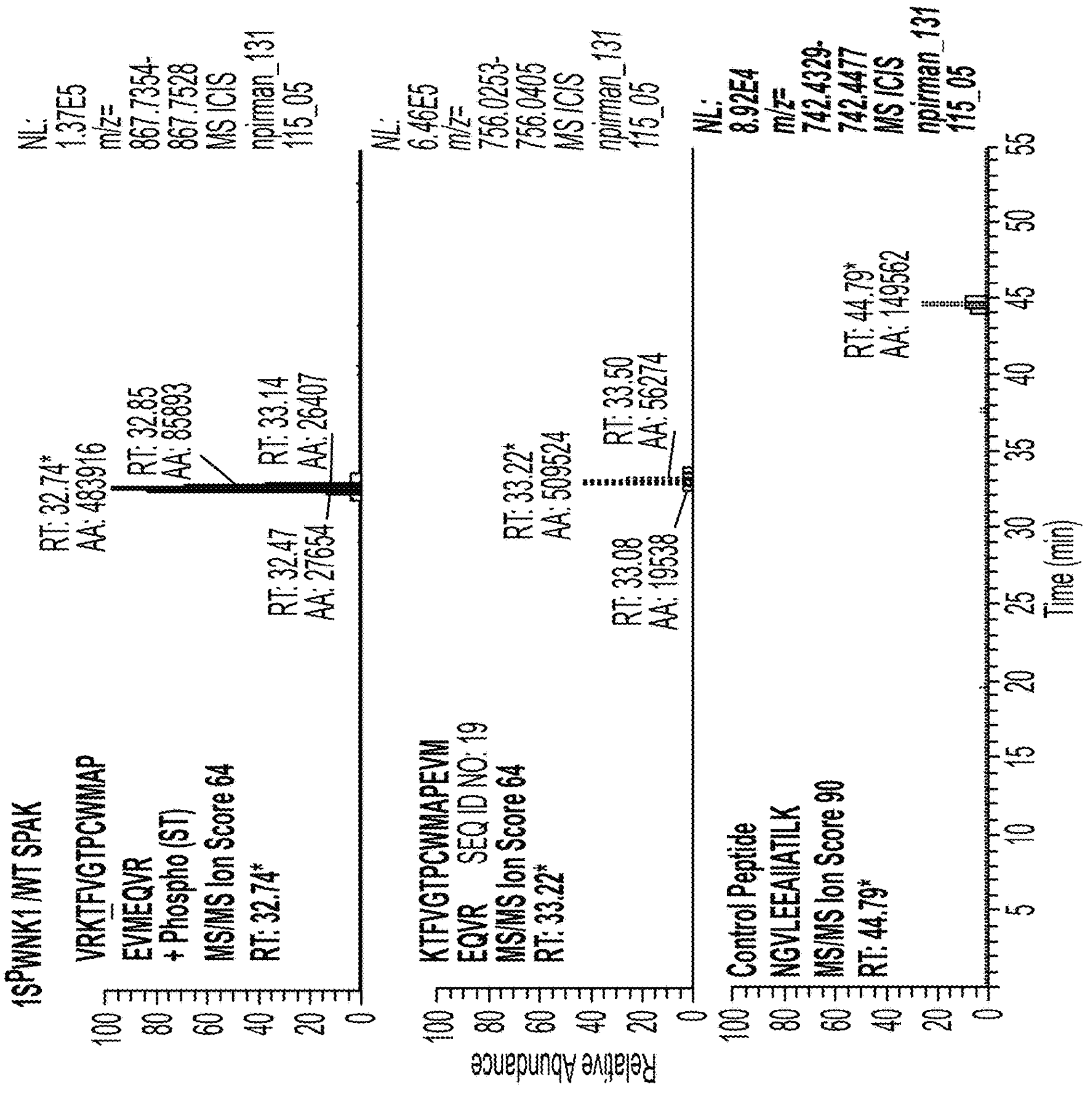
Figures 1, 7B:
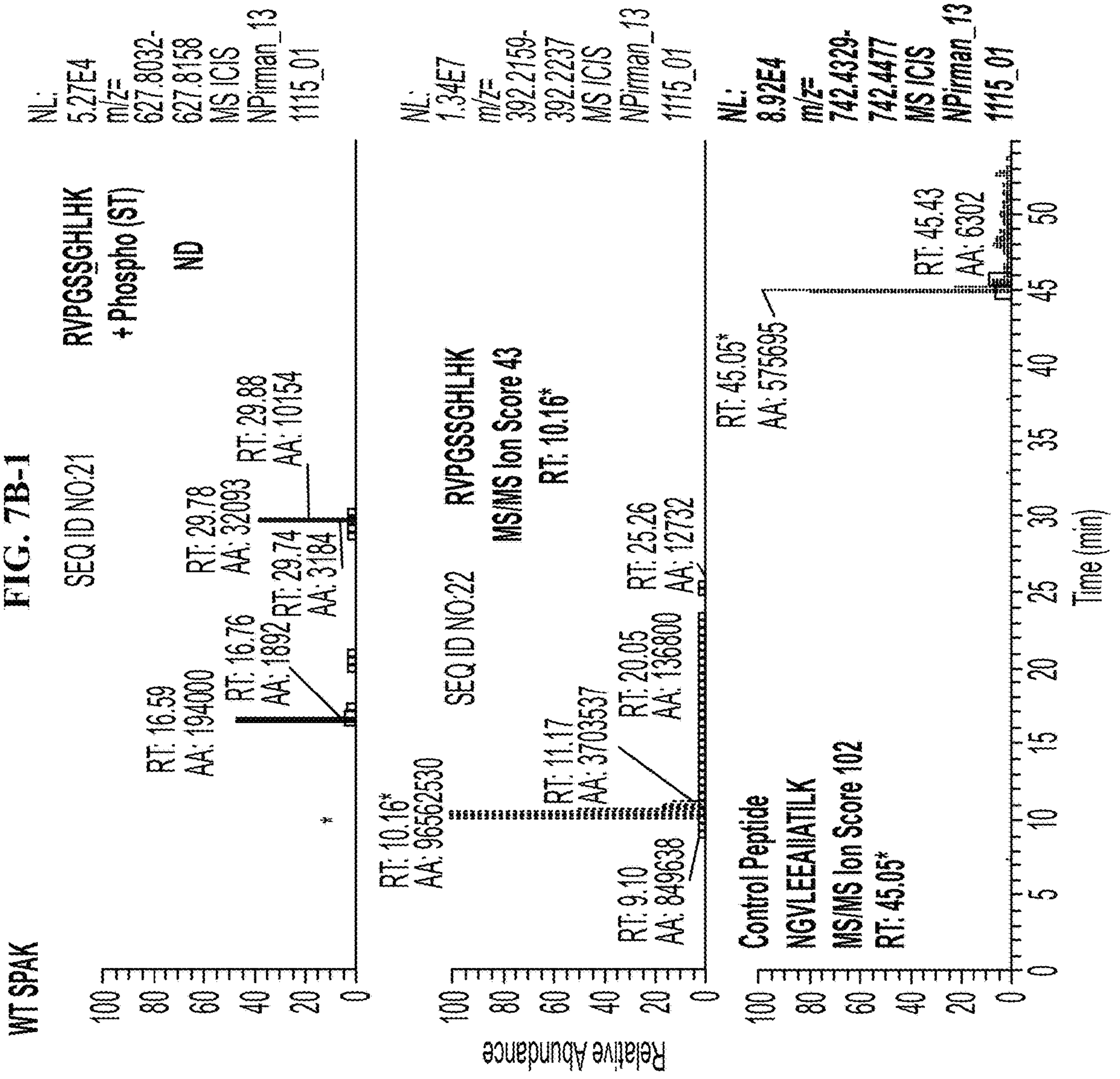
Figures 2, 7B:
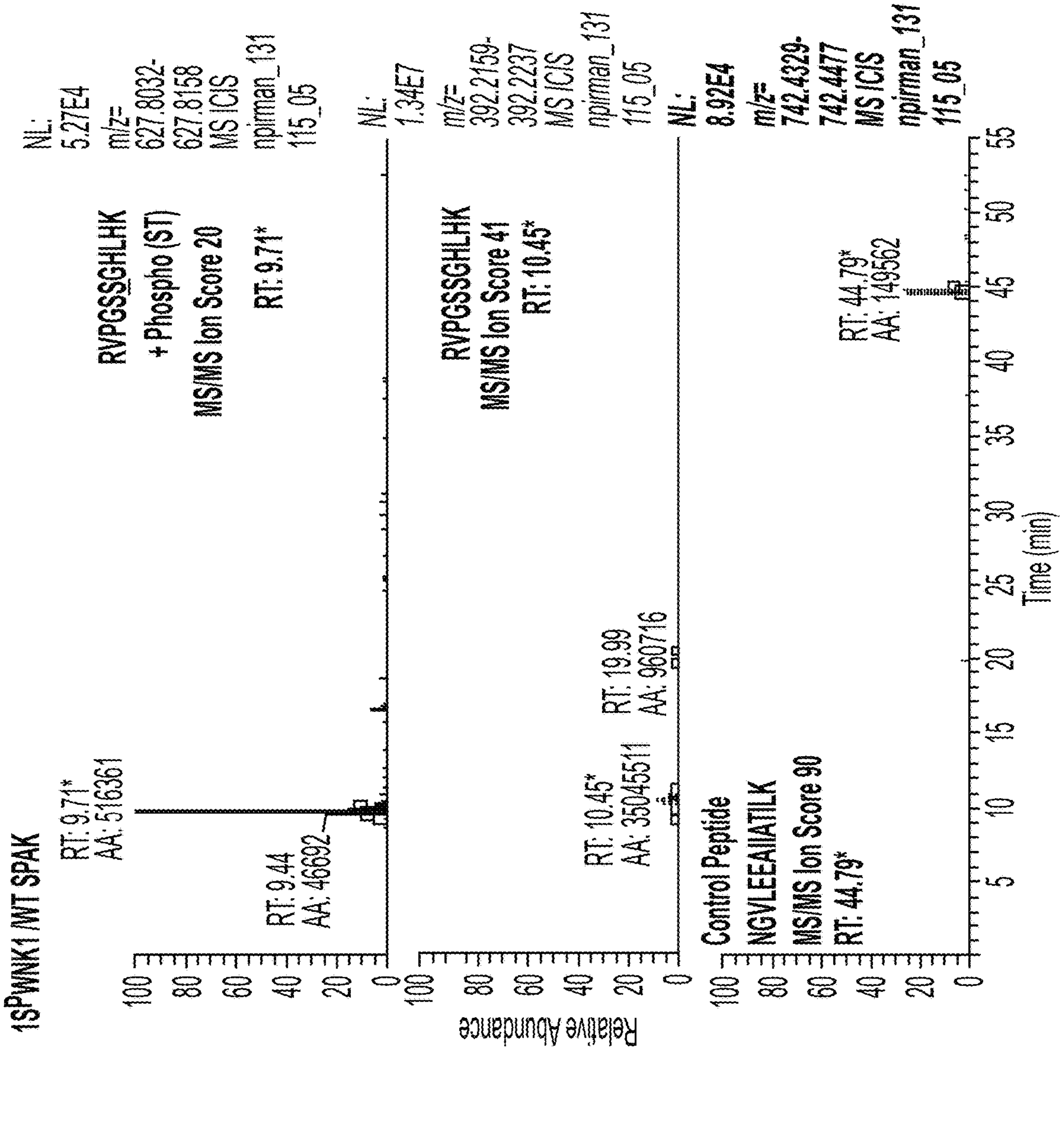

Example 1: Recombinant Phosphorylated WNK1 Reconstitutes a Native WNK-SPAK Signaling Network Using the pSerOTS, multiple forms of phosphorylated human WNK1 were expressed with (1-661) and without (1-483) its native autoinhibitory domain (AID). Additionally, full-length SPAK was expressed solely and co-expressed with phospho-activated WNK1 for downstream evaluation of WNK1 activity (FIGS. 1A-1B). The kinases were purified using affinity chromatography, and phosphoserine incorporation was confirmed using a phosphospecific antibody recognizing SP382 WNK1 and by mass spectrometry (FIG. 1C and FIGS. 7A-7B). Kinase activity was measured with an N-terminal fragment of the ion co-transporter NKCC1 and a phosphospecific antibody (Flemmer, et al., 2002, J. Biol. Chem. 277:37551-37558). When expressed separately, neither $S^P$382-WNK1 nor SPAK could phosphorylate the NKCC1 substrate (FIG. 1F, lanes 1-3). However, robust NKCC1 phosphorylation was observed when SPAK was co-expressed with any of the four SP-WNK1 constructs (FIG. 1F, lanes 4-7). NKCC1 phosphorylation was abolished when kinase dead (KD) WNK1 or KD SPAK was used in the system (FIG. 1F, lanes 8-9).

Figure 5A:
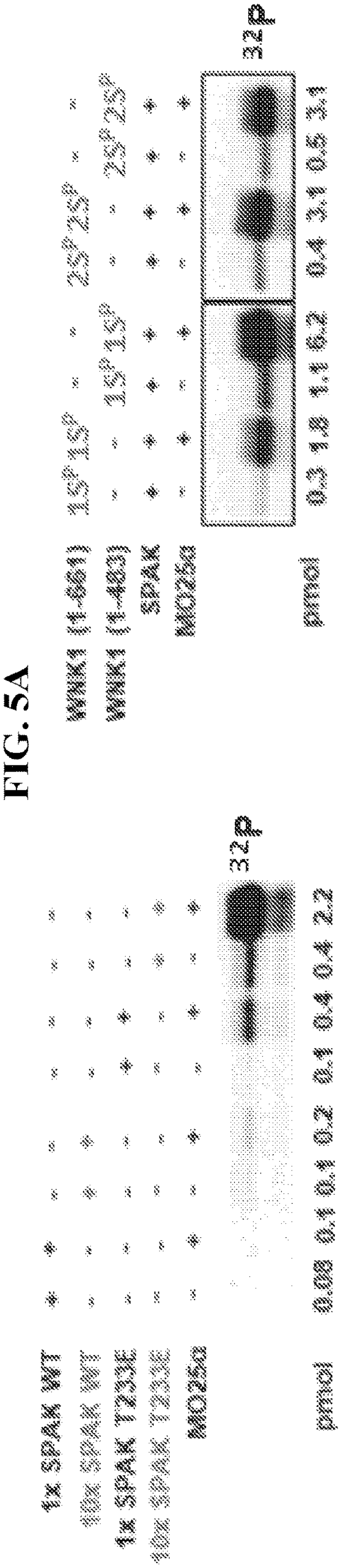
FIGS. 5A-5B illustrate the finding that Sep-activated WNK1 variants stimulate the most SPAK activity and is further enhanced by the regulatory protein MO25α.
Figure 5B:
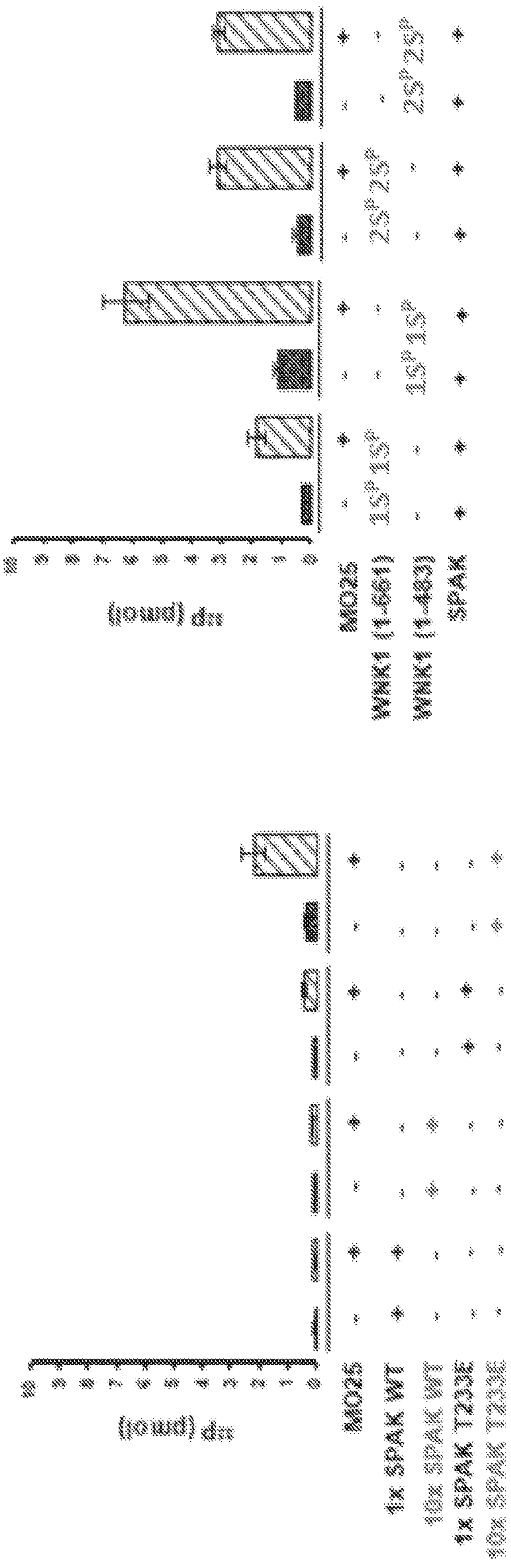
Figure 6A:
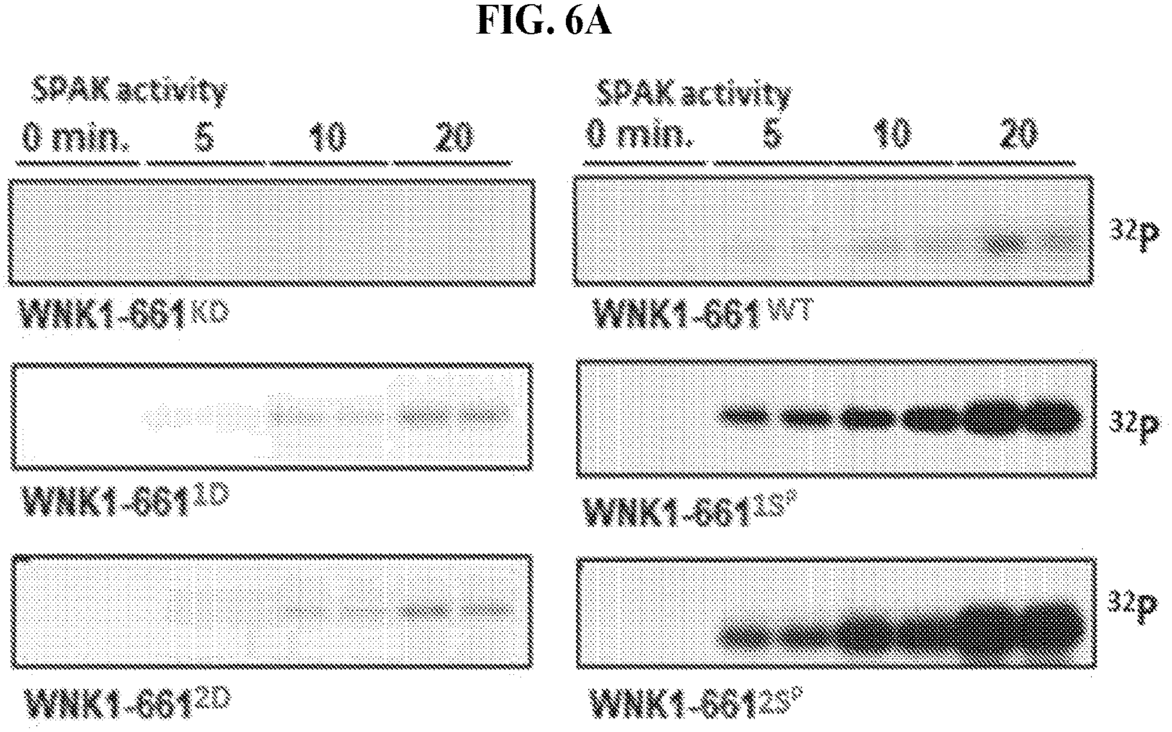
FIGS. 6A-6B illustrate the finding that Sep-activated WNK1 variants stimulate the most SPAK activity with or without the WNK1 AID. WNK1 variants (FIG. 6A) containing (1-661) or (FIG. 6B) lacking (1-483) the AID co-expressed with SPAK were reacted in vitro with MO25α, and NKCC1. In vitro kinase reactions were executed in intervals from 0-20 min. NKCC1 phosphorylation with $^{32}P$ was monitored by autoradiography.
Figure 6B:
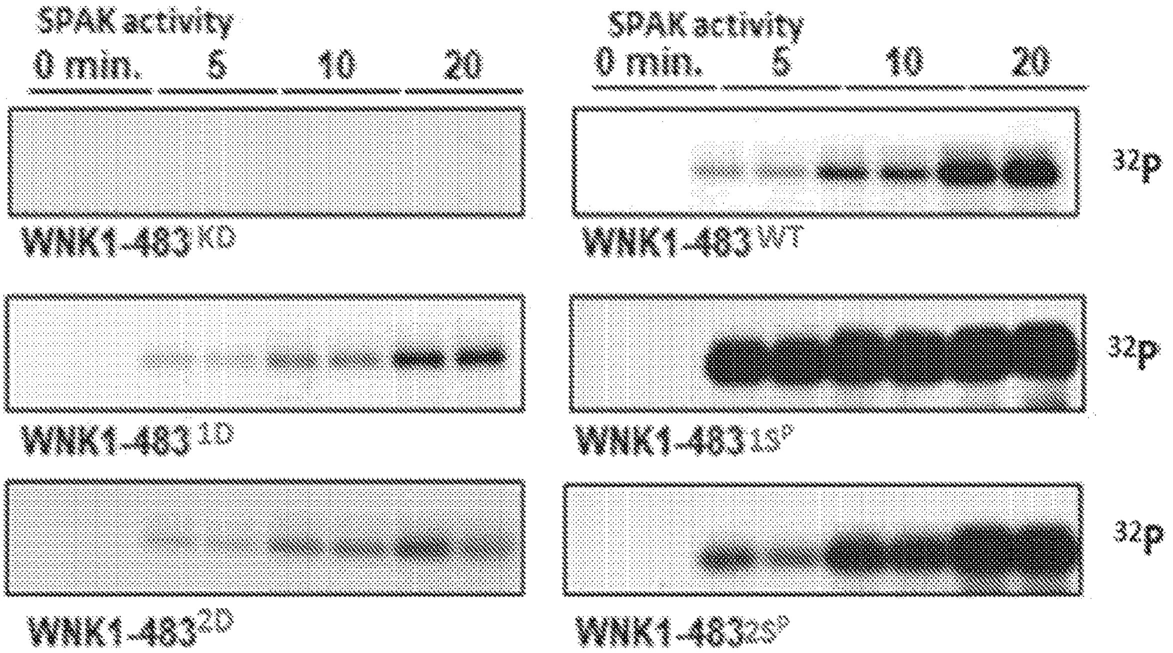

Since studies have used a glutamate substitution (T233E) to mimic SPAK phosphorylation and circumvent the need for WNK1 activation, in the present study one aims to more rigorously characterize the highly active, recombinant WNK-SPAK system by evaluating WNK1-activated SPAK with and without MO25α, a known enhancer of SPAK activity (Grimm, et al., 2012, J. Biol. Chem. 287:37673-37690). Unmodified SPAK expressed in bacteria had no detectable activity either with or without MO25α, while the phosphomimetic SPAK (T233E) possessed low activity with a small but reproducible enhancement in the presence of MO25α (FIGS. 5A-5B). In contrast to both unmodified and SPAK (T233E), each $S^P$WNK1-SPAK preparation was notably more active with substantially enhanced activity in the presence of MO25α (FIGS. 6A-6C). These experiments confirm that both phosphoserine at S382 ($1S^P$) and S378/S382 ($2S^P$) in the canonical activation loop of WNK1 is sufficient for WNK1 activation. To verify phosphoserine incorporation, the products of several of these reactions were examined by mass spectrometry and it was confirmed that SPAK was phosphorylated at its physiologically relevant positions (FIGS. 7A-7B). Taken together, these data demonstrate the ability to produce catalytically active human WNK1 kinase, which when co-expressed with SPAK, recapitulates native WNK-SPAK activation.

Example 2: Active $S^P$WNK1-SPAK Conforms to Known Substrates

Figure 8A:
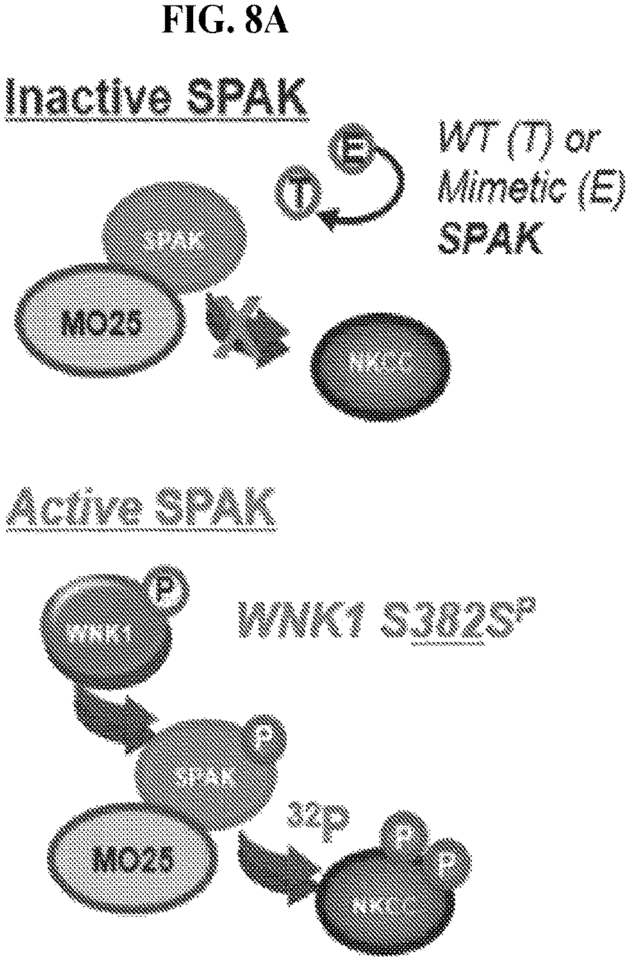
FIGS. 8A-8B illustrate the finding that WNK1 activated SPAK is highly active and recognizes and phosphorylates its target ion cotransporters by a specific SPAK kinase motif.
Figure 8B:
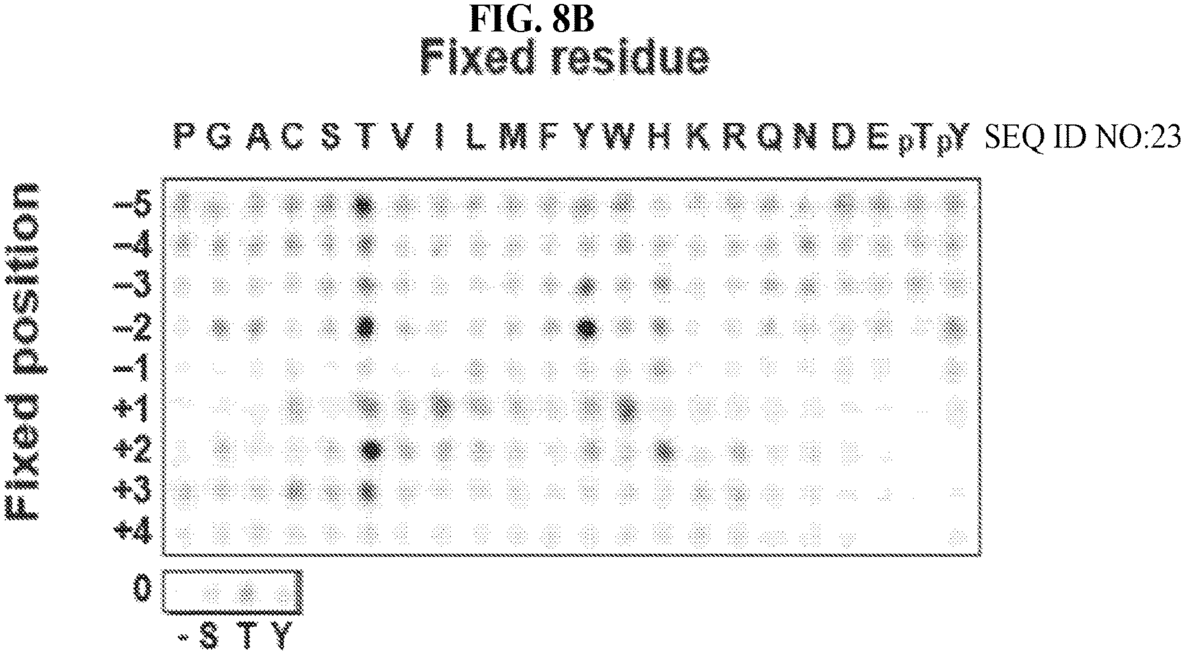

The ability to generate high yields of physiologically phosphorylated SPAK provided the opportunity to profile its phosphorylation site sequence preferences (FIG. 8A). To identify a SPAK kinase motif, a high-throughput in vitro kinase assay was performed using the published Positional Scanning Peptide Library (PSPL) (Hutti, et al., 2004, Nat Methods 1, 27-29). Quantified data from the PSPL (FIG. 8B) were used to generate a sequence logo that illustrates the amino acid preferences at each position relative to the phosphorylation site (FIG. 1D). Comparison of the results from the peptide screen to known phosphorylation sites on canonical substrates suggests strong preferences for tyrosine and histidine residues at the −3 and −2 positions, for hydrophobic residues at the +1 position, and for a Thr phospho-acceptor residue (FIG. 1E). This motif is distinct from that of another kinase in the STE20 kinase family, MST4, which has a strong preference for lysine and arginine residues at the +2, +3, and +4 positions. This data reveals differences in kinase specificity that may explain why MST4 does not activate the ion cotransporters despite belonging to the same STE20 kinase family. The SPAK kinase motif resulting from the screen showed strong preferences for residues that surround known substrate phosphorylation sites (FIG. 1E), a further indication that SPAK co-expressed with $S^{P}$WNK1 in *E. coli* produces a physiologically relevant kinase.

Figure 2A:
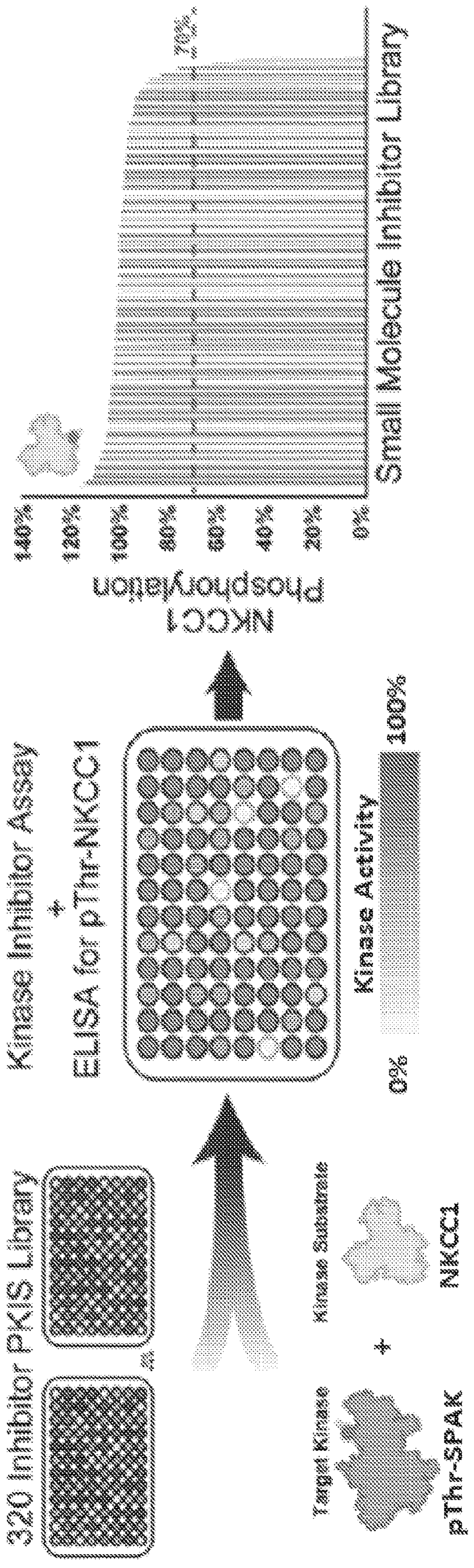
FIGS. 2A-2F illustrate the finding that small molecule screen against phospho-active SPAK yielded new SPAK kinase inhibitors.
Figure 2B:
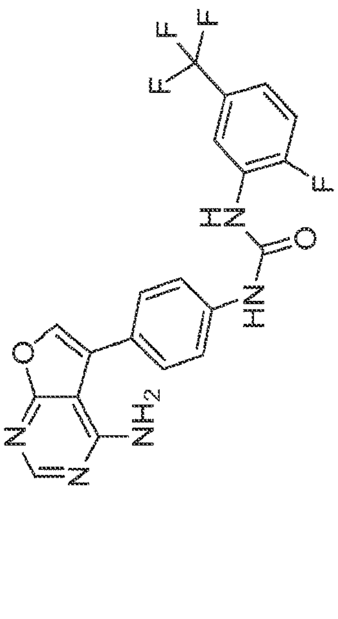
Figure 2C:
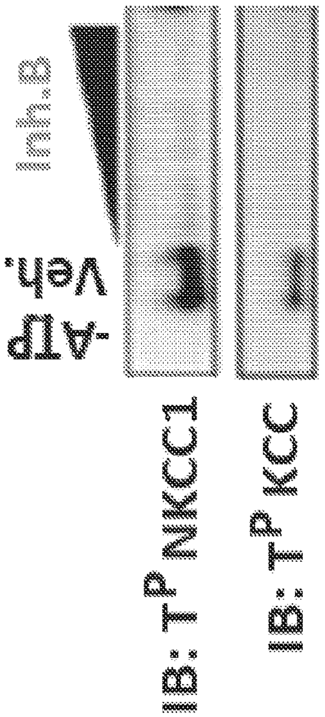

Example 3: Small Molecule Inhibitor ELISA Screen Identifies Potential SPAK Inhibitors The highly active SPAK preparations offered a unique and physiologically relevant approach to identify novel small molecule kinase inhibitors. Combining the $S^{P}$WNK1-SPAK with an ELISA-based assay to measure NKCC1 phosphorylation, a screen of 360 compounds from the GlaxoSmithKline (GSK) published protein kinase inhibitor set (PKIS-1) was performed to identify potential SPAK inhibitors (FIG. 2A). At least one compound that reduced NKCC1 phosphorylation at a concentration of 27 μM was identified (FIG. 2B); that compound was labelled as Inh.A or Inh.B (as obtained from different manufacturers). Inh.A/B was further evaluated for dose-dependent inhibition of both NKCC1 and potassium chloride cotransporter (KCC) phosphorylation (FIG. 2C).

Figure 2E:
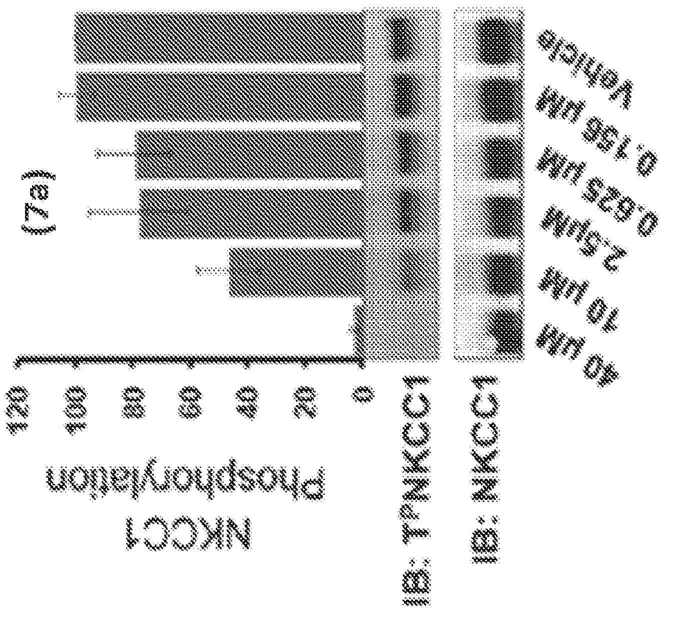
Figure 2D:
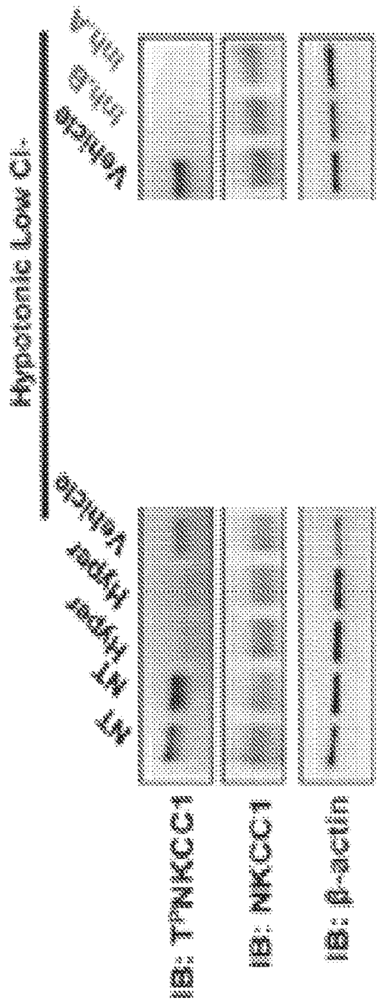
Figure 9:
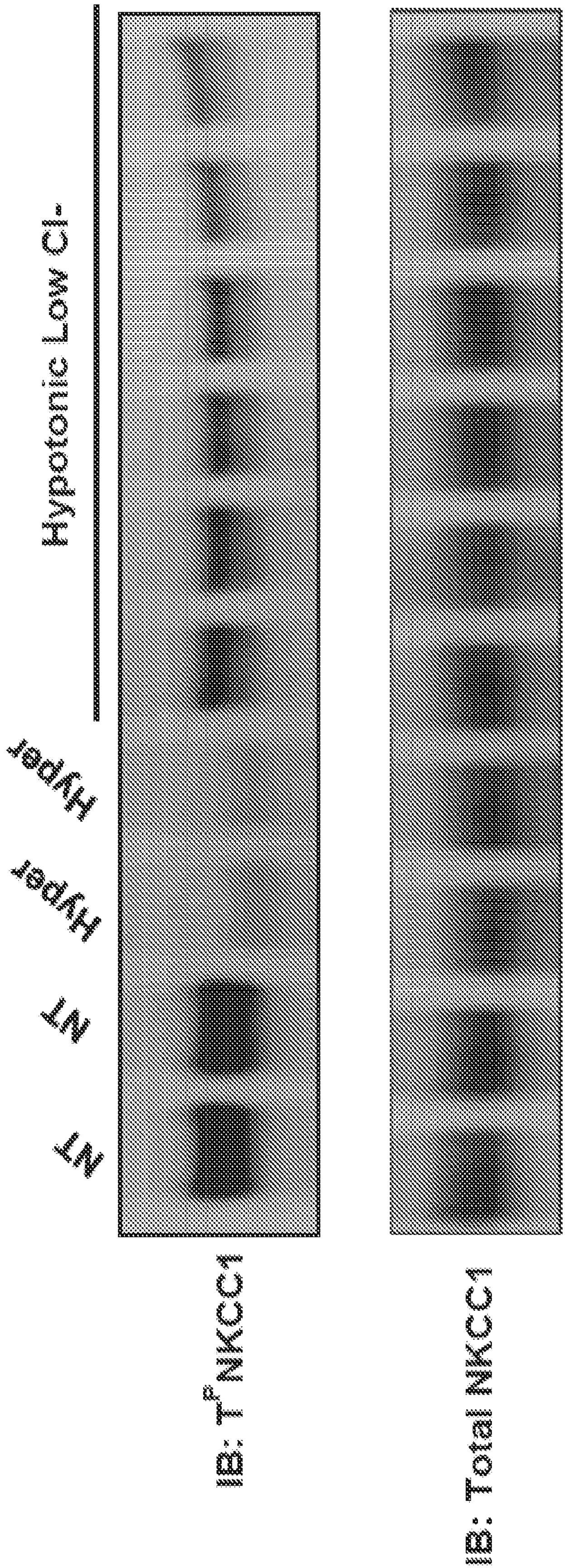
FIG. 9 comprises a control western blot observing modulation of NKCC1 signal under hyper- and hypotonic conditions in mDCT15 cells.
Figure 10A:
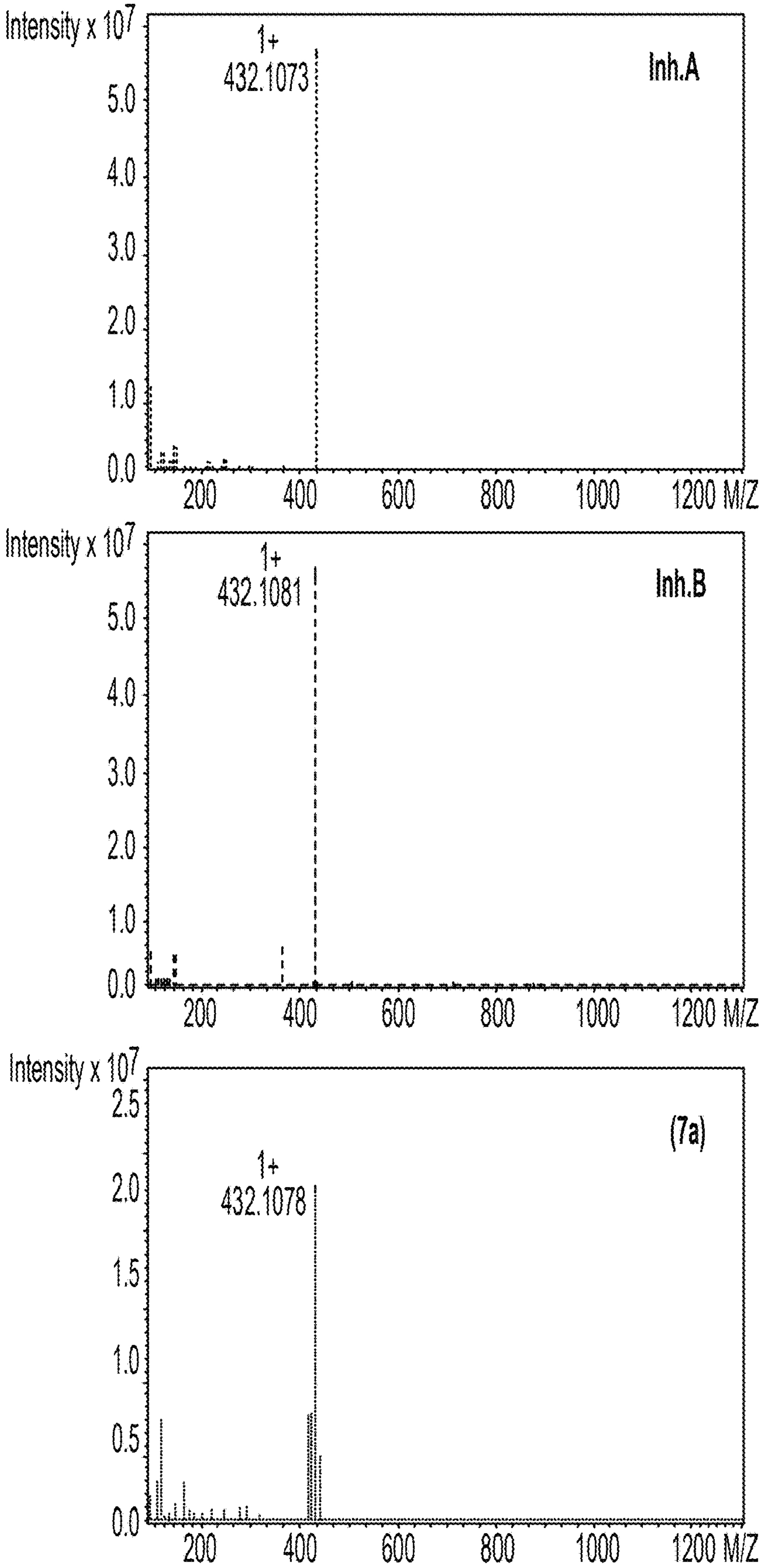
FIGS. 10A-10B illustrate mass of Inh.A/Inh.B and (7a) examined by FTICR MS and MS/MS.
Figure 10B:
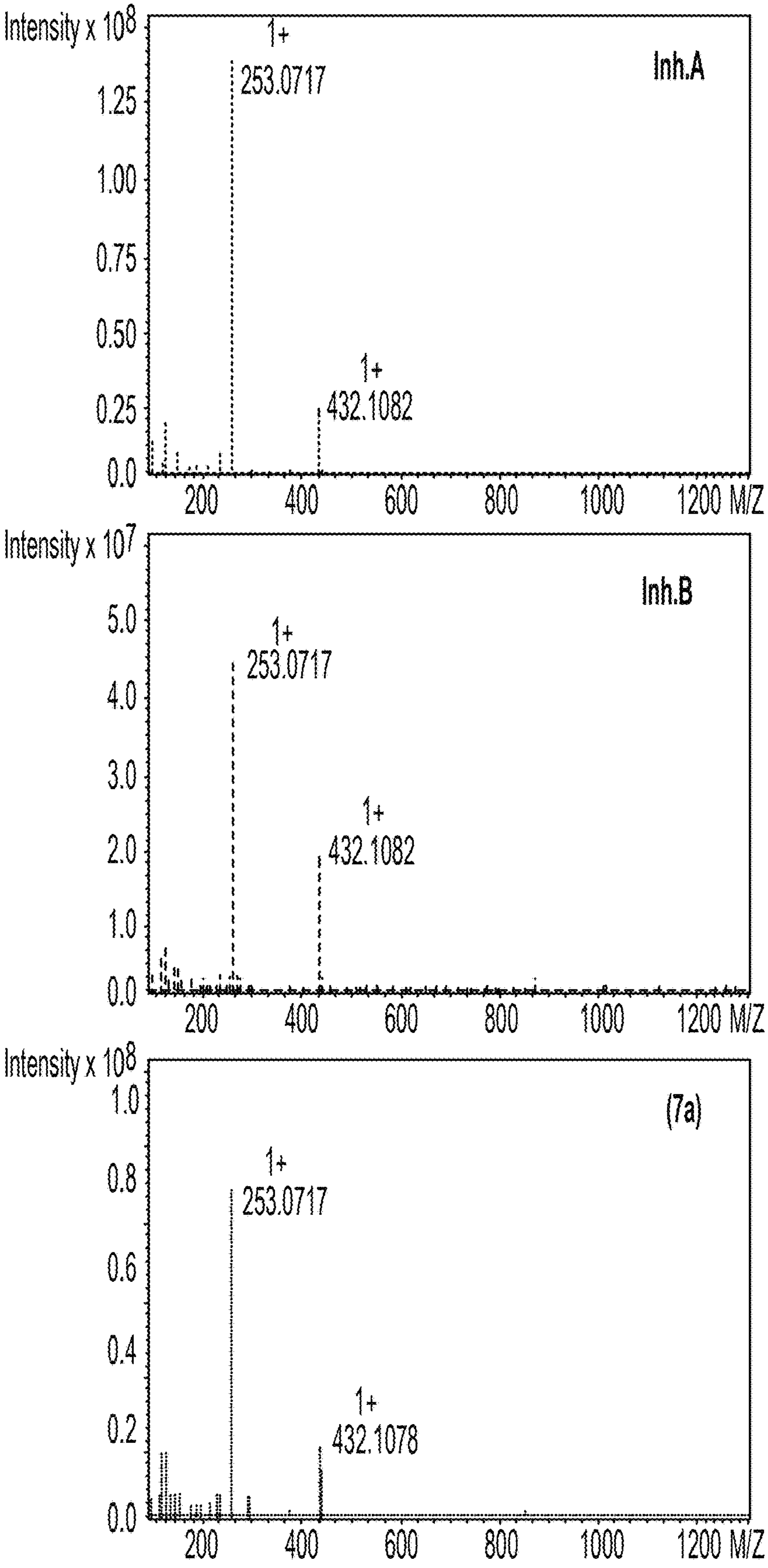
Figure 11:
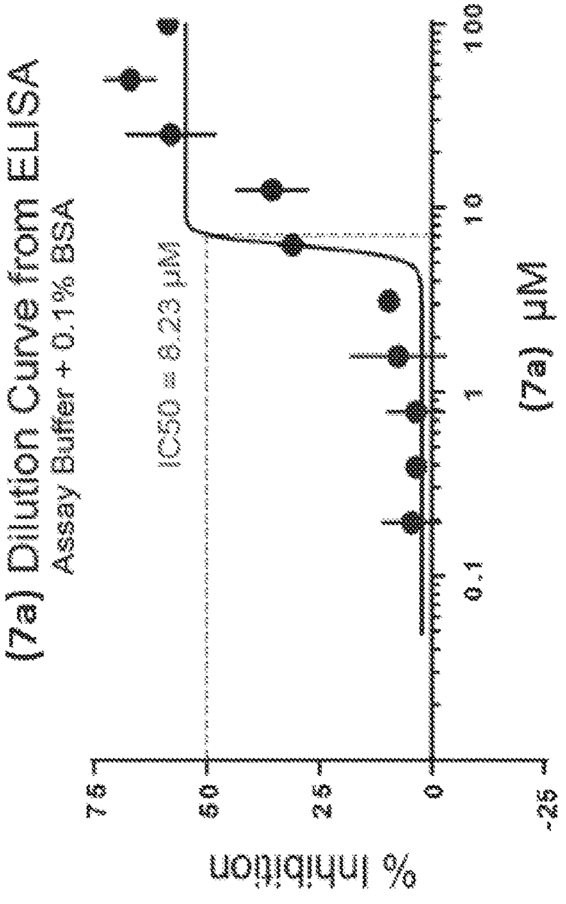
FIG. 11 illustrates $IC_{50}$ for (7a) determined using ELISA based assay at 10 μM ATP.

Hypo- and hyperosmotic conditions either activate or deactivate the WNK-SPAK-NKCC1 signaling cascade, respectively. The ability of these conditions to modulate the signaling cascade was evaluated in a mouse distal convoluted tubule cell line (mDCT15) previously demonstrated to exhibit osmolality dependent regulation of NKCC1 to establish the upper and lower limits of signal detection for the $T^{P}$NKCC1 immunoblot assay (FIG. 9). NKCC1 phosphorylation was monitored under hyper- and hypo-osmotic conditions to evaluate the degree of SPAK inhibition in the presence of the putative inhibitor compound (FIG. 2D). The vehicle controls showed a prominent $T^{P}$NKCC1 signal as expected, while cells treated with the compounds yielded inhibitory effects consistent with the in vitro kinase assay. Inh.B was further evaluated with a dilution series to determine the potency in the mDCT15 cells (FIG. 2E). Similar to the initial in vivo assay, inhibitor concentrations of 40 μM completely blocked NKCC1 phosphorylation. In dose response assays, these compounds had approximately 50% inhibition at 10 μM, and no inhibitory effect at concentrations below ~625 nM. As final validation, SPAK Inh.A was resynthesized and named (7a) and analyzed by FTICR MS/MS (FIG. 10). The $IC_{50}$ of (7a) was determined to be 8.23 μM at 10 μM ATP using the in vitro SPAK ELISA assay (FIG. 11).

Figure 12A:
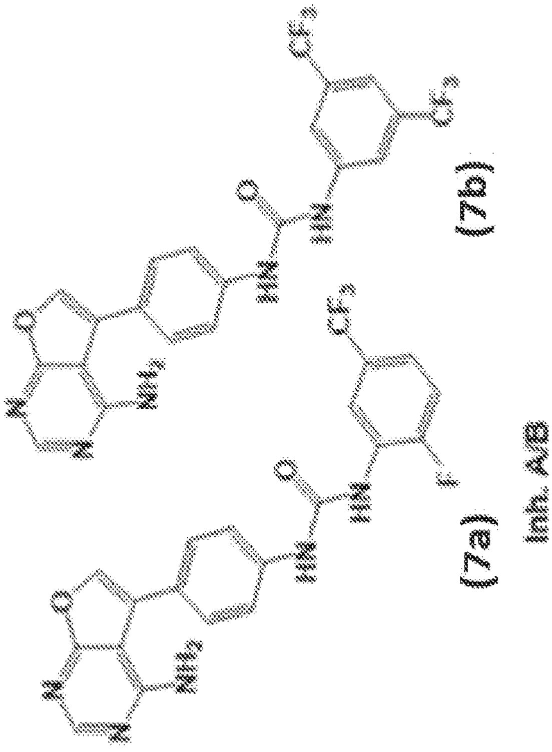
FIGS. 12A-12F illustrate the finding that (7a) depletes phosphorylated NKCC1 and reduces cell volume in mDCT15 cells.

The GSK PKIS library annotates (7a) and another compound (7b), as a potent VEGFR2/Tie-2 inhibitors. Interestingly (7b) did not emerge from the initial ELISA screen as a SPAK inhibitor despite being a similar chemotype (FIG. 12A). To compare (7a) with other VEGFR2/Tie-2 inhibitors, an in vitro kinase assay was performed comparing a dilution series of (7a), (7b), and commercially available VEGFR2/Tie-2 inhibitor, Cabozantinib malate XL-184 (FIGS. 12B-12E, 13). These data revealed that although (7a) and (7b) reportedly both inhibit VEGFR2/Tie-2 with similar potency, the two compounds do not have the same inhibitory effect on SPAK in vitro or in cell lines and suggest that VEGFR2/Tie-2 do not drive the robust physiological response from acute SPAK inhibition by (7a).

Figure 2F:
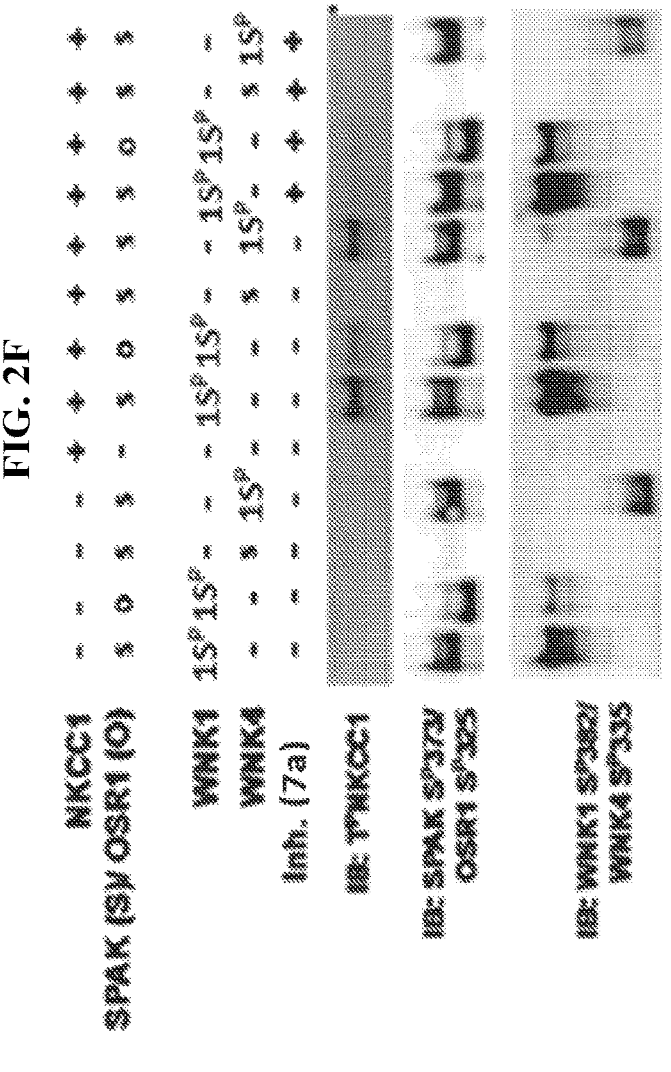

Since regulation of the signaling network that modulates cell volume involves other members of the WNK and SPAK kinase families, it was assessed if (7a) would also inhibit WNK1 activated OSR1 and WNK4 activated SPAK. The N-terminus of WNK4 encompassing the kinase domain is not catalytically active when expressed and purified from *E. coli*, indicating that unlike WNK1, this protein fragment of WNK4 cannot undergo autophosphorylation. Using the pSerOTS, $S^{P}$335 WNK4 (the equivalent to $S^{P}$382 WNK1) (1-447) with SPAK were co-expressed, as well as $S^{P}$382 WNK1 (1-661) with OSR1. Additionally, WT WNK4 was co-expressed with SPAK. In vitro kinase assays showed that $S^{P}$382 WNK1 activated OSR1 and $S^{P}$335 WNK4 activated SPAK both phosphorylate the NKCC1 substrate (FIG. 2F). WT WNK4 was unable to auto-phosphorylate and did not activate SPAK resulting in no detectable NKCC1 phosphorylation. The activity of these co-expressed constructs was also assessed in the presence of (7a), revealing that both SPAK and OSR1 were inhibited, which resulted in diminished NKCC1 phosphorylation (FIG. 2F). This establishes that the pSerOTS technique for authentic phosphorylated proteins uniquely produces multiple, active variants of the WNK/SPAK/OSR network. These results demonstrate that both WNK1 and WNK4 mediated SPAK/OSR1 activity is inhibited by (7a) in vitro and prompted testing the effect of this novel WNK/SPAK/OSR network inhibitor on cell migration.

Figure 3A:
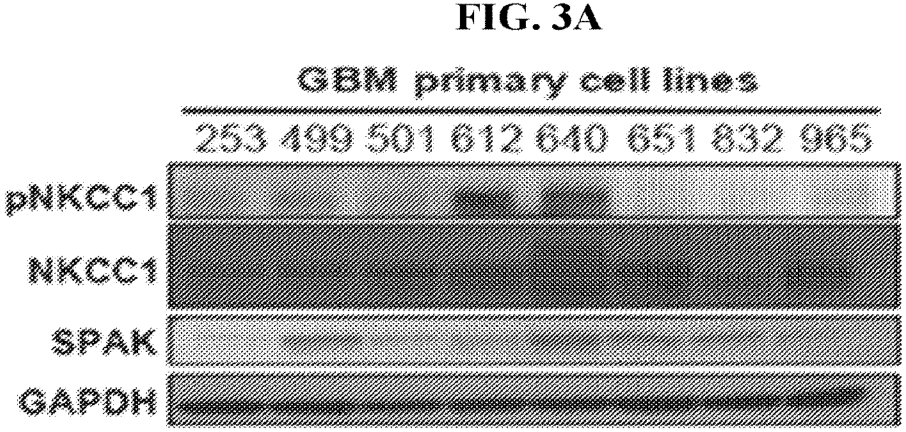
FIGS. 3A-3G illustrate the finding that (7a) retards glioblastoma (GB) cell speed and persistence.
Figure 3B:
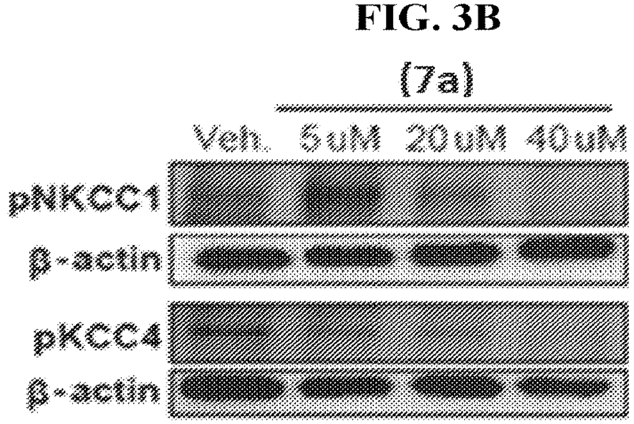
Figure 3C:
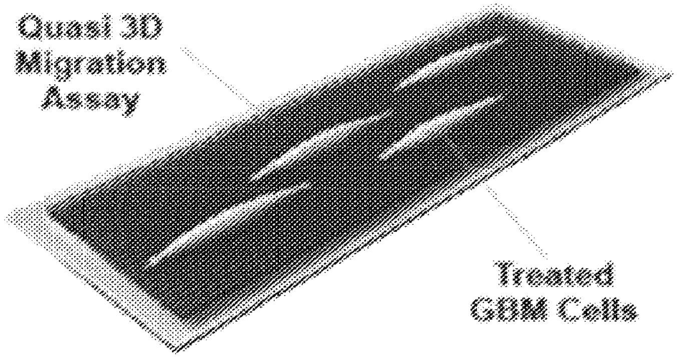
Figure 3D:
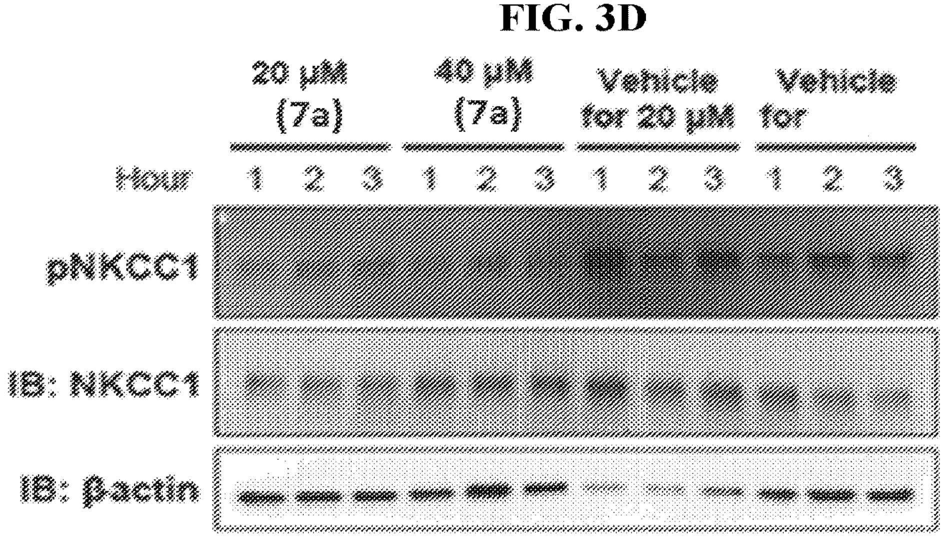
Figure 3E:
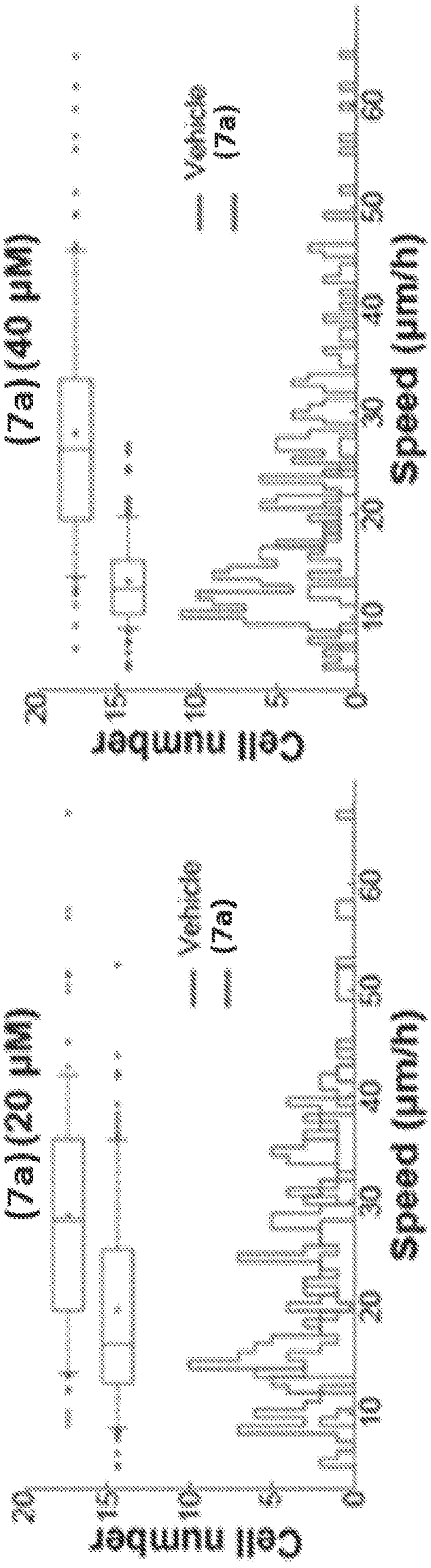
Figure 3G:
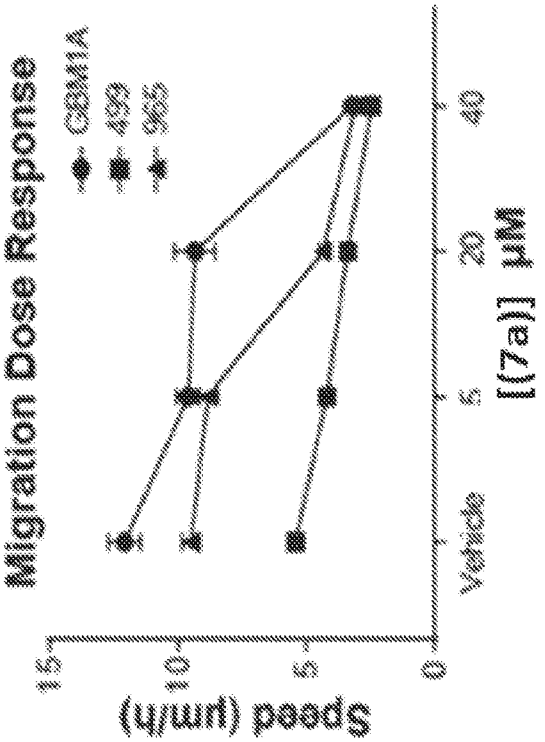
Figure 3F:
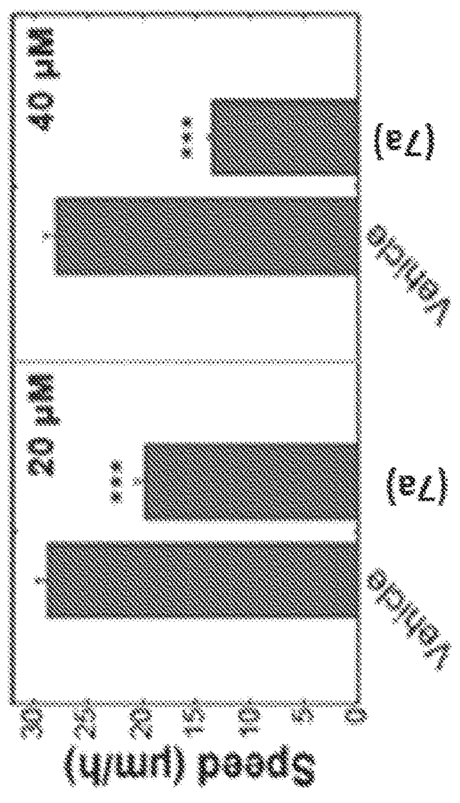

Example 4: (7a) Decreases Ion Co-Transporter Activity and Inhibits Migration in Glioblastoma Cells First, NKCC1 and SPAK expression was confirmed in a panel of patient derived primary GBM primary cell lines by immunoblot (FIG. 3A). SPAK pathway inhibition was tested by monitoring the physiological SPAK substrates NKCC1 and KCC4 and it was found that (7a) inhibited the SPAK-mediated phosphorylation of endogenous GBM499 NKCC1 and KCC4 in a dose dependent manner (FIG. 3B). To directly access the effect of (7a) on cell migration, an established quasi 3D migration assay employing a tissue mimetic nanopatterned substrate coated with extracellular matrix components was used. This artificial 3D surface recapitulates brain cancer cell migration and permits accurate, single cell quantification of mobility (FIG. 3C). Migration and polarization of cells cultured on this nanopatterned substrate mimics several aspects of actual migration in tissue and is a more accurate migration model than migration on flat surfaces (see, e.g., Doyle, et al., 2009, J. Cell. Biol. 184:481-490). Migration speed and persistence of cultured primary glioblastoma cell line GBM499 were assayed in the presence of 20 μM or 40 μM (7a) versus a vehicle control. Cell speed was monitored over a ten-hour time period after addition of either vehicle or (7a), and (7a) reduced the speed and persistence of the GBM cells over the vehicle control in a concentration dependent manner. Parallel time course assays were performed incubating the glioblastoma cell line with either (7a) or vehicle for 1, 2, or 3 hours and assessed NKCC1 phosphorylation via immunoblot (FIG. 3D). Both 20 μM and 40 μM (7a) doses led to a sustained ~3-fold reduction of NKCC1 phosphorylation compared to the corresponding vehicle controls. Assessment of individual cell speed values as a function of time revealed that at 20 μM (7a), the speed of most cells was retarded when compared to the vehicle control; while, at 40 μM (7a), all cells monitored had striking reduction in speed (FIG. 3E). Evaluation of the average cell speed under the same experimental conditions revealed that 20 μM and 40 μM (7a) reduced the average GBM cell migration speed by 1.45× and 2.07×, respectively (FIG. 3F). Similar results were obtained for GBM cell line GBM1A, an established model cell line (Galli, et al., 2004, Cancer Res. 64:7011-7021), and a second primary cell line GBM965 (FIGS. 3G, 14A-14C, and 15A-15C). These results indicate that (7a) is inhibiting its target SPAK/OSR1, reducing NKCC1 phosphorylation and ultimately decreasing GBM cell migration.

Figure 4A:
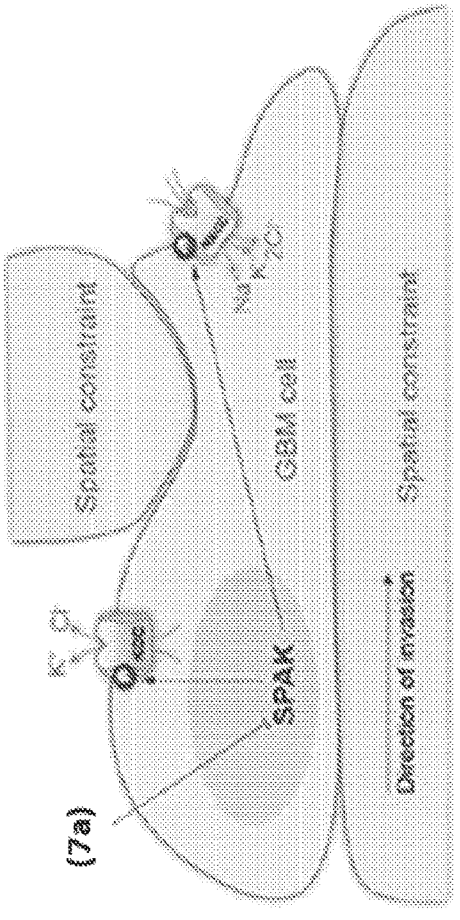
FIGS. 4A-4D illustrate the finding that (7a) inhibits GBM proliferation in vitro and in vivo.
Figure 4B:
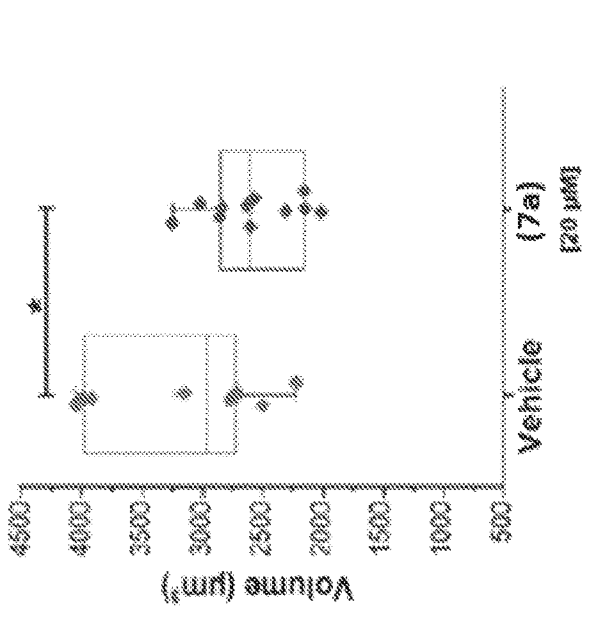
Figure 13:
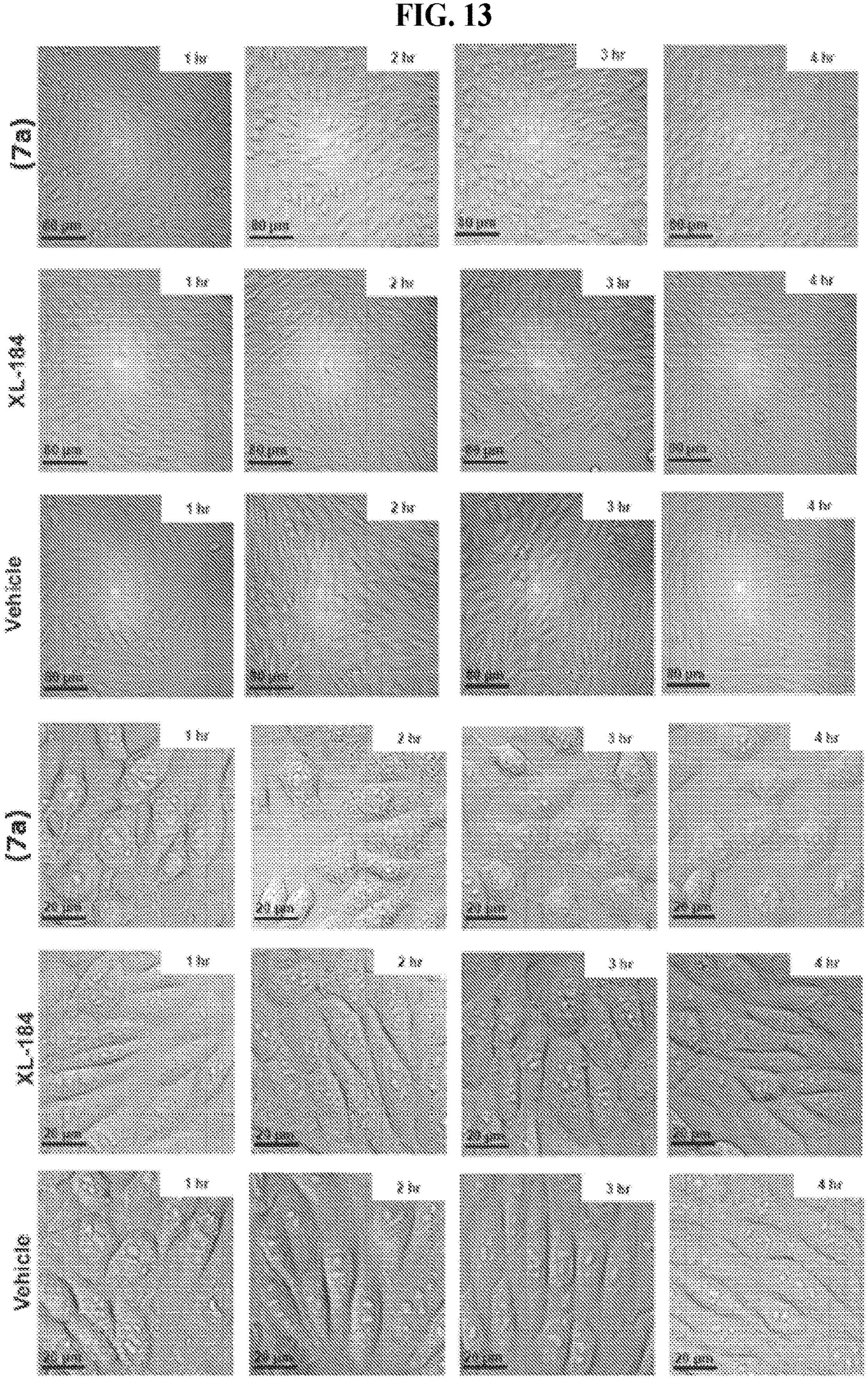
FIG. 13 comprises images of mDCT15 cells incubated with 40 μM (7a) 40 μM, Cabozantinib (XL-184), or equivalent volume of DMSO vehicle for a 1 hr, 2 hr, 3 hr, and 4 hr time course (partially shown in FIG. 12F). After incubation the cells were imaged using 20× and 80× bright field microscopy.
Figure 14A:
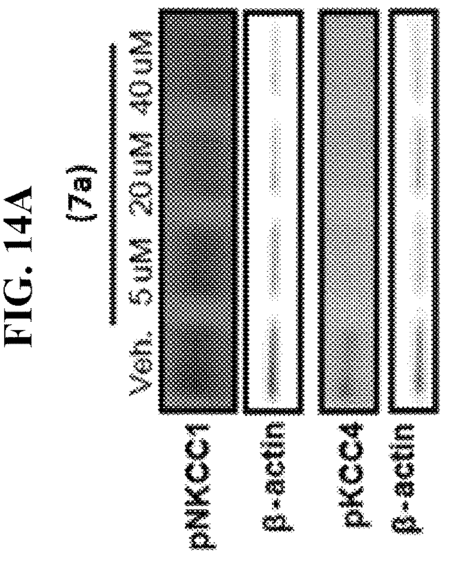
FIGS. 14A-14C illustrate the inhibitory effect of (7a) on primary GBM cell line GBM1A.
Figure 14B:
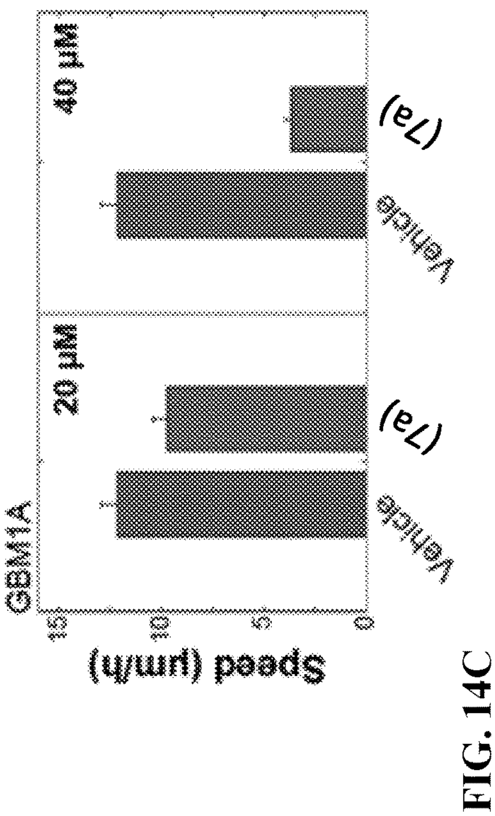
Figure 14C:
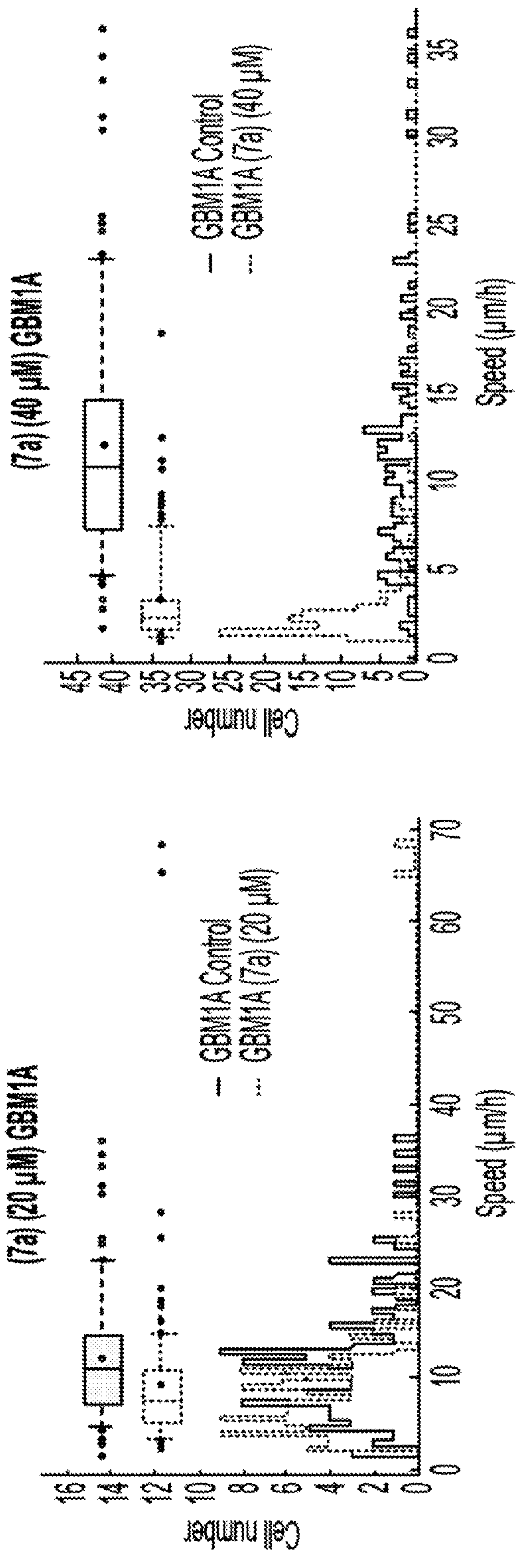
Figure 15A:
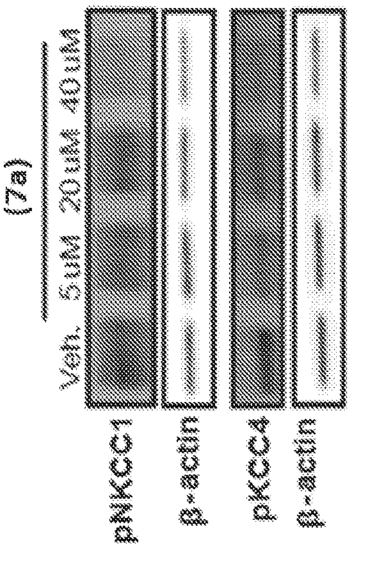
FIGS. 15A-15C illustrate inhibitory effect of (7a) on primary GBM cell line 965.
Figure 15B:
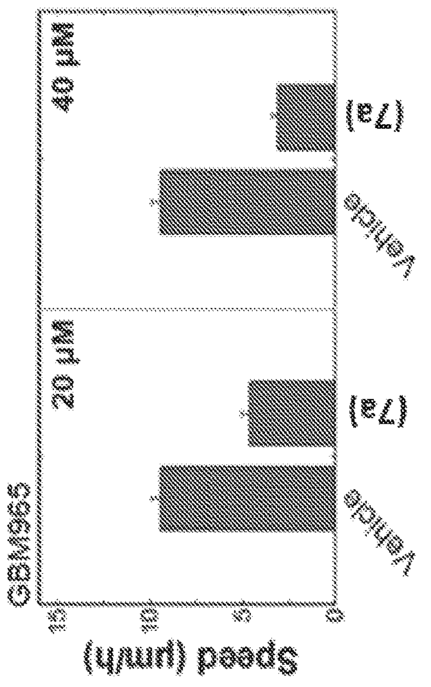
Figure 15C:
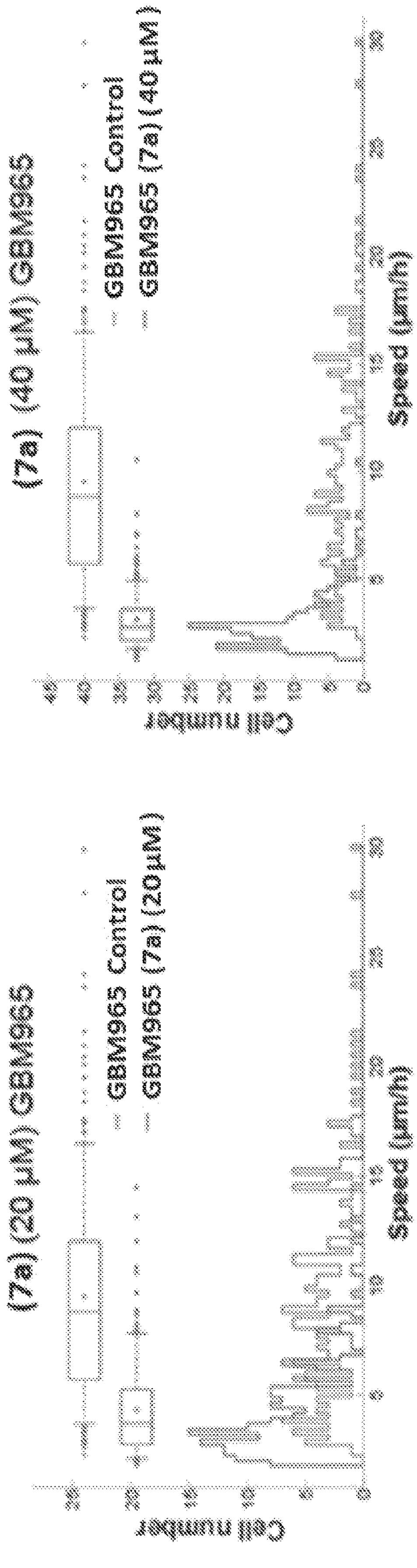

Example 5: (7a) Inhibits Glioblastoma Proliferation and Tumor Growth in Mice Upregulation of NKCC1 activity positively correlates with increased infiltration of migratory GBM cells and the histological grade and severity of gliomas. To migrate through the confined spaces of the brain parenchyma, GBM cells may rely on volume alterations facilitated by ion cotransporters, particularly NKCC1 and KCC (FIG. 4A). Pathways involving WNK and SPAK/OSR1 are the only known kinases responsible for directly activating the coordination of these ion co-transporters in vivo. Based on the time course inhibitor and migration assay results, we hypothesized that as the ion co-transporters become inactivated, cells can lose their ability to regulate volume and may undergo regulatory volume decrease thereby shrinking over time. To validate this hypothesis, phenotypic changes in GBM1A and mDCT15 cells incubated with (7a) or vehicle were evaluated by microscopic imaging (FIGS. 4B and 13). In both cases, (7a) caused a reduction in cell volume, while cells treated with the vehicle alone had no detectable change. Together, these data show (7a) mediated SPAK inhibition and concomitant reduction in NKCC1 and KCC phosphorylation leads to dysregulation of ion co-transporter activity and cell volume decrease that likely impact the migratory potential of GBM cells.

Figure 4C:
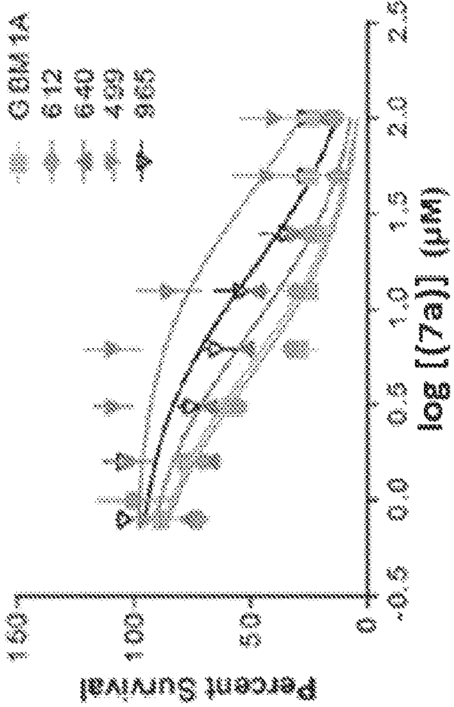
Figure 4D:
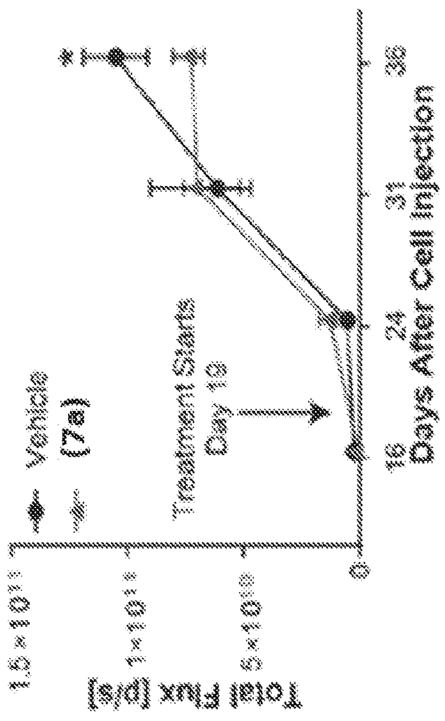
Figure 16:
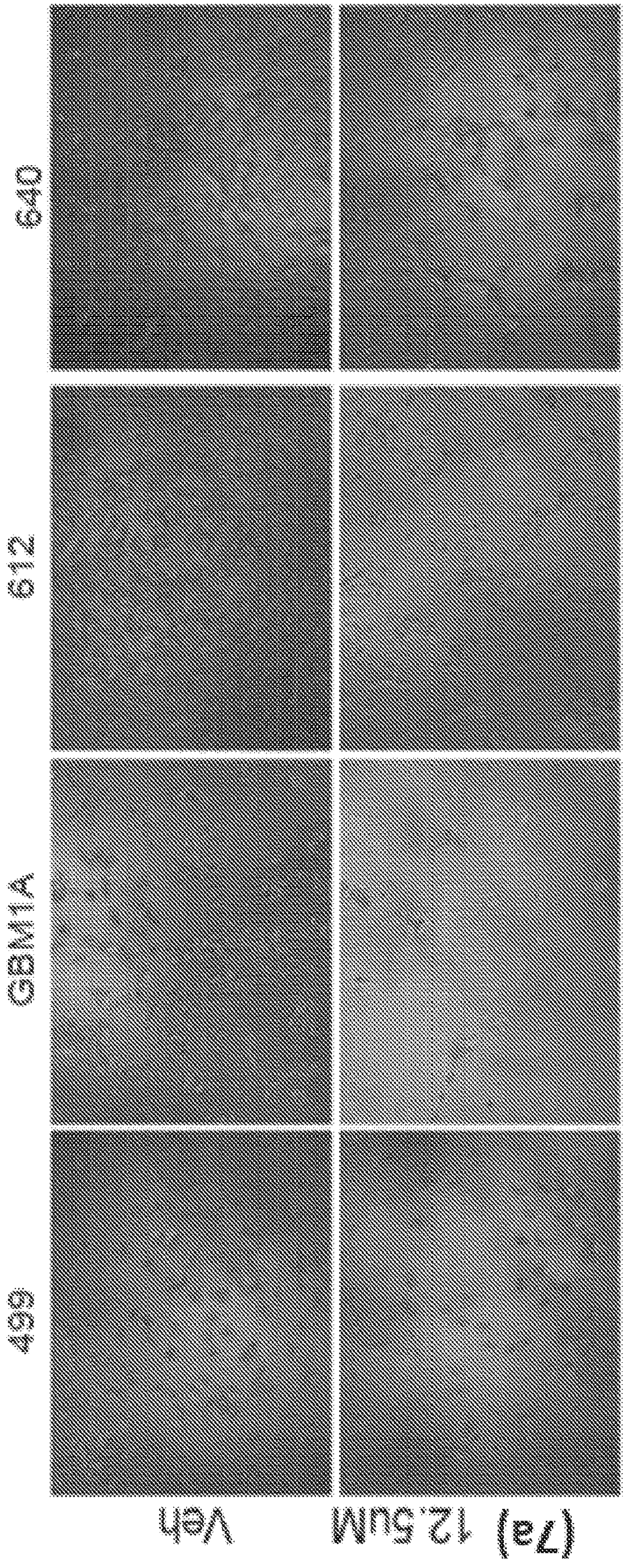
FIG. 16 comprises figures illustrating GBM primary cell lines incubated with 12. μM or equivalent volume of DMSO vehicle for a 1 hr. After incubation the cells were imaged using 20× bright field microscopy.
Figure 17:
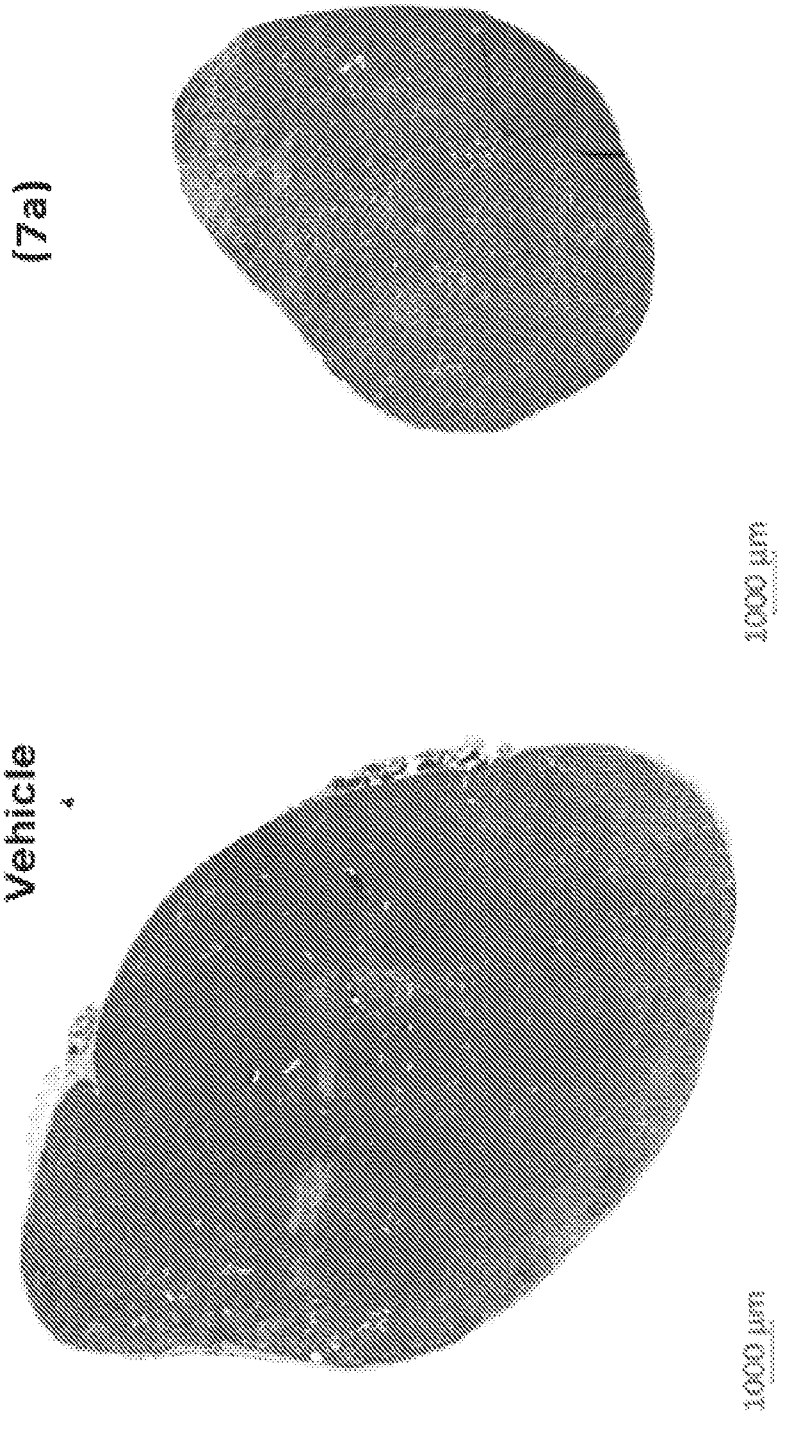
FIG. 17 comprises images illustrating H & E staining of GBM1A subcutaneous tumors treated with vehicle and (7a).
Figure 19:
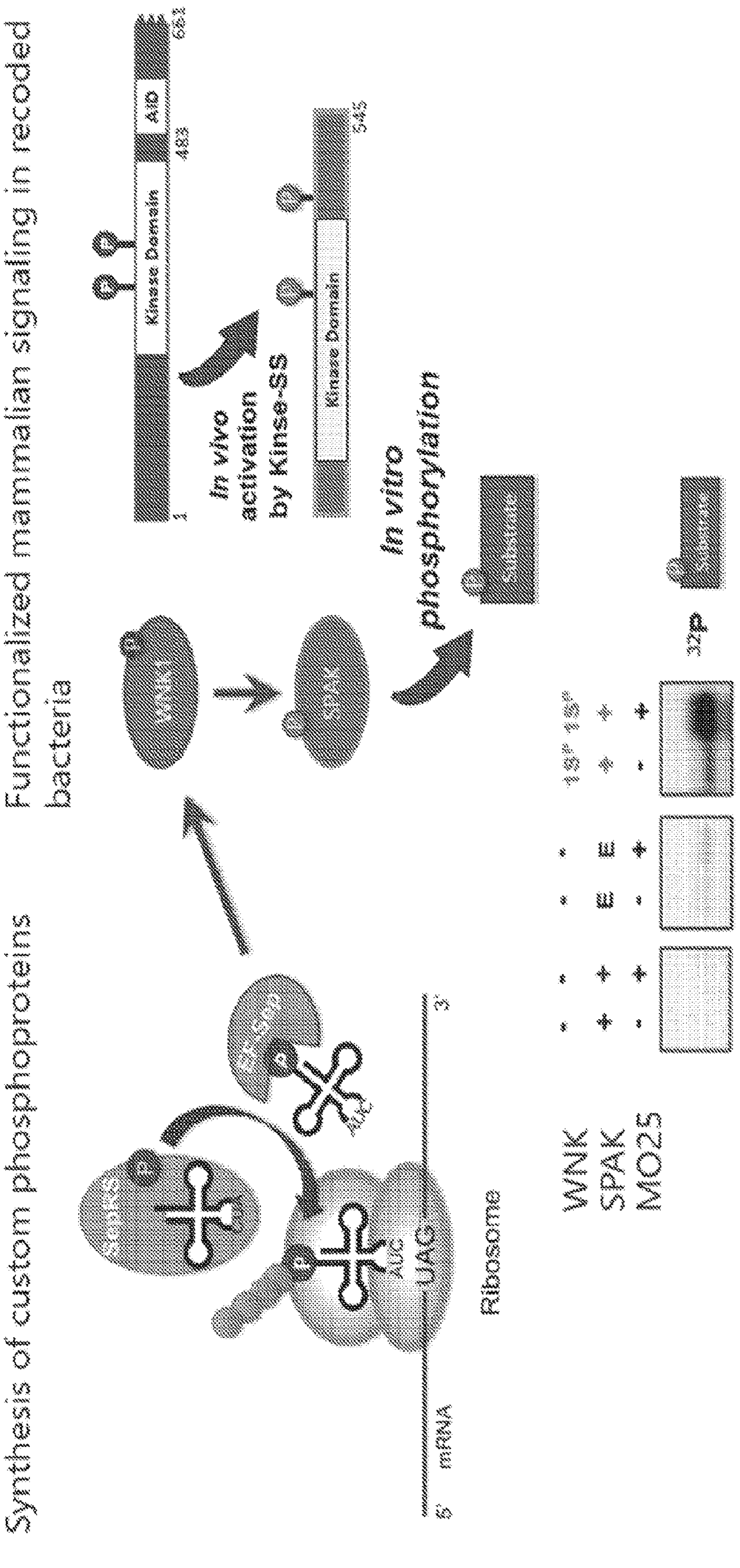
FIG. 19 illustrates a schematic view of phosphoprotein platform. SepRS charges phosphoserine onto $tRNA^{pSer}$, which directs phosphoserine incorporation at UAG stop codons. Human phosphoprotein can be produced in *E. coli* by placing TAG at any position in the recombinant DNA. The drawing on the left depicts genetically encoded phosphoserine in WNK1 yielding physiologically phospho-activated SPAK. and subsequent phosphorylation of NKCC1 on its physiologically relevant sites. The T-loop phosphorylation sites for each protein are highlighted in red. WNK1 variants containing (1-661) or lacking (1-483) the autoinhibitory domain (AID) were expressed with the Sep-OTS. The key active site residues S382 ($1S^{P}$), and S378/S382 ($2S^{P}$) of WNK1 were mutated to TAG for Sep incorporation.
Figure 20:
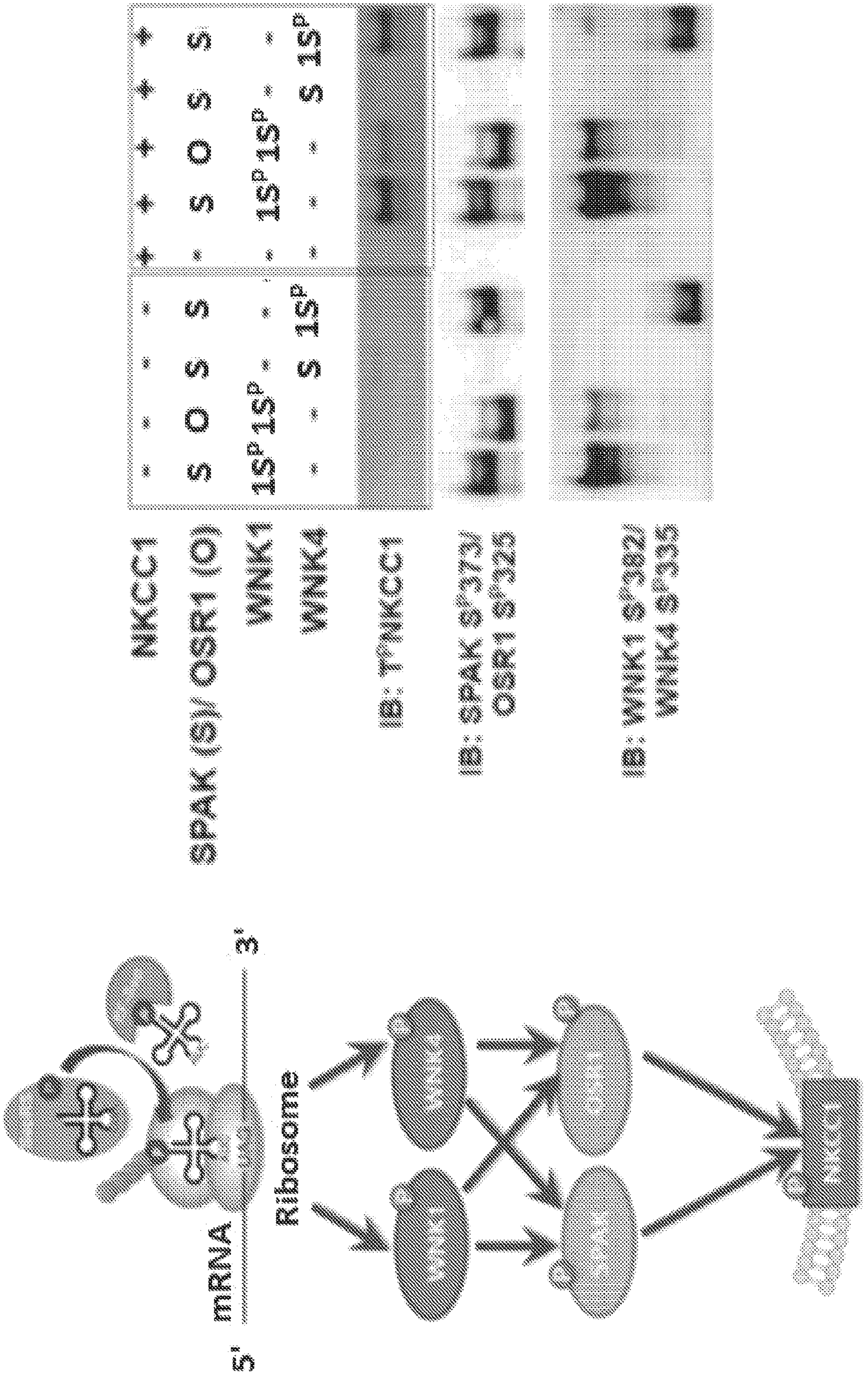
FIG. 20 illustrates the fact that phosphoprotein platform makes active WNK/SPAK/OSR combinations.

Because cell volume regulation through ion homeostasis is essential for cell division, the effect of SPAK inhibition on GBM proliferation was also analyzed. In vitro experiments with 5 GBM cell lines demonstrated a dose dependent inhibition of proliferation in response to (7a) (FIGS. 4C and 16). To validate the inhibitor-mediated decrease in GBM proliferation in vivo, xenografts of GBM1A were established subcutaneously in nude mice. Systemic delivery of (7a) through daily intraperitoneal injections at low doses (0.1 mg/kg) over the course of 17 days yielded significant inhibition of tumor growth, evaluated by Bioluminescence imaging (FIG. 4D). Tumor formation was confirmed by H & E staining (FIG. 17). Overall, these results demonstrate that (7a) can potentially be used to inhibit the GBM WNK/SPAK network in vivo.

Example 6: Sep-Activation Yields More Active Kinases than Phosphomimetic Activation at the Key Physiological Activation Sites Prior studies have used a phosphomimetic glutamate substitution (T233E) to mimic SPAK phosphorylation and circumvent the need for WNK1 activation since WNK mediated phosphorylation is required in vivo (Rafiqi, et al., 2010, EMBO molecular medicine 2:63-75). Furthermore, native SPAK systems form an important complex with MO25α, which enhances SPAK activity both in vitro and in vivo. A more rigorous characterization of the highly active, bacterial in vivo SPAK system was implemented by evaluating WNK1-activated SPAK±MO25α. WT SPAK expressed in bacteria is completely inactive with no activation by MO25α and T233E SPAK was only slightly active and showed small but reproducible enhancement in the presence of MO25α (FIGS. 6A-6B). In contrast to both WT and T233E SPAK, each $S^P$WNK1-SPAK preparation was notably more active at baseline and produced drastically more activity in the presence of MO25α (FIGS. 5A-5B). Unlike the $1S^P$WNK1-SPAK variants, the $2S^P$WNK1-SPAK variants had equivalent activity with or without their AID both in the absence or presence of MO25α. These data also show that the AID cannot inhibit WNK1 with proper (and physiologically relevant) phosphorylation at the canonical activation loop.

Previous studies have evaluated WNK1 kinase activities of the autophosphorylated or phosphomimetic WNK1 variants using the non-physiological substrate MBP, which consequently may have different activities when phosphorylating their physiological substrate, SPAK (Xu, et al., 2000, J. Biol. Chem. 275:16795-16801; Xu, et al., 2002, J. Biol. Chem. 277:48456-48462). Since all four $S^P$WNK1 co-expressed with SPAK stimulated a vastly higher degree of NKCC1 phosphorylation than WT or T233E SPAK alone in the presence of MO25α; this led us to the examination of the activity of SPAK co-expressed with other WNK1 variants. Co-expressed WNK1-SPAK variants were assessed with an in vitro SPAK/MO25α $^{32}P$ kinase assay to compare SPAK activation by various WNK1 constructs with and without their AID (FIGS. 6A-6B). KD WNK1 with or without its AID does not undergo autophosphorylation, and as expected had no distinguishable NKCC1 phosphorylation; thus, indicating that KD WNK1 was unable to activate the SPAK/MO25α complex. Despite WT WNK1's ability to undergo autophosphorylation the variant containing the AID had minimal activity and was unable to generate a highly active SPAK/MO25α complex. In contrast, without the AID, WT WNK1 had nearly 1.5× more activity; further validating the AID prevents autophosphorylation and indicates that constructs containing their AID limit our ability to use this mechanism to generate active kinases. Similarly, both 1D and 2D WNK1 showed minimal kinase activity with the AID, and gained slight activity without it. Although the phosphomimetic WNK1 variants gained function without their AID, they still had less activity when compared to WT without the AID, confirming previous reports, which showed phosphomimetic WNK1 variants had less activity than autophosphorylated WT WNK1. Both $1S^P$ and $2S^P$ WNK1 produced a highly active SPAK/MO25α complex as evident by the level of NKCC1 phosphorylation. Furthermore, 1 $S^P$ WNK1 gained substantial activation without the AID indicating the AID still modulated the activation of the second $S^P$WNK1 site through inhibiting autophosphorylation. In comparison, the $2S^P$ WNK1 variants showed similar levels of increased kinase activity with or without the AID. These data further confirmed that the AID does not inhibit WNK1 with proper (and physiologically relevant) phosphorylation at both key activation residues within the canonical activation loop.

Example 7

Figure 12B:
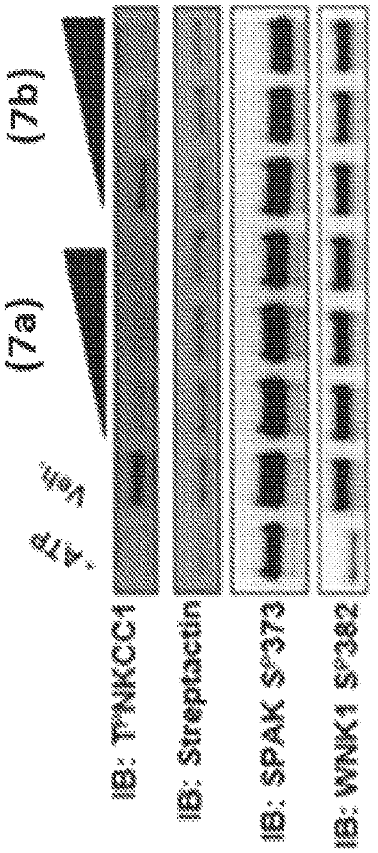
Figure 12F:
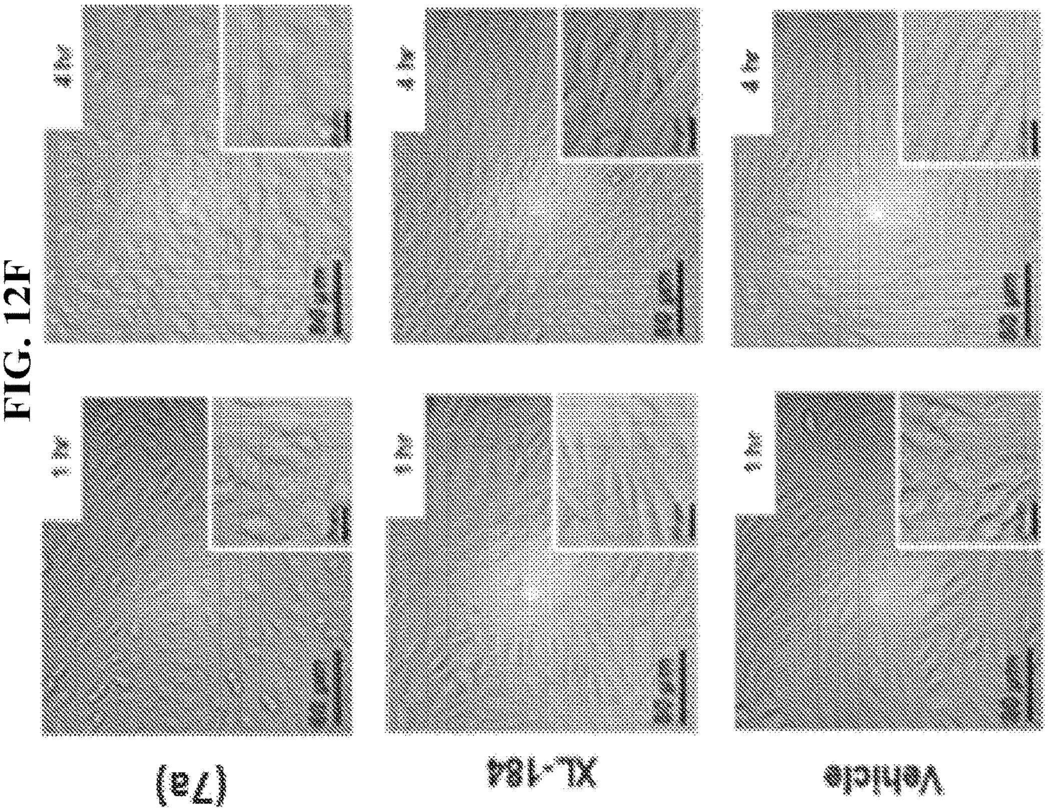
Figure 12C:
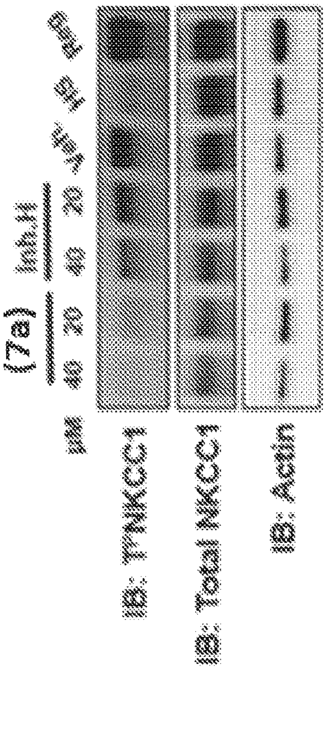
Figure 12D:
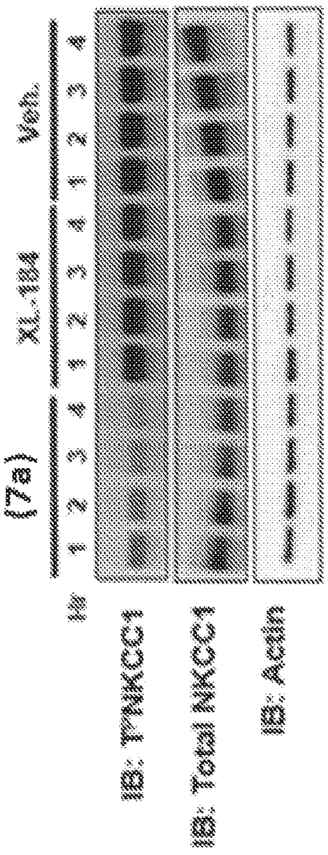
Figure 12E:
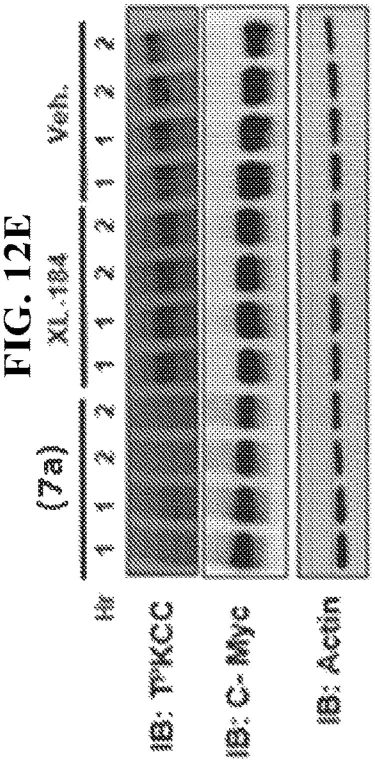

The GSK PKIS library, contained another compound with the same chemotype as (7a) that also had the same reported potency for VEGFR2/Tie-2; however, this compound (7b) did not emerge from the initial ELISA screen as a potential hit for SPAK (FIG. 12A). To validate that (7b) did not inhibit SPAK, an in vitro kinase assay was performed comparing a dilution series of (7a) and (7b) (FIG. 12B). These data revealed that although (7a) and (7b) reportedly both inhibit VEGFR2/Tie-2 with similar potency, the two compounds do not have the same inhibitory effect on SPAK. Additionally, both (7a) and (7b) effects on NKCC1 phosphorylation in the mDCT15 cell line were also examined at two different concentrations (FIG. 12C). (7a) caused an almost complete reduction in NKCC1 phosphorylation at both concentrations tested; however, although both the signal at both 40 μM and 20 μM (7b) for NKCC1 phosphorylation was reduced in comparison to the vehicle control, it was clear that (7b) did not inhibit SPAK to the same extent as (7a). This suggested that VEGFR2 or Tie-2 were not causal for the reduction in NKCC1 phosphorylation. To further establish that VEGFR2 or Tie-2 were not causing the reduction in NKCC1 phosphorylation, (7a) was compared to a drastically more potent commercially available VEGFR2/Tie-2 inhibitor, Cabozantinib malate XL-184 (FIGS. 12D-12E). Based on the known physiology of the ion co-transporters role in maintaining ion homeostasis, in certain embodiments upon inhibiting SPAK phosphorylation of the ion co-transporters decreases over time without the need of any upstream hyper or hypo-osmotic triggers. Indeed, over a span of 4 hrs, 40 μM of (7a) caused a noticeable reduction in NKCC1 phosphorylation; however, at 40 μM (6 fold higher than its known $pIC_{50}$ for VEGFR2) XL-184 had no discernable effect on NKCC1 phosphorylation. Again indicating that although (7a) has a higher reported potency for VEGFR2/Tie-2, these proteins are not responsible for the reduction in the ion co-transporter phosphorylation. Moreover, pathways involving WNK and SPAK/OSR1 are the only known kinases responsible for directly activating the ion co-transporters, which further exemplifies that the reduction observed in NKCC1 phosphorylation is a SPAK/OSR1 dependent phenomenon. Without wishing to be limited by any theory, based on the time course incubation results, as the ion co-transporters become inactivated the cells will lose their ability to volume regulate and should undergo regulatory volume decrease and shrink overtime. The mDCT15 cells was evaluated by microscopic imaging after incubation with (7a), XL-184, or Vehicle over a four-hour time course (FIGS. 12F and 13). These results showed that (7a) indeed caused a phenotypic change resulting in cell volume decrease in these cells, while neither XL-184 nor Vehicle had any detectable change over the time monitored. These data show (7a) mediated SPAK inhibition results in the reduction of NKCC1 phosphorylation and cell volume decrease phenotypic changes as anticipated.

Example 8: Small Molecule Inhibitors of SPAK

Figures 21, 22A, 22B, 22C, 22D:
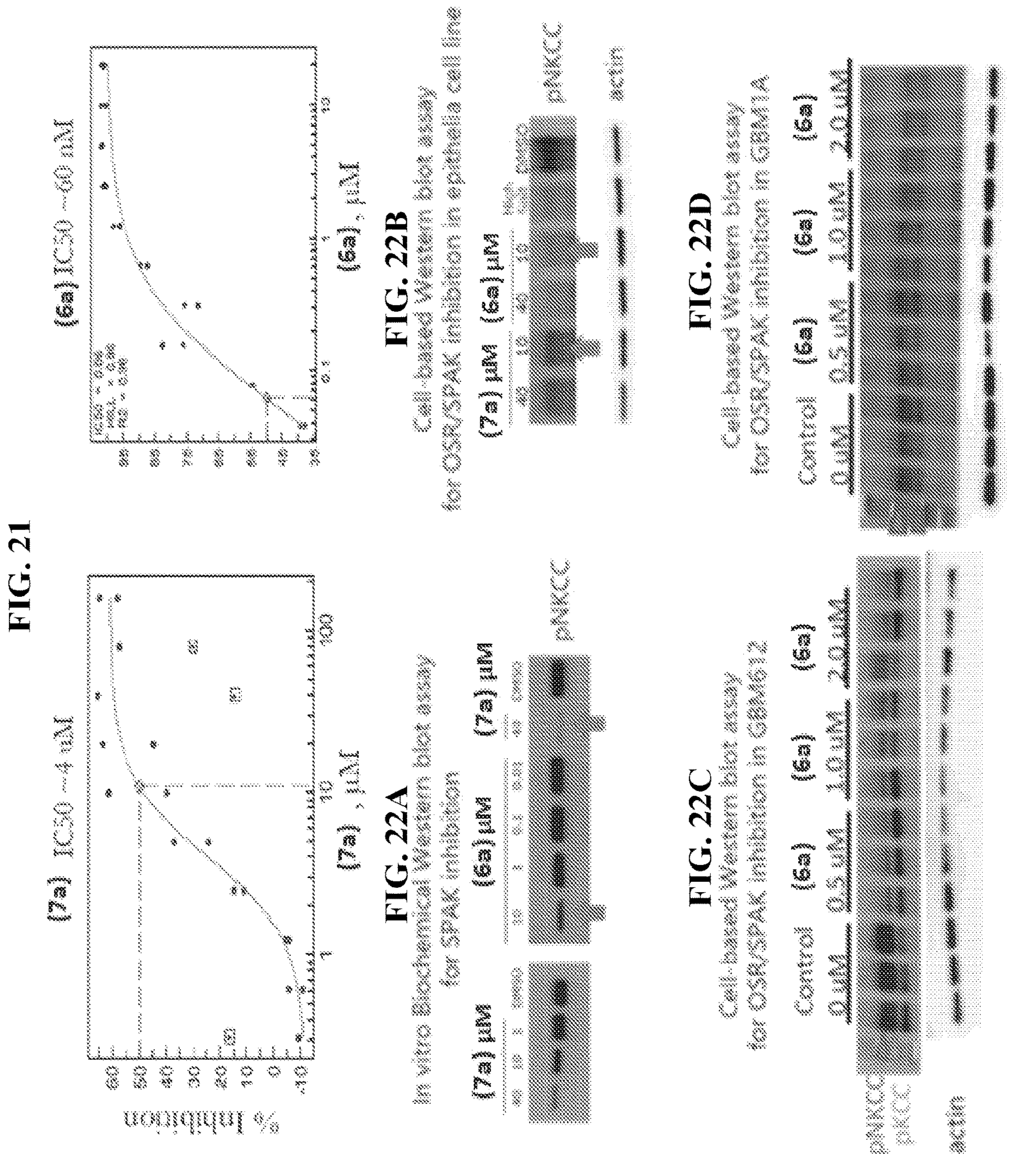
FIG. 21 illustrates $IC_{50}$ profiles for (7a) and (6a).
FIGS. 22A-22D illustrate in vitro validation of screen results.
Figure 23A:
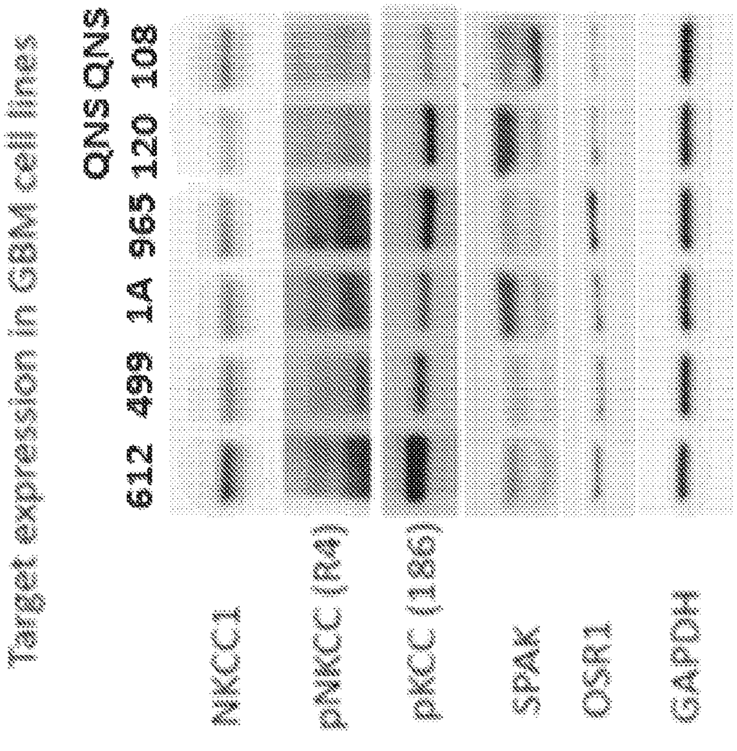
FIGS. 23A-23B illustrate SPAK/NKCC/KCC pathway and inhibition in primary human GBM cells.
Figure 23B:
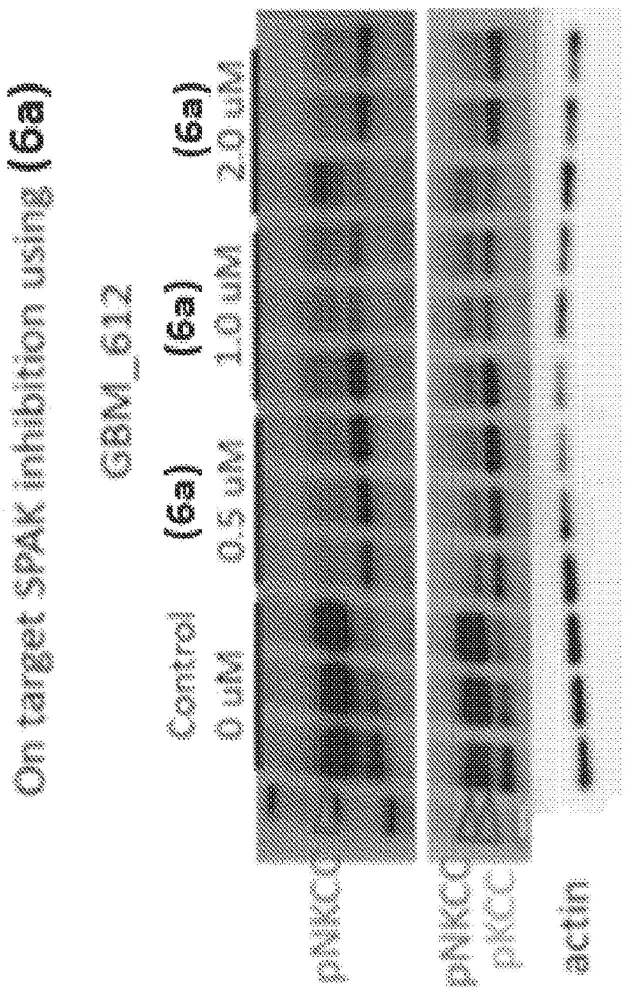

The screening platform described elsewhere herein allowed for the identification of compound (6a) as small molecule SPAK inhibitor, with an in vitro $IC_{50}$ of about 60 nM (FIG. 21). Cell based assays indicated that (6a) (as well as (7a)) indeed has on-target SPAK activity (FIGS. 22A-22D, 23A-23B, and 25). (6a) was shown to be a potent inhibitor of cancer cell migration and cancer cell proliferation.

(6a)

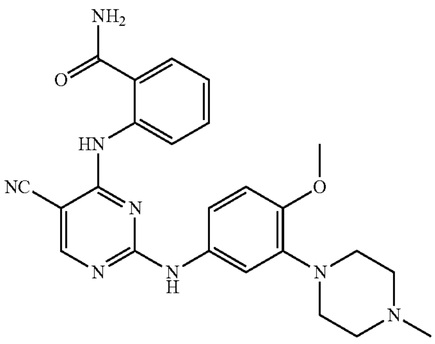

(6a) had already been described in the literature as being an Aurora kinase inhibitor (see for example WO2008092049A1, which is incorporated herein by reference in its entirety). However, the synthesis described in WO2008092049A1 did not yield (6a) cleanly, but rather proved to provide a mixture of inseparable positional isomers. In fact, the synthesis of (6a) described in WO2008092049A1 was extremely challenging and ambiguous: the isomers produced by that synthetic route cannot be distinguished unambiguously by NMR or other spectroscopic methods, and it is unclear that the reported compound and synthesis are accurate.

Figure 24:
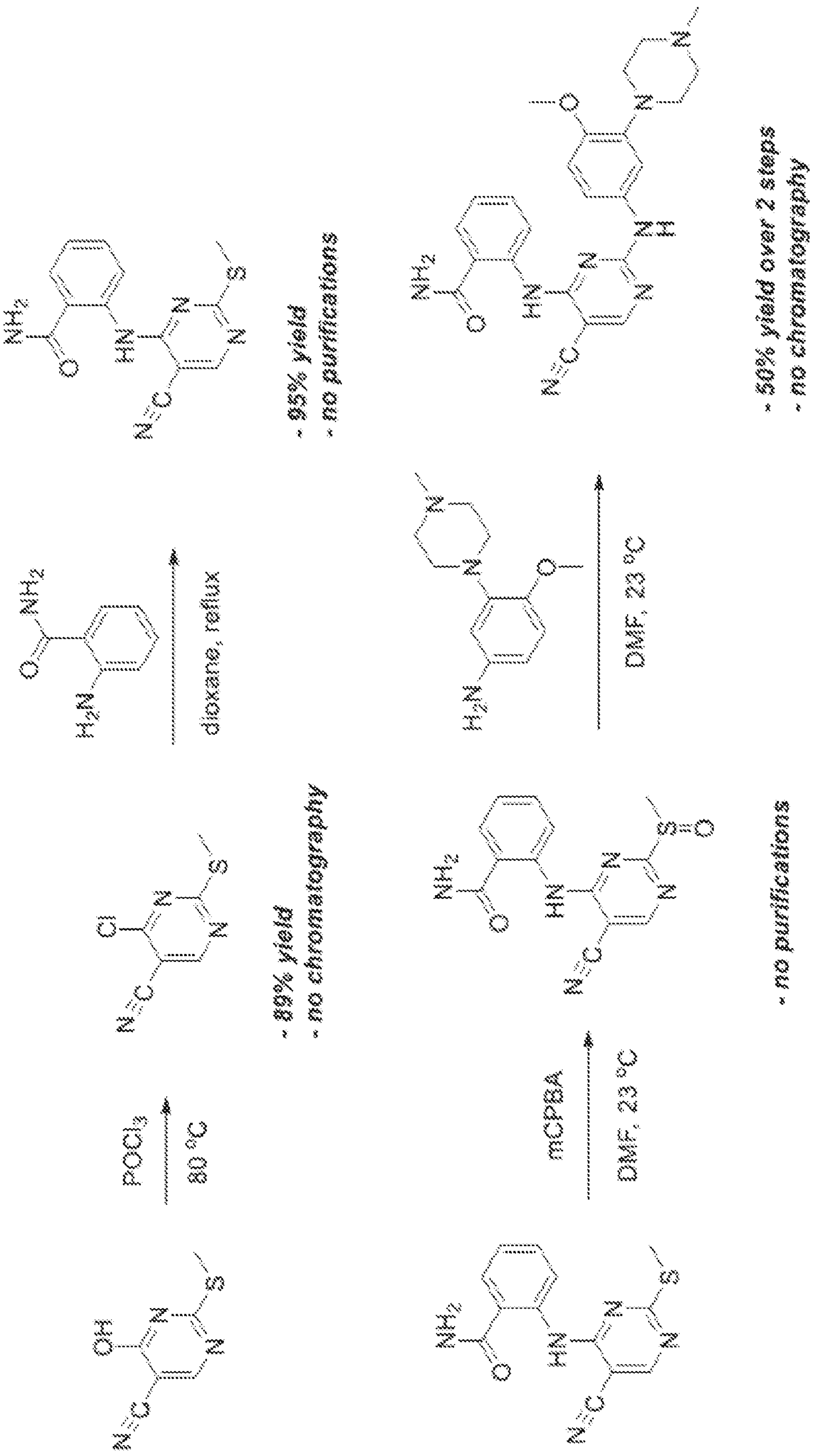
FIG. 24 illustrates a non-limiting chemical synthesis route for (6a) and analogues thereof.
Figure 25:
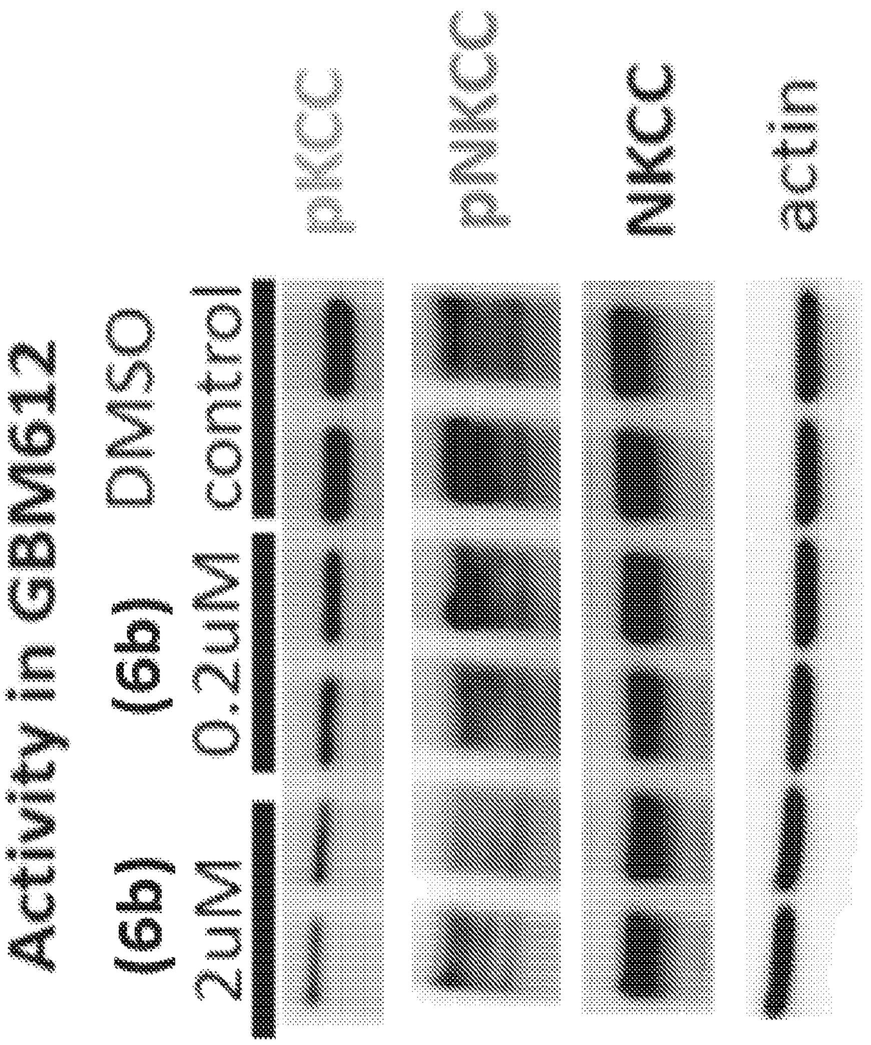
FIG. 25 comprises a section of a Western blot showing on-target activity in GBM612 cells.
Figure 25:
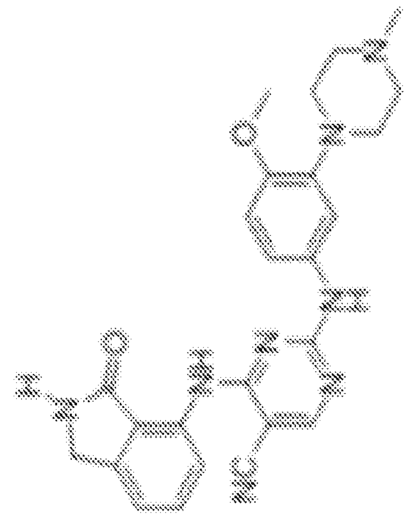

In response to this situation, the present disclosure provides a novel synthesis of (6a) and analogues thereof. the exemplified synthesis provides only the desired isomer, which structure follows unambiguously from the synthetic route. Thus, unlike the teachings of the WO2008092049A1, the synthetic route of the disclosure (exemplified in FIG. 24) does not afford any unknown and undesirable isomer. Following this synthetic route, several active analogues of (6a) (6b), (6c), (6d), (6e), (6f), and (6g) were generated (Table 1). (6b), (6d), (6e), and (6f) showed measurable SPAK inhibition.

Figure 26:
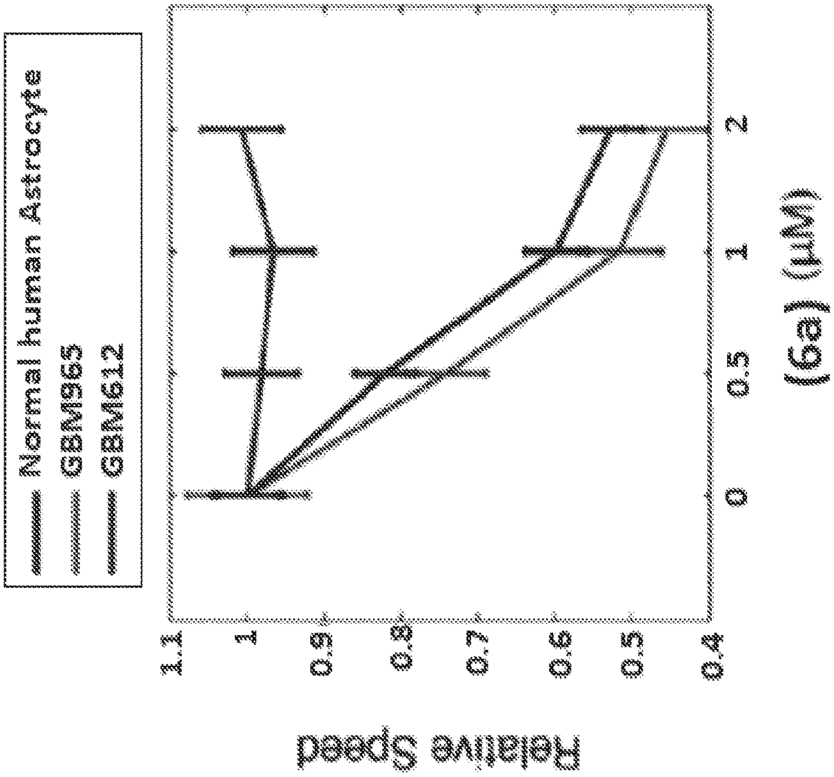
FIG. 26 illustrates the finding that primary GBM experience reduced migration in response to (7a) & (6a). Note that (6a) is not active on primary human astrocytes.
Figure 26:
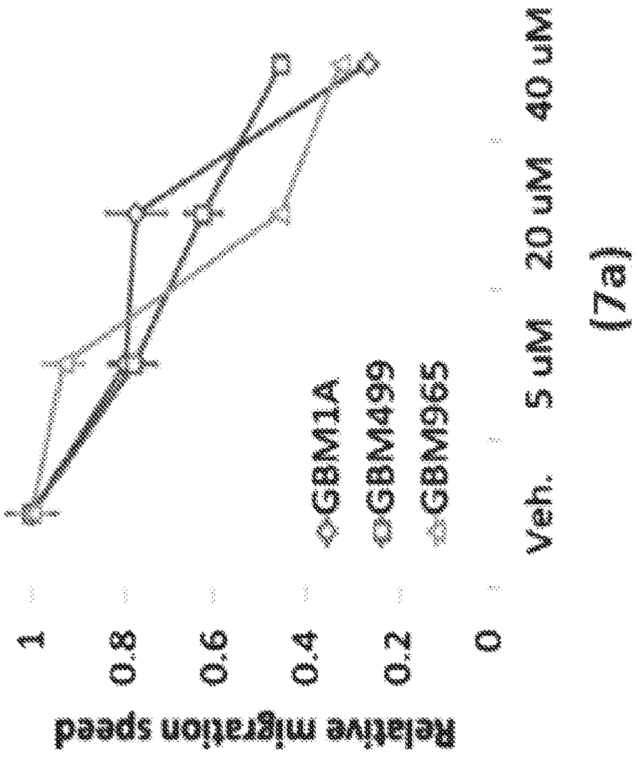
Figure 27:
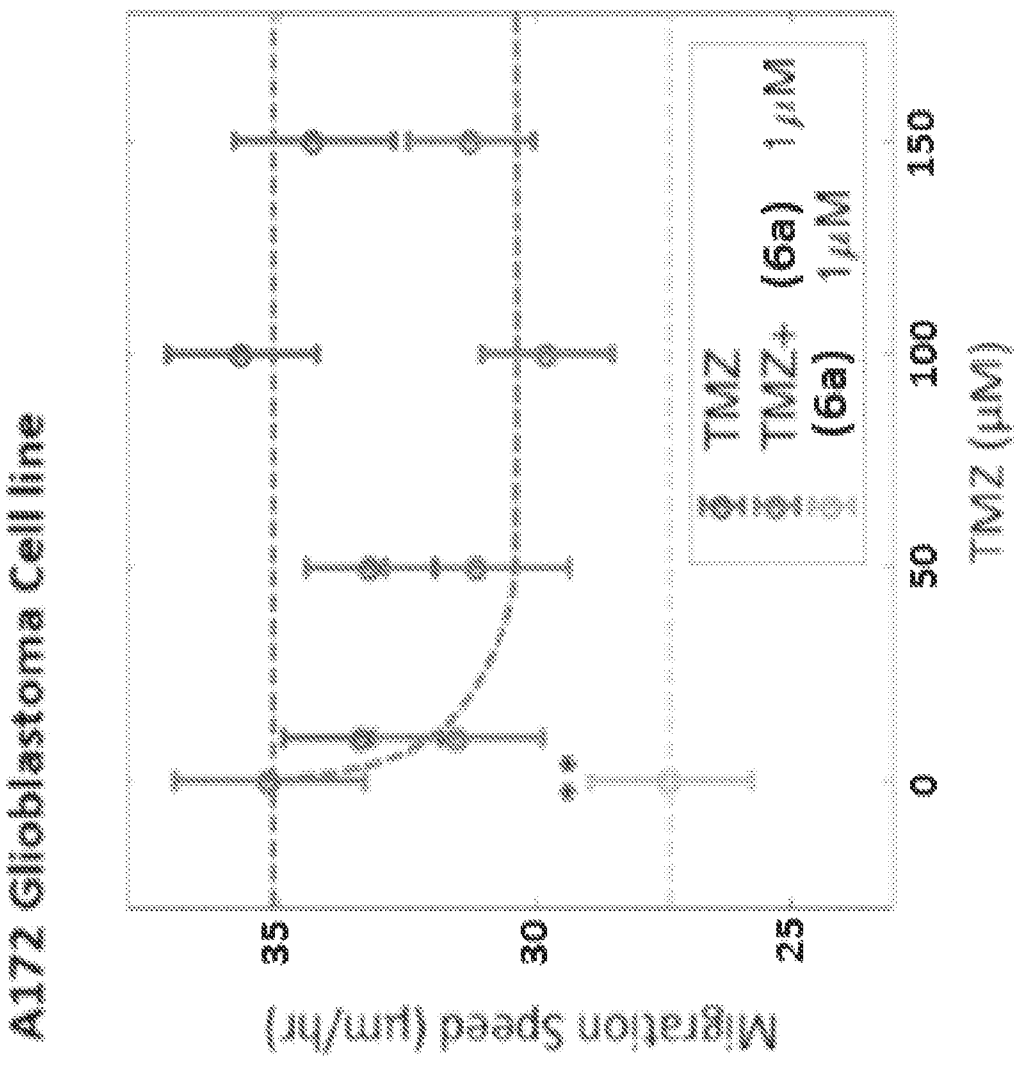
FIG. 27 illustrates a migratory response of GBM to (6a), TMZ (temozolomide, and a combination thereof, demonstrating that (6a) targeting of WNK1/SPAK impedes migration whereas first-line TMZ does not.
Figure 28:
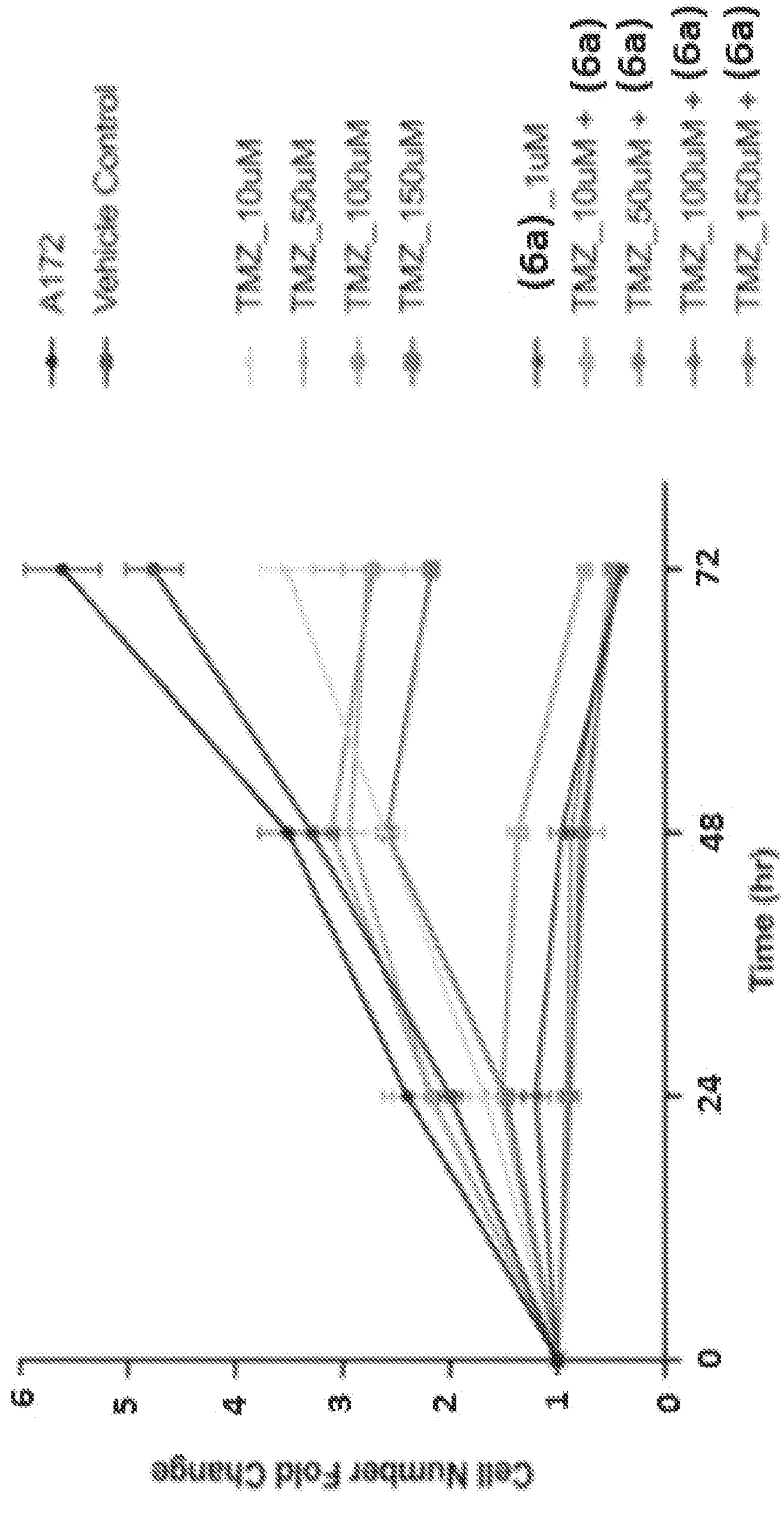
FIG. 28 illustrates time- and dose-dependent effect of TMZ, or a combination of TMZ and (6a), on GBM cell line A172 proliferation. Cell number of each group at different time points is normalized to which at time zero. The (6a) concentration used in all groups is 1 μM. Group named A172 corresponds to regular A172 culture condition.
Figure 29:
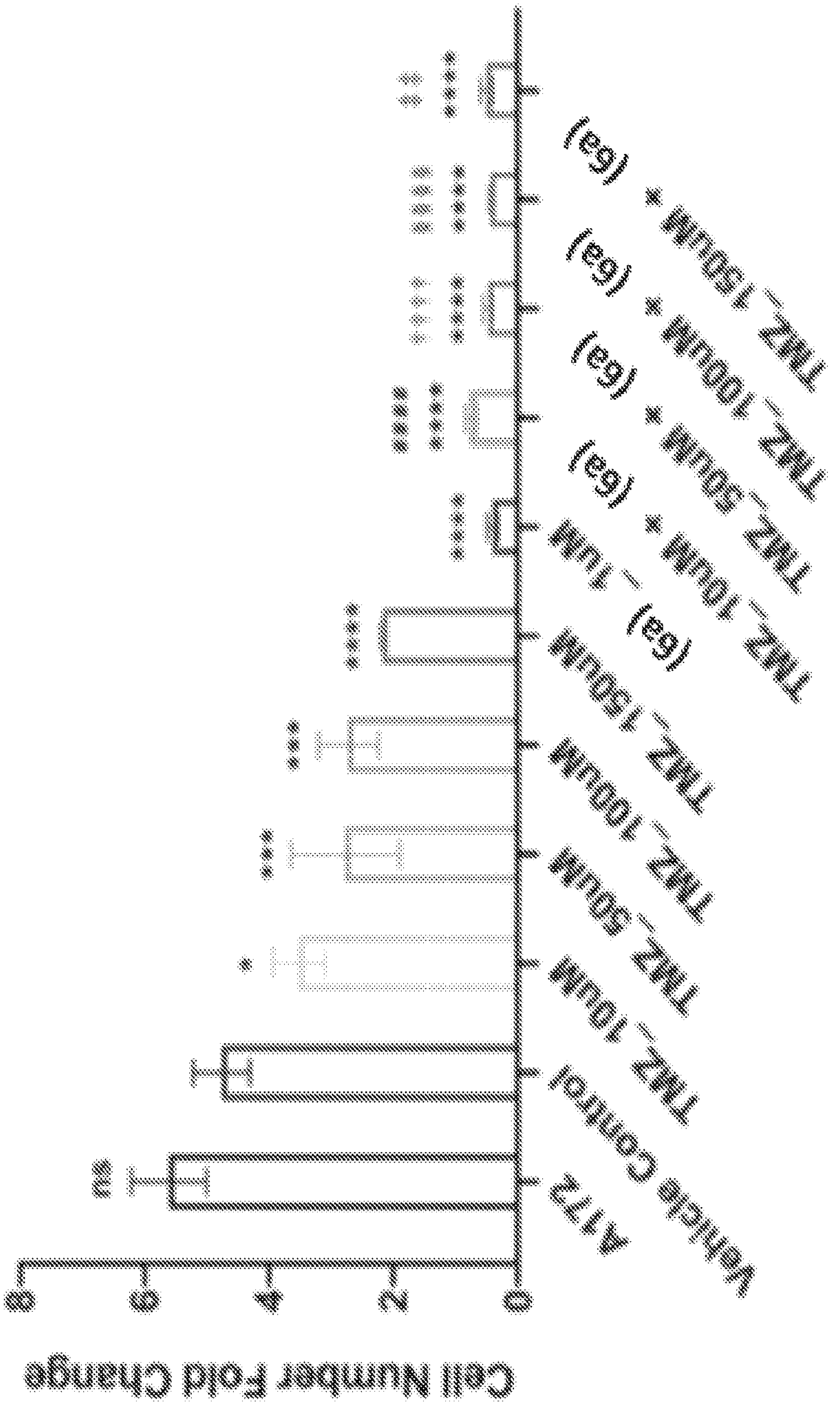
FIG. 29 illustrates cell number fold change after 72-hour incubation with TMZ or combination of TMZ and (6a). ns, * compared to vehicle control. # compared to TMZ_10 μM. † compared to TMZ_50 μM. § compared to TMZ_100 μM. ‡compared to TMZ_150 μM.
Figure 30:
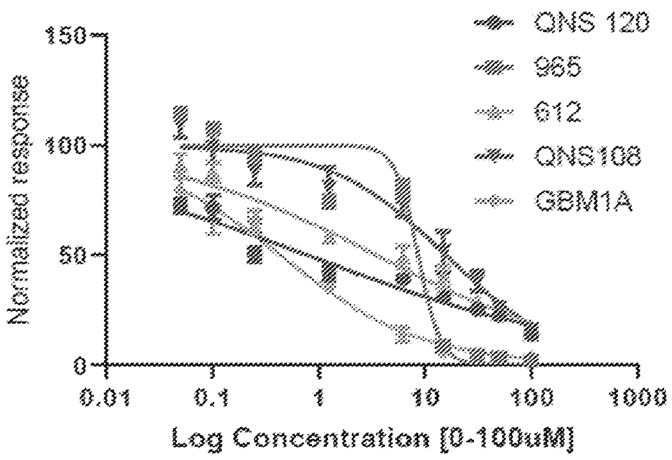
FIG. 30 illustrates that (6a) also impedes proliferation and viability of primary GBM cell lines.
Figure 31A:
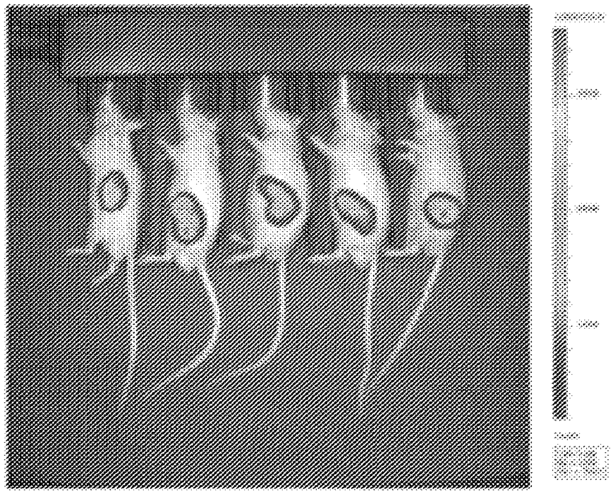
FIGS. 31A-31B illustrate subcutaneous GBM tumor response to low-dose (6a).
Figure 31B:
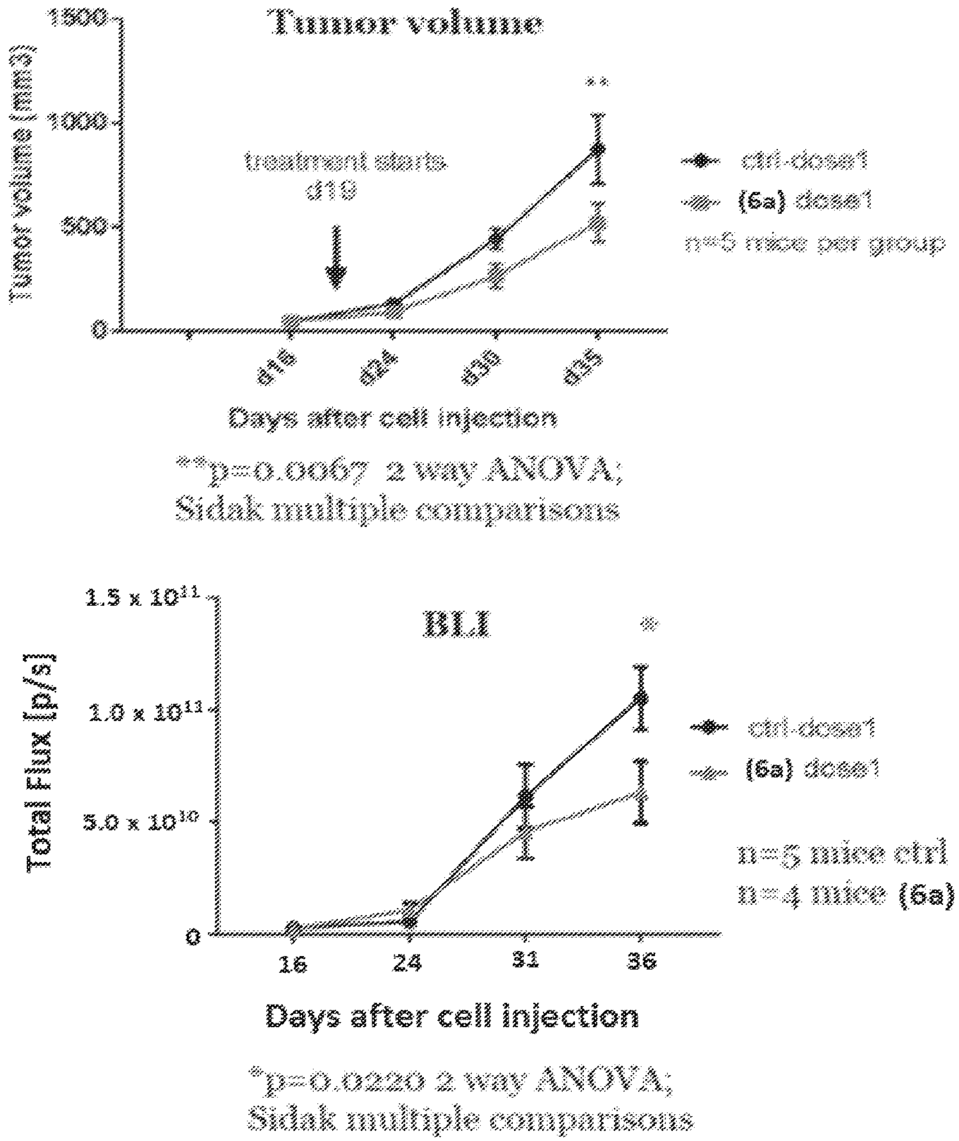
Figure 32A:
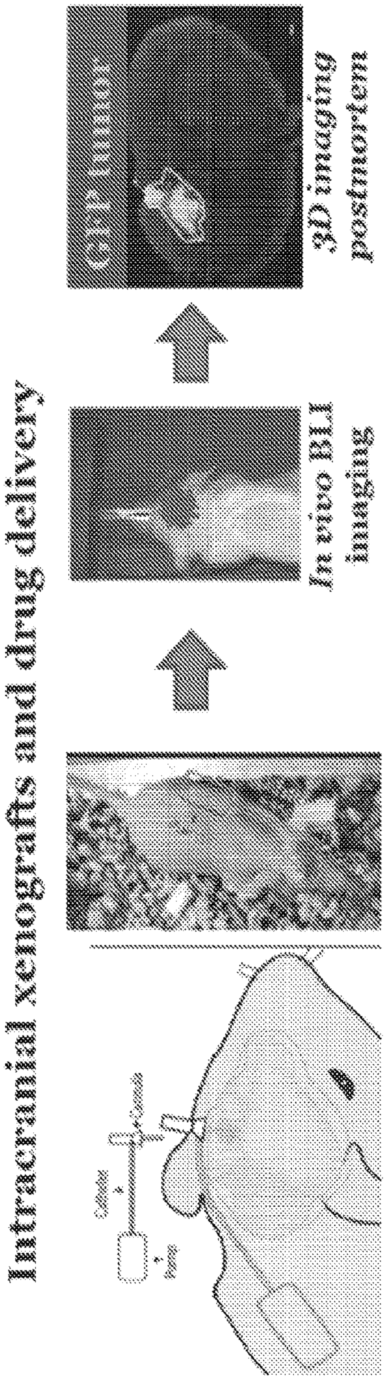
FIGS. 32A-32B illustrate that (6a) reduces tumor growth in vivo in a human GMB intracranial xenograft mouse model.
Figure 32B:
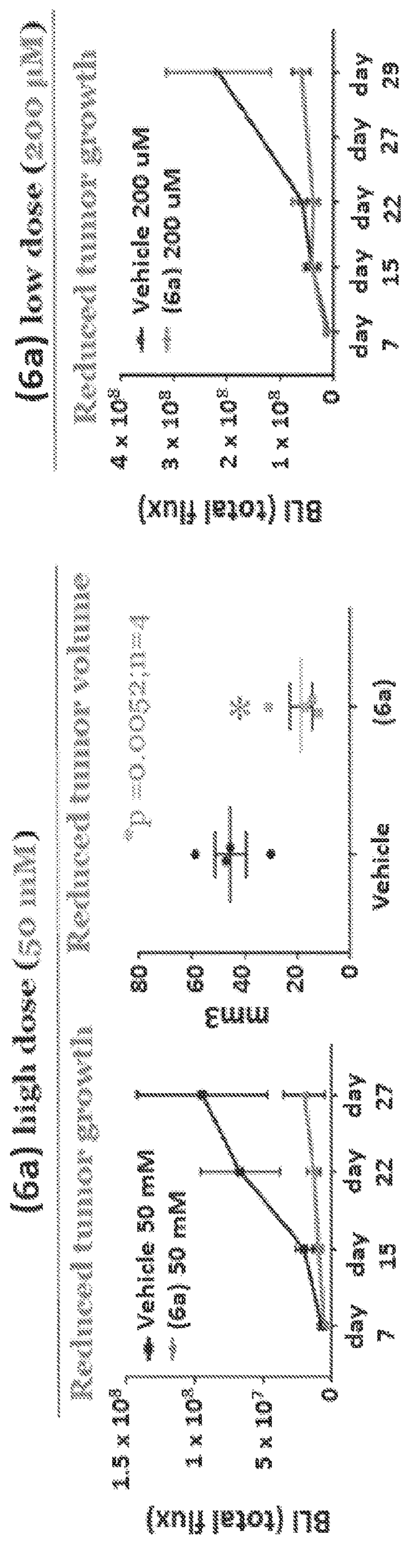
Figure 34:
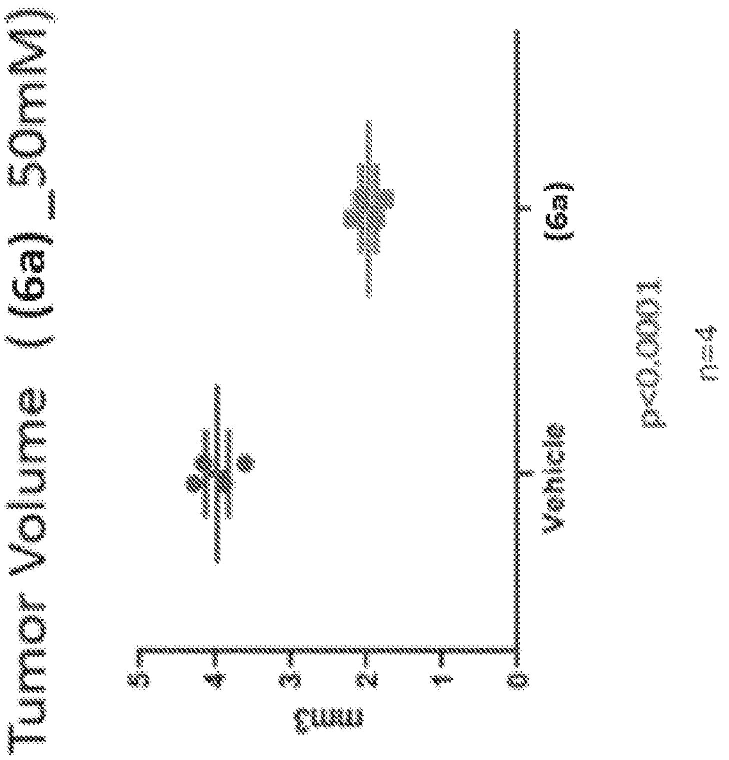
FIG. 34 illustrates the finding that (6a) reduces tumor volume in a GMB intracranial xenograft mouse model.
Figure 33:
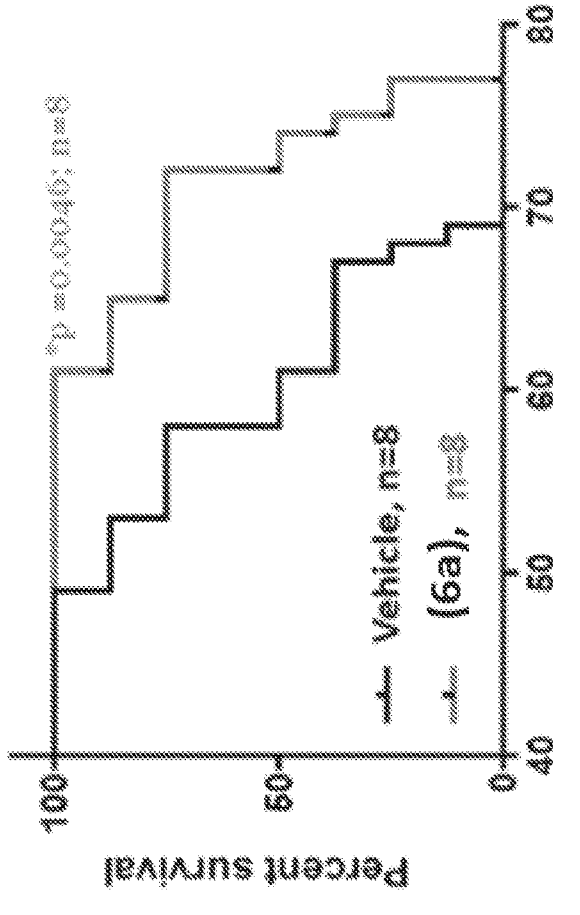
FIG. 33 illustrates the finding that (6a) extends overall survival in a GMB intracranial xenograft mouse model.
Figure 36:
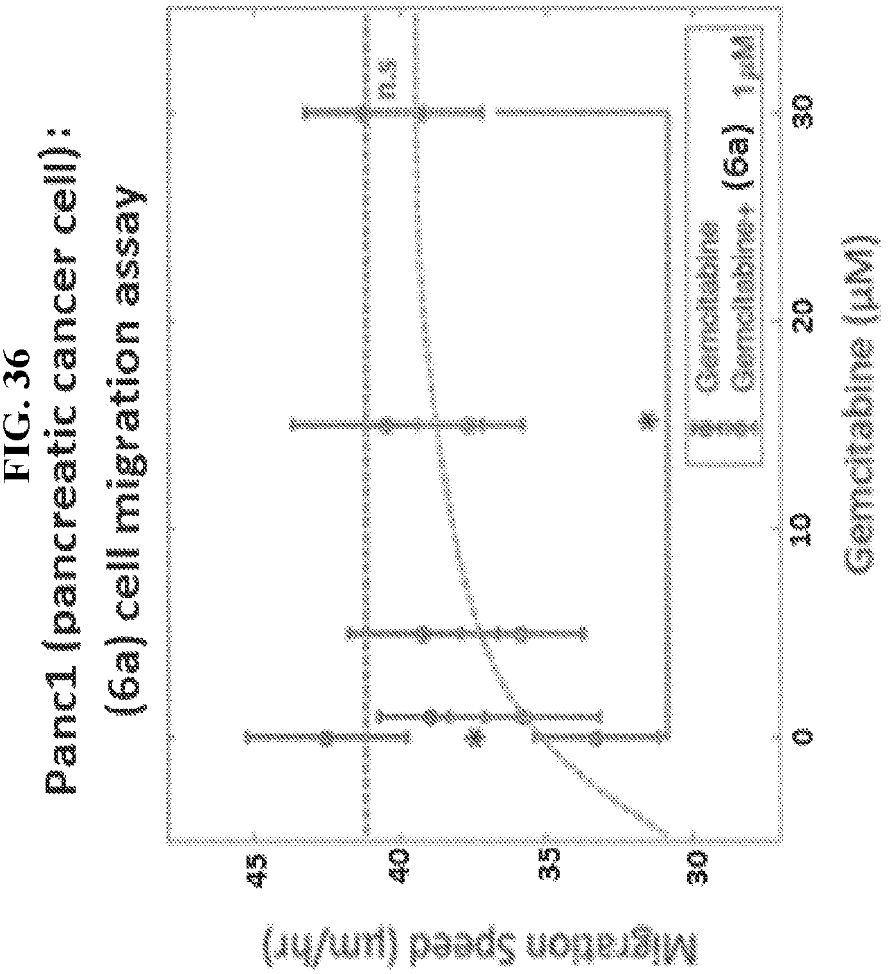
FIG. 36 illustrates an illustrative migratory response of pancreatic cancer cells to (6a), Gemcitabine, and a combination thereof, demonstrating that (6a) targeting of WNK1/SPAK impedes migration whereas first-line Gemcitabine does not.
Figure 35:
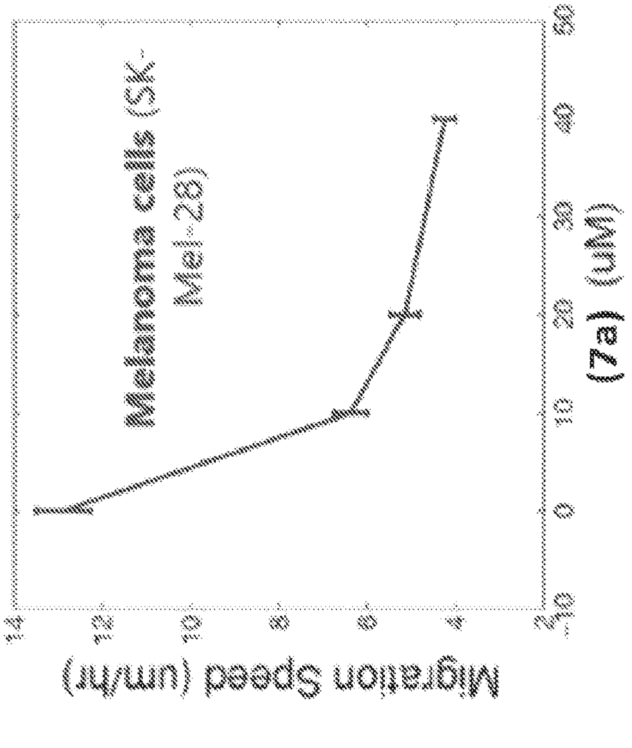
FIG. 35 illustrates the finding that (7a) reduces melanoma cell migration in vitro.

In vitro experiments showed that (6a) reduced migration of primary GBM cells, but was not active on primary human astrocytes (FIG. 26). Similarly, (6a) reduced melanoma cell migration in vitro (FIG. 35) and pancreatic cancer cell migration in vitro (FIG. 36). Interestingly, (6a) was able to inhibit cell migration in glioblastoma and pancreatic cancer in vitro models, while standard therapies for such cancers had no such anti-migratory effect (FIG. 27 and FIG. 36). Further, (6a) was successfully used in a GMB intracranial xenograft mouse model, where it induced reduction in tumor growth, reduced tumor volume, and extended overall survival (FIGS. 32A-32B, 33, and 34).

FIG. 36 illustrates an illustrative migratory response of pancreatic cancer cells to (6a), Gemcitabine, and a combination thereof, demonstrating that (6a) targeting of WNK1/SPAK impedes migration whereas first-line Gemcitabine does not.

6b

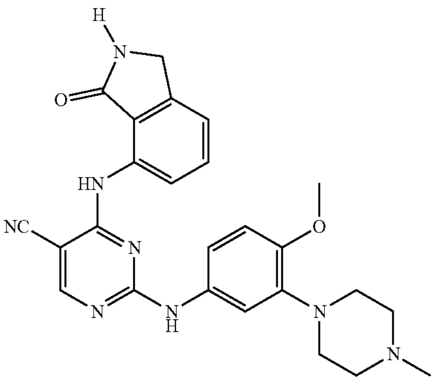

-continued
6c
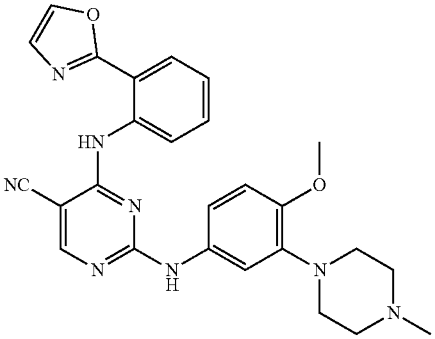
6d
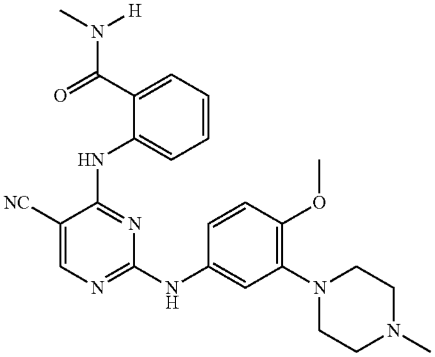
6e
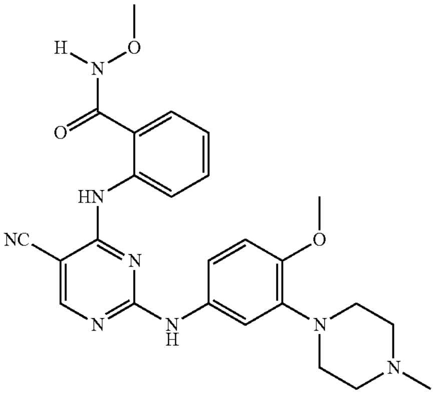
6f
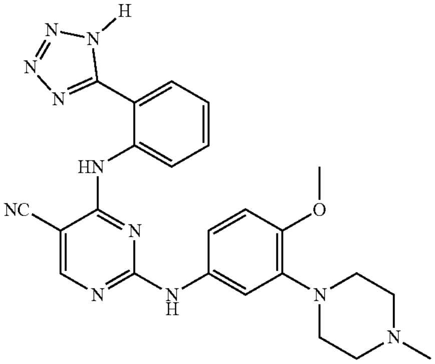
-continued
6g
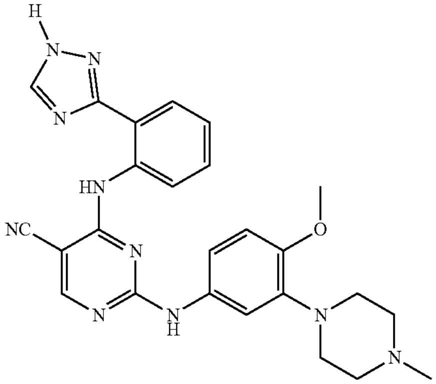 [SMILES: COc1ccc(Nc2ncc(C#N)c(Nc3ccccc3-c3nc[nH]n3)n2)cc1N1CCN(C)CC1]
TABLE 1
| On target activity in vitro and in GBM cells | | | |
|---|---|---|---|
| | $IC_{50}$ μM | Activity in GMB612 | |
| Compound | In vitro | 2 μM | 0.2 μM |
| (6b) | 0.05 | Yes | Yes |
| (6c) | 9 | No | No |
| (6d) | 5.2 | Yes | No |
| (6e) | 2.6 | Yes | No |
| (6f) | 3.5 | Yes | No |
| (6g) | 12 | No | No |
Example 9: Synthesis
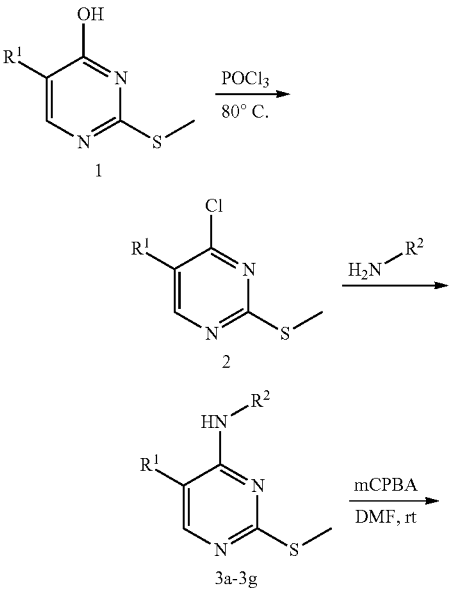

-continued

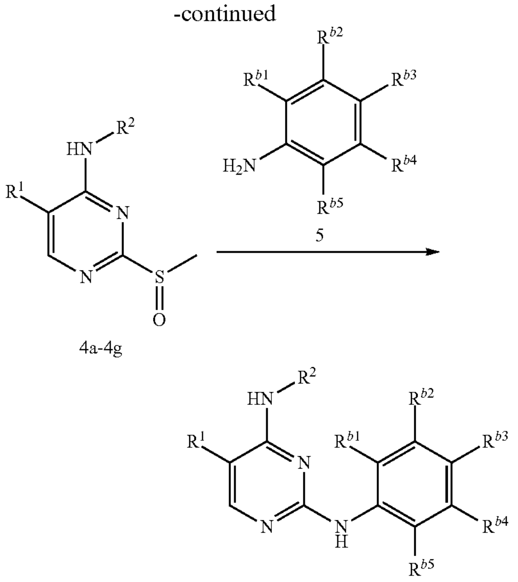

4a-4g

5

6a-6g

Step 1:

2a

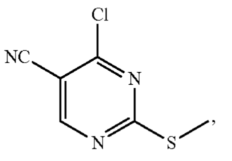

$R^1$ = CN

Synthesis of 4-chloro-2-(methylthio)pyrimidine-5-carbonitrile (2a)

To a 25 mL round bottom flask equipped with magnetic stir bar is added 4-hydroxy-2-methylsulfanyl-pyrimidine-5-carbonitrile (1) (2.50 g, 15.0 mmol) followed by $POCl_3$ (11.5 g, 74.9 mmol, 7.0 mL). The cloudy mixture is stirred and heated to 80° C. to provide a clear yellow solution, which is stirred at the same temperature for 5 h. After 5 h, the reaction mixture is cooled to room temperature and the magnetic stir bar is removed. Excess $POCl_3$ is removed from the reaction mixture under reduced pressure via rotary evaporator before poured into layers of ice-water and $CH_2Cl_2$ in the separatory funnel. The aqueous layer is separated and extracted with $CH_2C_2$ (3×15 mL). The combined organic layer is washed with saturated aqueous $K_2CO_3$ solution, dried with solid $K_2CO_3$ (ACS reagent grade), and the drying agent is removed by vacuum filtration. The filtrate is treated with activated charcoal and then vacuum filtered to remove colored impurities. Removal of solvent under reduced pressure provided chloropyrimidine product (2a) (2.48 g, 89%) as off-white crystalline solid. LC-MS: $t_R$=2.8 min, m/z=186.0 ESI/[M+H]$^+$).

Step 2:

3a

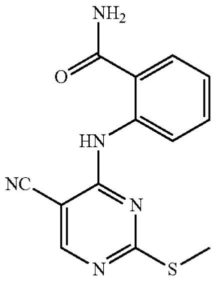

Synthesis of 2-((5-cyano-2-(methylthio)pyrimidin-4-yl)amino)benzamide (3a)

To a 100 mL round bottom flask equipped with magnetic stir bar is added chloropyrimidine (2) (2.48 g, 13.4 mmol) and dioxane (12 mL, anhydrous). To the stirring solution of (2) in dioxane is then added a solution of 2-aminobenzamide (1.82 g, 13.4 mmol) in dioxane (13 mL, anhydrous) at room temperature. A condenser is attached to the round bottom flask and the reaction is heated to reflux for 24 h before cooled down to room temperature. The insoluble solid is filtered by vacuum filtration, washed with $Et_2O$, and dried under vacuum to afford crude benzamide product (3a) (3.69 g, 97%) as solid powder. $^1$H NMR (400 MHz, DMSO-$d_6$) δ 12.51 (s, 1H), 8.67 (s, 1H), 8.57 (d, J=8.4 Hz, 1H), 8.37 (s, 1H), 7.87 (d, J=7.9 Hz, 2H), 7.58 (t, J=8.1 Hz, 1H), 7.21 (t, J=7.6 Hz, 1H).

3b-3g

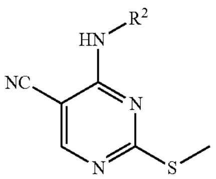

General Procedure for Synthesis of 3b-3g

To a 15 mL high pressure flask equipped with a magnetic stir bar is added chloropyrimidine (2)2 (120 mg, 646 μmol), the corresponding aniline (1 equiv, 646 μmol), Hunig's base (1.0 mL), and isopropanol (1.0 mL, anhydrous). The reaction mixture is heated to 90° C. and stirred for 16 h at the same temperature before cooled down to room temperature. The insoluble solid is filtered by vacuum filtration, washed with $Et_2O$, and dried under vacuum to afford crude product (3b)-(3g) as solid powder.

3b

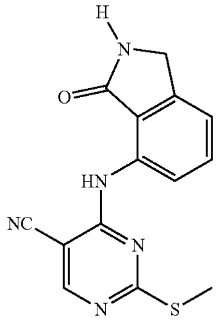

Synthesis of 2-(methylthio)-4-((3-oxoisoindolin-4-yl)amino)pyrimidine-5-carbonitrile (3b)

The general procedure for (3b)-(3g) is followed using 7-aminoisoindolin-1-one (101 mg, 646 mol) to provide product (3b) (81 mg, 42%) as solid. $^1$H NMR (400 MHz, DMSO-$d_6$) δ 11.04 (s, 1H), 8.87 (s, 1H), 8.74 (s, 1H), 8.52 (d, J=8.2 Hz, 1H), 7.64 (t, J=7.9 Hz, 1H), 7.30 (d, J=7.5 Hz, 1H), 4.43 (s, 2H), 2.60 (s, 3H).

3c

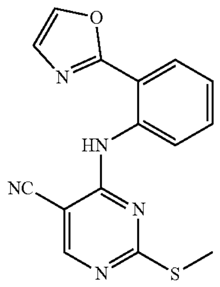

Synthesis of 2-(methylthio)-4-((2-(oxazol-2-yl)phenyl)amino)pyrimidine-5-carbonitrile (3c)

The general procedure for (3b)-(3g) is followed using 2-(oxazol-2-yl)aniline (109 mg, 646 mol) to provide product (3c) (140 mg, 70%) as solid. $^1$H NMR (400 MHz, DMSO-$d_6$) δ 11.89 (s, 1H), 8.73 (s, 1H), 8.64 (d, J=8.5 Hz, 1H), 8.33 (s, 1H), 8.06 (dd, J=7.9, 1.5 Hz, 1H), 7.60 (t, J=7.9 Hz, 1H), 7.47 (s, 1H), 7.33 (t, J=7.6 Hz, 1H), 2.53 (s, 3H).

3d

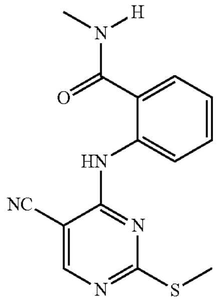

Synthesis of 2-((5-cyano-2-(methylthio)pyrimidin-4-yl)amino)-N-methylbenzamide (3d)

The general procedure for (3b)-(3g) is followed using 2-amino-N-methylbenzamide (102 mg, 646 μmol) to provide product (3d) (170 mg, 88%) as solid. $^1$H NMR (400 MHz, DMSO-$d_6$) δ 12.08 (s, 1H), 8.79 (s, 1H), 8.67 (s, 1H), 8.47 (d, J=8.4 Hz, 1H), 7.79 (d, J=7.9 Hz, 1H), 7.56 (t, J=7.9 Hz, 1H), 7.22 (t, J=7.6 Hz, 1H), 2.81 (d, J=4.5 Hz, 3H), 2.52 (s, 3H).

3e

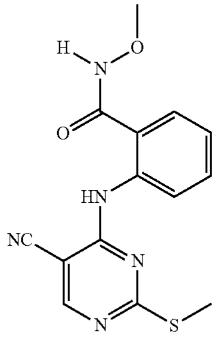

Synthesis of 2-((5-cyano-2-(methylthio)pyrimidin-4-yl)amino)-N-methoxybenzamide (3e)

The general procedure for (3b)-(3g) is followed using 2-amino-N-methoxybenzamide (113 mg, 646 μmol). The reaction mixture is concentrated down under reduced pressure before purified via flash column chromatography with MeOH/$CH_2Cl_2$. The isolated material that is not pure is confirmed by LC-MS to contain the desired product (3e) before used in the next step. LC-MS: $t_R$=2.8 min, m/z=316.1 ESI/[M+H]$^+$).

3f

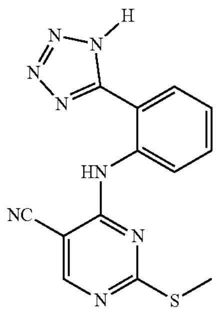

Synthesis of 4-((2-(1H-tetrazol-5-yl)phenyl)amino)-2-(methylthio)pyrimidine-5-carbonitrile (3))

The general procedure for (3b)-(3g) is followed using 2-(1H-tetrazol-5-yl)aniline (104 mg, 646 μmol). The reaction mixture is concentrated down under reduced pressure before purified via flash column chromatography with MeOH/$CH_2Cl_2$. The isolated material that is not pure is confirmed by LC-MS to contain the desired product (3f) before used in the next step. LC-MS: $t_R$=2.8 min, m/z=311.0 ESI/[M+H]$^+$).

3g

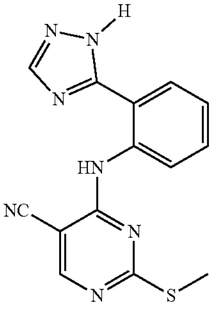

Synthesis of 4-((2-(1H-1,2,4-triazol-5-yl)phenyl) amino)-2-(methylthio)pyrimidine-5-carbonitrile (3g)

The general procedure for (3b)-(3g) is followed using 2-(1H-1,2,4-triazol-5-yl)aniline (109 mg, 646 μmol) to provide product (3g) (116 mg, 58%) as solid. $^1$H NMR (400 MHz, DMSO-$d_6$) δ 9.70 (s, 1H), 9.19 (s, 1H), 8.06 (d, J=7.9 Hz, 1H), 7.19 (t, J=7.6 Hz, 1H), 6.83 (d, J=7.7 Hz, 1H), 6.68-6.62 (m, 3H), 2.69 (s, 3H).

Step 3 and 4:

6a

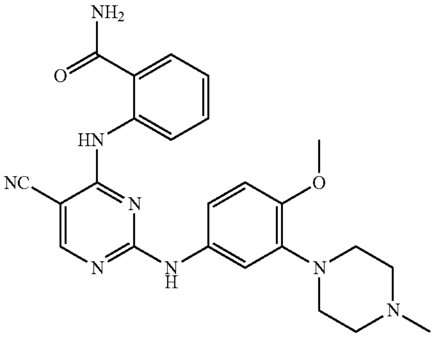

Synthesis of 2-((5-cyano-2-((4-methoxy-3-(4-methylpiperazin-1-yl)phenyl)amino)pyrimidin-4-yl) amino)benzamide (6a)

To a 20 mL scintillation vial equipped with magnetic stir bar is added methyl thioether 3a (200 mg, 701 μmol) and DMF (4 mL, anhydrous). The vial is sonicated and heated gently until complete dissolution. To the stirring solution of (3a) in DMF is added mCPBA (181 mg, 736 μmol, 70% purity) at room temperature before stirred for 2 h at the same temperature. After stirring at room temperature for 2 h or until complete consumption of starting material 3a as determined by LC-MS, 4-methoxy-3-(4-methylpiperazin-1-yl) aniline (160 mg, 701 μmol) is added to the reaction mixture and then stirred at room temperature for 16 h. After stirring for 16 h at room temperature, the reaction mixture is passed through a short plug of silica gel column with 1:1 MeOH/ $CH_2Cl_2$ mix. The filtrate is concentrated down to dryness to remove remaining DMF before re-dissolved in minimal amount of 1:4 MeOH/$CH_2Cl_2$ mix and then washed with saturated aqueous $K_2CO_3$ solution in a separatory funnel. The separated aqueous layer is extracted with $CH_2Cl_2$ (3×10 mL) and all the organic layers are combined and dried with $MgSO_4$. The drying agent is removed by vacuum filtration and the filtrate is concentrated to dryness to provide the solid crude product. Crude material as solid is triturated with $CH_2Cl_2$ with assist from sonication, and the resulting suspension is vacuum filtered. The filtered solid is washed with $Et_2O$ and dried under vacuum to deliver the desired product (6a) (160 mg, 50% over two steps) as off-white solid. LC-MS: $t_R$=2.2 min, m/z=459.2 ESI[M+H]$^+$).

6b-6g

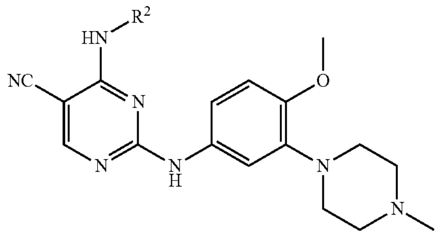

General Procedure for Synthesis of (6b)-(6g)

To a 20 mL scintillation vial equipped with magnetic stir bar is added the corresponding methyl thioether (3b)-(3g) (30 mg) and DMF (anhydrous). The vial is sonicated and heated gently until complete dissolution. To the stirring solution of (3b)-(3g) is added mCPBA (1.0 equiv, 70% purity) at room temperature before stirred for 2 h at the same temperature. After stirring at room temperature for 2 h or until complete consumption of starting material as determined by LC-MS, the 4-methoxy-3-(4-methylpiperazin-1-yl)aniline (1.0 equiv) is added to the reaction mixture and then stirred at room temperature for 16 h. After stirring for 16 h at room temperature, the reaction mixture is diluted with EtOAc (10 mL) and extracted with aqueous 1N HCl solution (3×10 mL). The combined aqueous layer is treated with saturated aqueous $K_2CO_3$ solution until pH=10 before extracted with $CH_2Cl_2$ (3×15 mL). The combined organic layer is dried with $MgSO_4$, which is removed via vacuum filtration. The filtrate is concentrated under reduced pressure to provide the crude material that is purified by flash column chromatography with MeOH/$CH_2Cl_2$ as eluent to provide the clean desired product.

6b

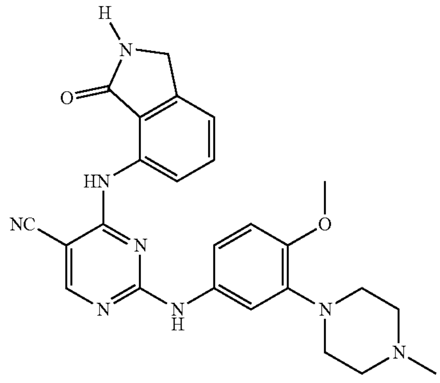

Synthesis of 4-((2-(1H-tetrazol-5-yl)phenyl)amino)-2-(methylthio)pyrimidine-5-carbonitrile (6b)

The general procedure for (6b)-(6g) is followed using methyl thioether (3b) (20.0 mg, 67.3 mol), mCPBA (16.6 mg, 67.3 μmol), 4-methoxy-3-(4-methylpiperazin-1-yl)aniline (14.9 mg, 67.3 μmol) and NMP as solvent (2 mL, anhydrous) to deliver the desired product (6b) (10.5 mg, 33% over two steps). LC-MS: $t_R$=2.3 min, m/z=471.2 ESI/[M+H]$^+$).

6c

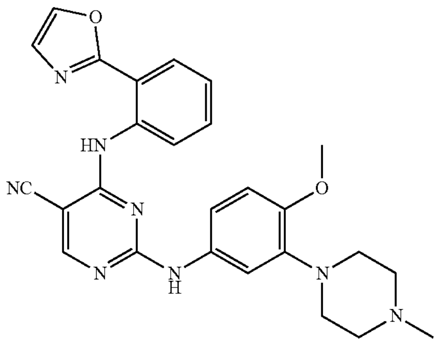

Synthesis of 2-((4-methoxy-3-(4-methylpiperazin-1-yl)phenyl)amino)-4-((2-(oxazol-2-yl)phenyl)amino) pyrimidine-5-carbonitrile (6c)

The general procedure for (6b)-(6g) is followed using methyl thioether (3c) (30.0 mg, 97.0 mol), mCPBA (23.9 mg, 97.0 μmol), 4-methoxy-3-(4-methylpiperazin-1-yl)aniline (21.5 mg, 97.0 μmol) and DMF as solvent (3 mL, anhydrous) to deliver the desired product (6c) (21.5 mg, 46% over two steps). LC-MS: $t_R$=2.9 min, m/z=483.2 ESI/[M+H]$^+$).

6d

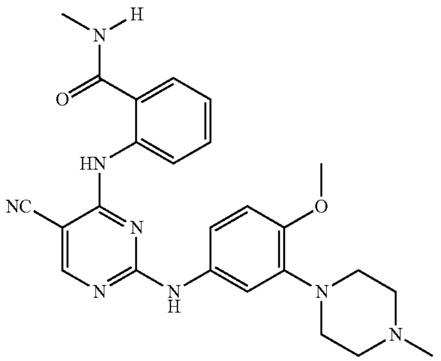

Synthesis of 2-((5-cyano-2-((4-methoxy-3-(4-methylpiperazin-1-yl)phenyl)amino)pyrimidin-4-yl) amino)-N-methylbenzamide (6d)

The general procedure for (6b)-(6g) is followed using methyl thioether (3d) (30.0 mg, 100 mol), mCPBA (24.7 mg, 100 μmol), 4-methoxy-3-(4-methylpiperazin-1-yl)aniline (22.9 mg, 100 μmol) and DMF as solvent (3 mL, anhydrous) to deliver the desired product (6d) (21.2 mg, 45% over two steps). LC-MS: $t_R$=2.3 min, m/z=473.1 ESI/[M+H]$^+$).

6e

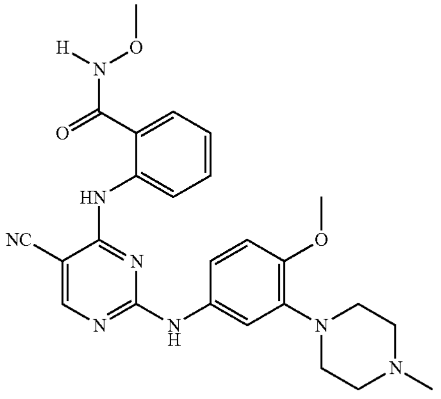

Synthesis of 2-((5-cyano-2-((4-methoxy-3-(4-methylpiperazin-1-yl)phenyl)amino)pyrimidin-4-yl) amino)-N-methoxybenzamide (6e)

The general procedure for (6b)-(6g) is followed using the isolated (but not pure) methyl thioether (3e) (77.3 mg, 245 μmol, assumed 100% purity for calculations), mCPBA (60.4 mg, 245 μmol), 4-methoxy-3-(4-methylpiperazin-1-yl)aniline (50.3 mg, 221 μmol) and DMF as solvent (2 mL, anhydrous) to deliver the desired product (6e) (11.8 mg, 10% over three steps) as red solid. LC-MS: $t_R$=2.3 min, m/z=489.2 ESI/[M+H]$^+$).

6f

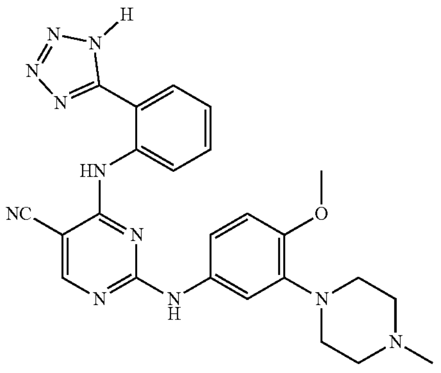

Synthesis of 4-((2-(1H-tetrazol-5-yl)phenyl)amino)-2-((4-methoxy-3-(4-methylpiperazin-1-yl)phenyl) amino)pyrimidine-5-carbonitrile (6f)

The general procedure for (6b)-(6g) is followed using the isolated (but not pure) methyl thioether (3f) (201 mg, 646 μmol, assumed 100% purity for calculations), mCPBA (159 mg, 646 μmol), 4-methoxy-3-(4-methylpiperazin-1-yl)aniline (147 mg, 646 μmol) and DMF as solvent (3 mL, anhydrous) to deliver the desired product (6f) (2.1 mg, 1% over three steps). LC-MS: $t_R$=2.3 min, m/z=484.2 ESI/[M+H]$^+$).

6g

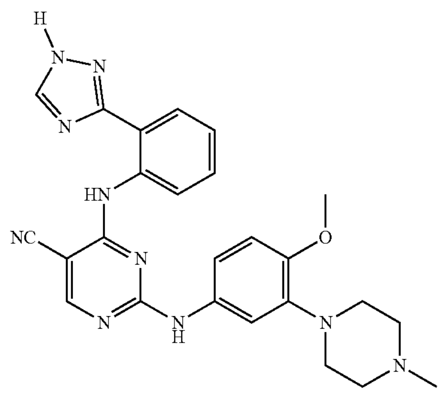

Synthesis of 4-((2-(1H-1,2,4-triazol-3-yl)phenyl) amino)-2-((4-methoxy-3-(4-methylpiperazin-1-yl) phenyl)amino)pyrimidine-5-carbonitrile (6g)

The general procedure for (6b)-(6g) is followed using methyl thioether (3g) (30 mg, 97.0 mol), mCPBA (23.9 mg, 97.0 μmol), 4-methoxy-3-(4-methylpiperazin-1-yl)aniline (22.1 mg, 97.0 μmol) and 3:1 mixture of DMF/NMP as solvent (4 mL, anhydrous) to deliver the desired product (6g) (7.5 mg, 16% over two steps). LC-MS: $t_R$=2.5 min, m/z=483.1 ESI/[M+H]$^+$).

Example 10: In Vitro and In Vivo Studies of (6a)

Figure 37:
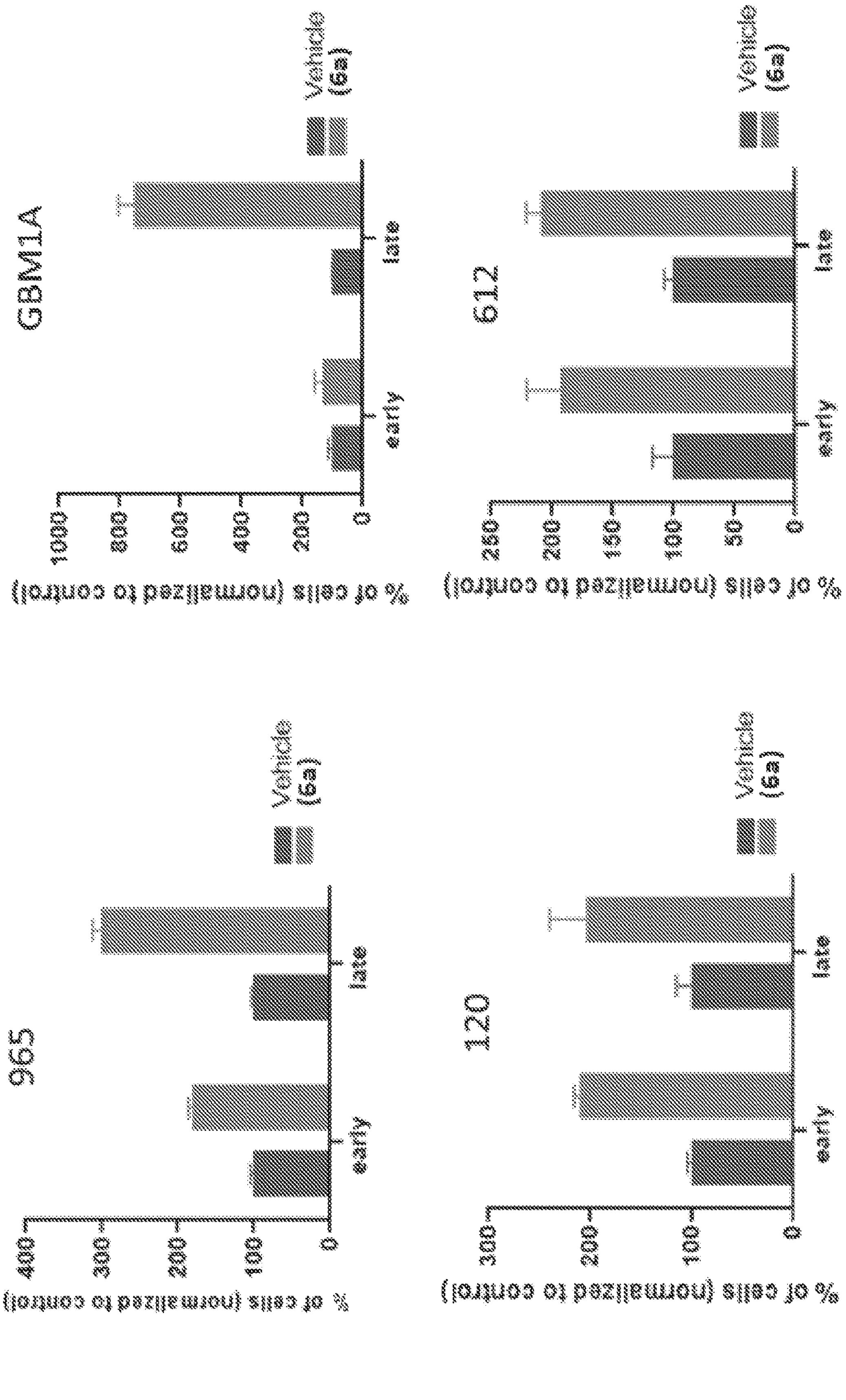
FIG. 37 depicts annexin V assays performed on four GBM cell lines after 1 μM of (6a) or vehicle control.

FIG. 37 depicts that (6a) induces apoptosis in GBM cell lines.

Figure 38A:
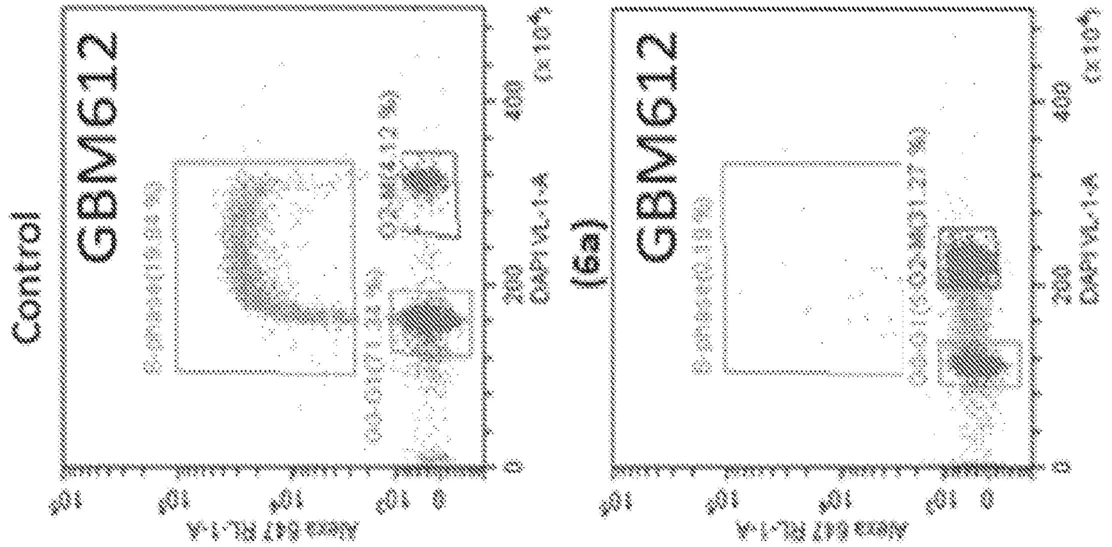
FIGS. 38A-38B depict that (6a) induces G2-M arrest in GBM cells.
Figure 38B:
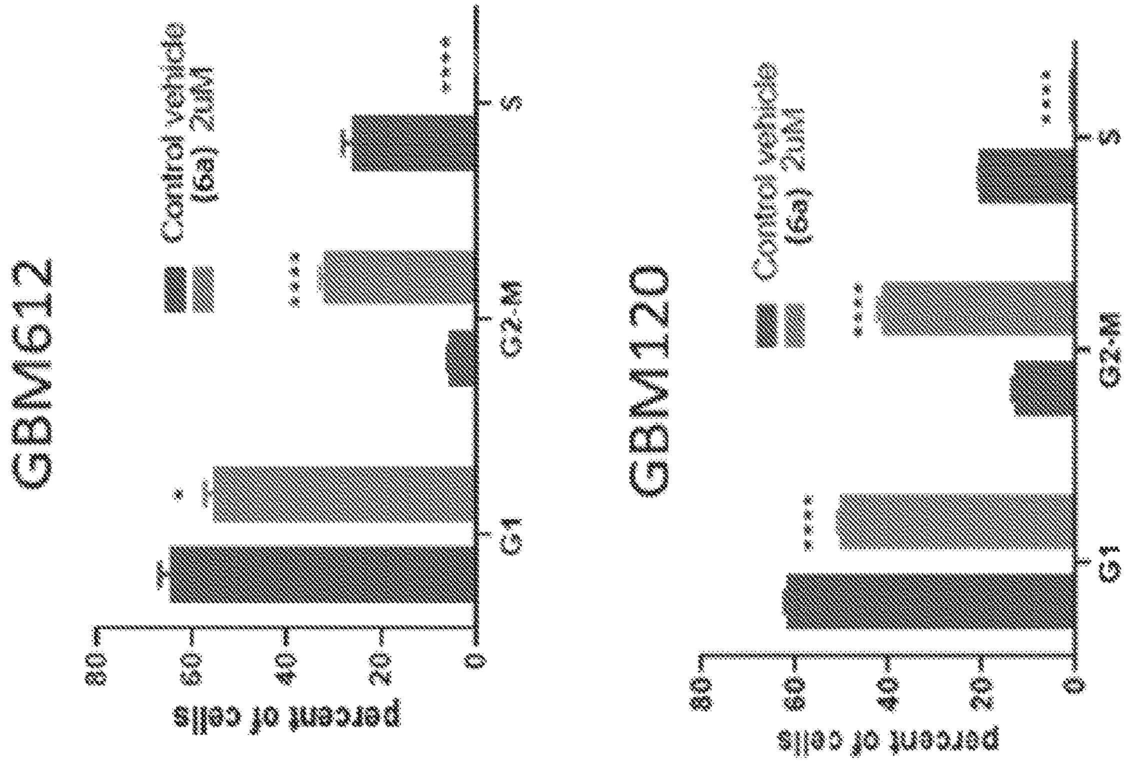

FIGS. 38A-38B depict that (6a) induces G2-M arrest in GBM cells.

Figure 39:
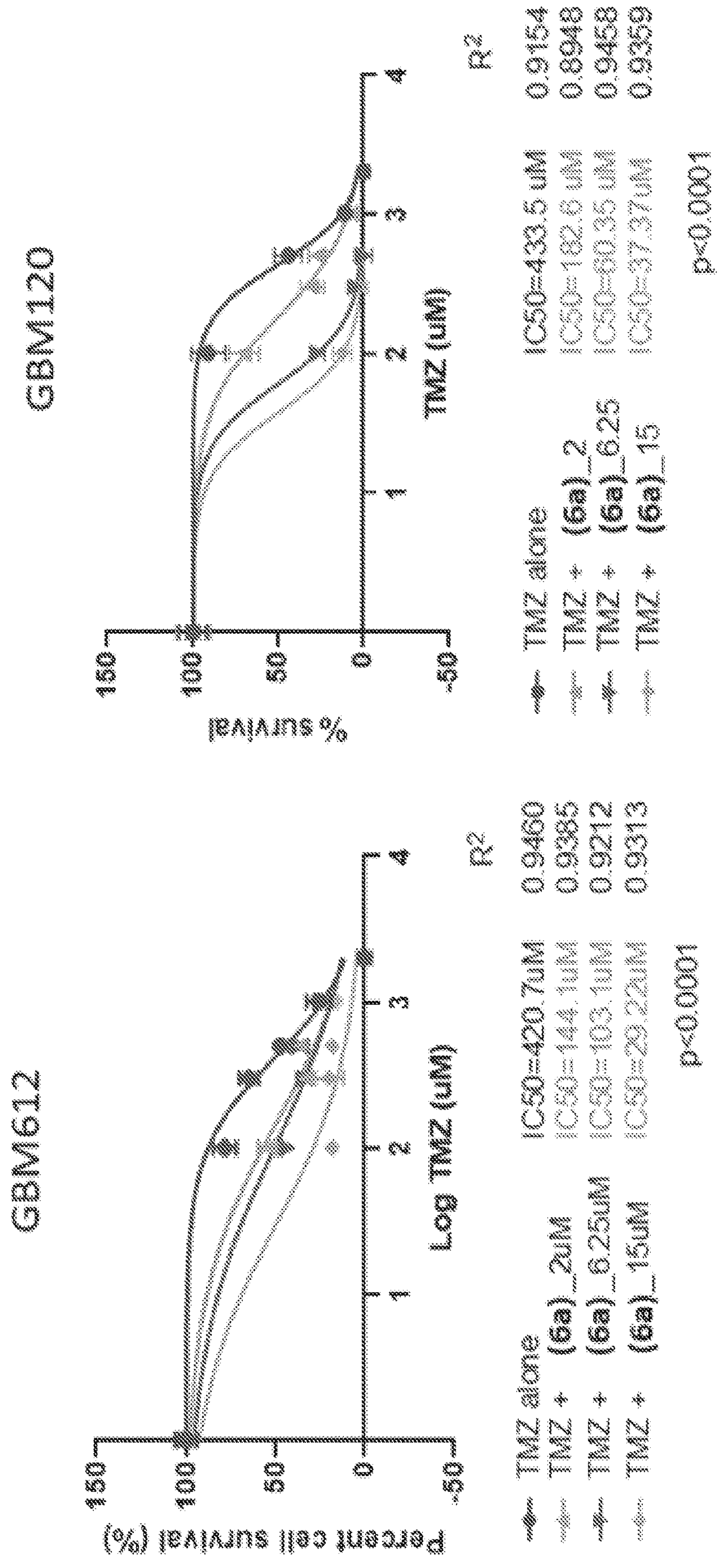
FIG. 39 depicts that the $IC_{50}$ values for temozolomide (TMZ) decrease 2-4 fold when used in combination (6a) in two different GBM cell lines (GBM 612, GBM120).

FIG. 39 depicts that (6a) sensitizes GBM cells to Temozolomide (TMZ) treatment.

Figure 40A:
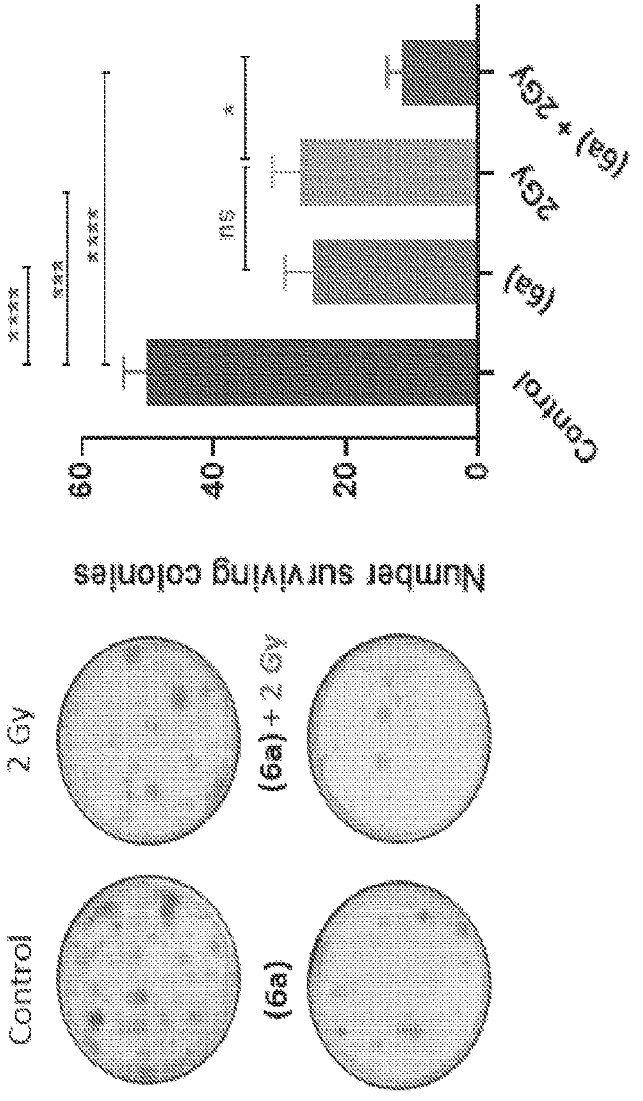
FIGS. 40A-40C depict that SPAK/OSR1 inhibition sensitizes GBM to radiation and decreases expression of DNA damage response genes.
Figure 40B:
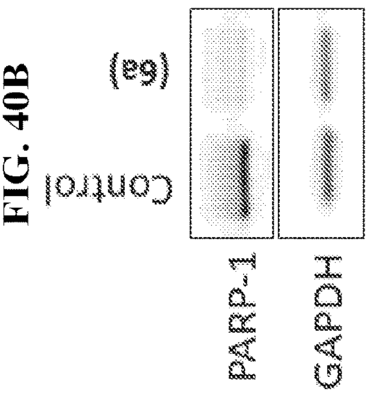
Figure 40C:
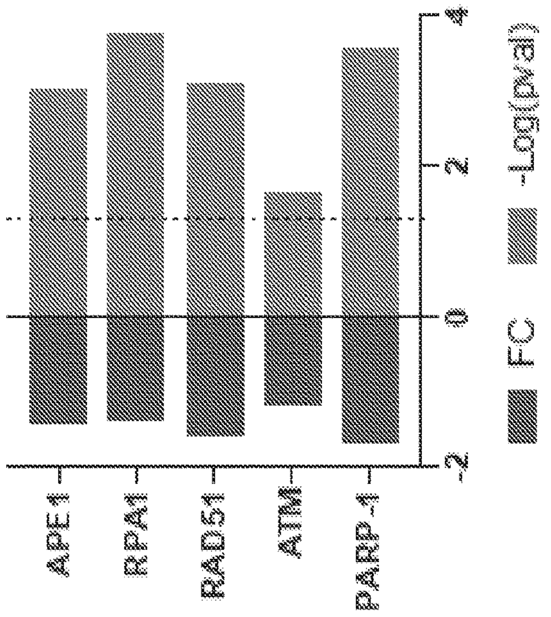

FIGS. 40A-40C depict that SPAK/OSR1 inhibition sensitizes GBM to radiation and decreases expression of DNA damage response genes.

Figure 41:
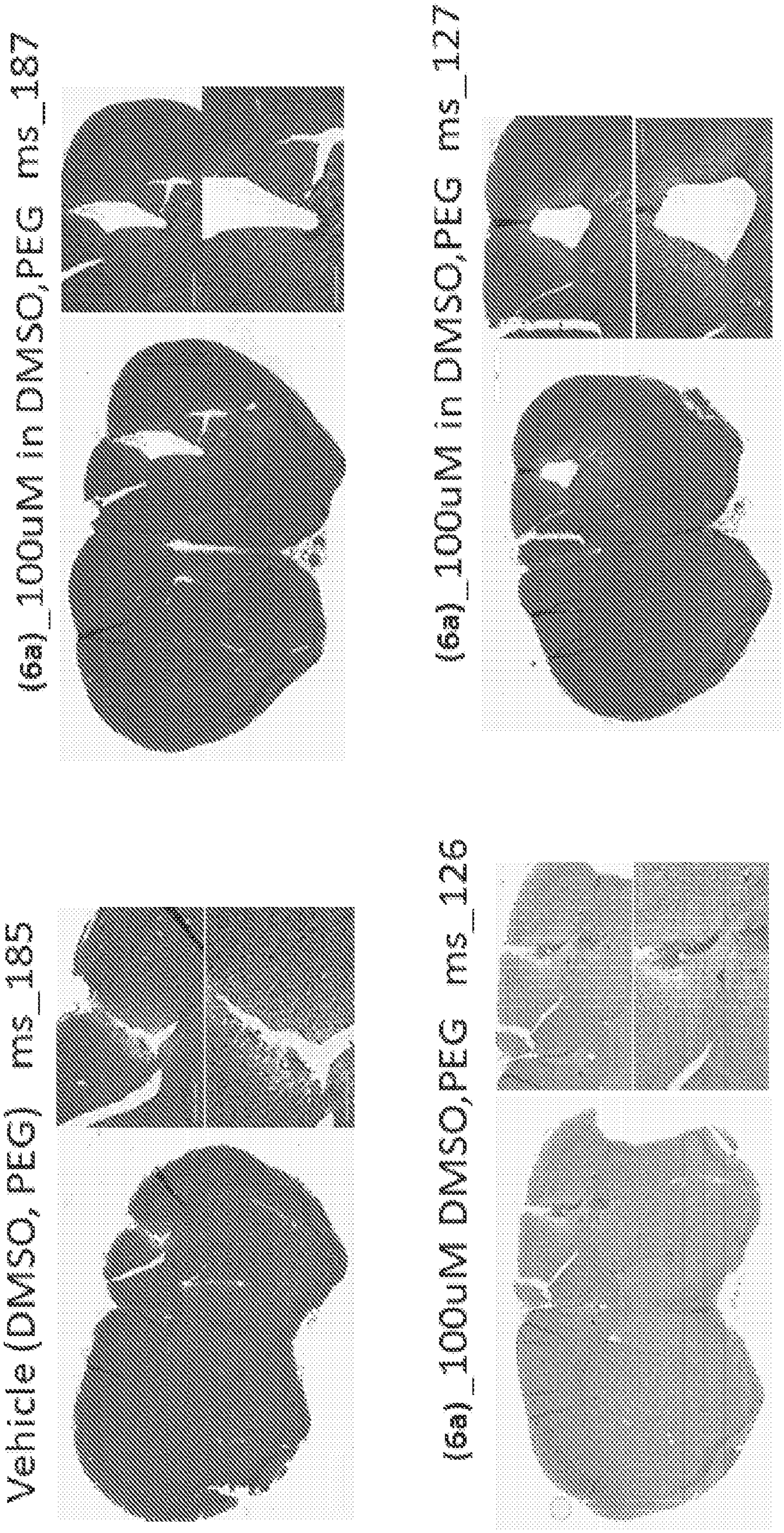
FIG. 41 depicts treating healthy, tumor free, mice (ms_#) intracranially with a DMSO/PEG formulation containing vehicle or 100 μM (6a).

FIG. 41 depicts the results of a (6a) formulation/tolerance test. (6a) and vehicle were well tolerated in healthy, tumor free, mice with no major adverse effects.

Enumerated Embodiments

The following exemplary embodiments are provided, the numbering of which is not to be construed as designating levels of importance.

Embodiment 1 provides a compound of formula (I), or a salt, solvate, isotopically labelled derivative, stereoisomer, tautomer, or geometric isomer thereof:

(I)

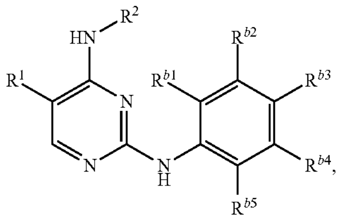

wherein: $R^1$ is selected from the group consisting of H, F, Cl, Br, I, $C_1$-$C_6$ alkyl, $C_1$-$C_6$ alkoxy, CN, nitro, and $CF_3$; $R^2$ is selected from the group consisting of:

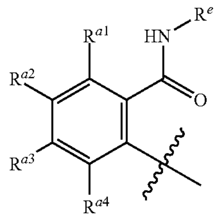
,
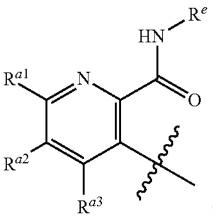
,
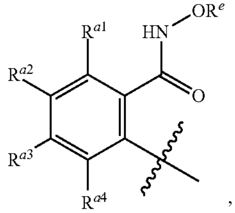
,
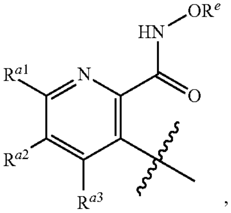
,
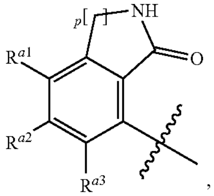
,
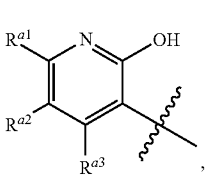
,
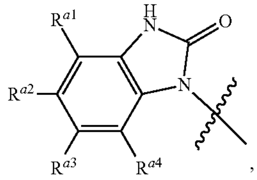
,
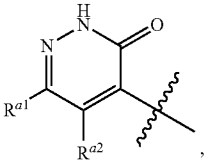
,
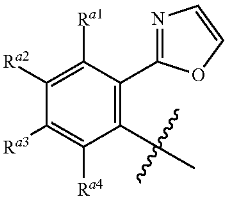
,
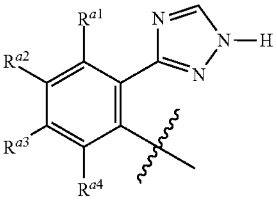
, and
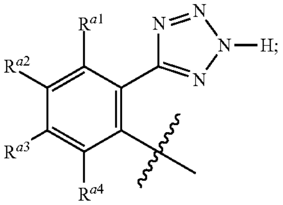

each occurrence of $R^{a1}$, $R^{a2}$, $R^{a3}$, and $R^{a4}$ is independently selected from the group consisting of H, F, Cl, Br, I, $C_1$-$C_6$ alkyl, $C_3$-$C_8$ cycloalkyl, phenyl, $C_1$-$C_6$ hydroxyalkyl, $C_1$-$C_6$ haloalkyl, $C_1$-$C_6$ haloalkoxy, ($C_1$-$C_6$ alkoxy)-$C_0$-$C_6$ alkylene, —$NR^cR^c$, —$OR^c$, —C(═O)$OR^c$, and —C(═O)N($R^c$)($R^c$), wherein each occurrence of $R^c$ is independently H, $C_1$-$C_6$ alkyl, or $C_3$-$C_8$ cycloalkyl, or two $R^c$ bound to the same N atom combine with the N atom to form optionally substituted 3- to 8-membered heterocyclyl; $R^{b1}$, $R^{b2}$, $R^{b3}$, $R^{b4}$, and $R^{b5}$ are independently selected from the group consisting of H, F, Cl, Br, I, $C_1$-$C_6$ alkyl, $C_3$-$C_8$ cycloalkyl, phenyl, $C_1$-$C_6$ hydroxyalkyl, $C_1$-$C_6$ haloalkyl, $C_1$-$C_6$ haloalkoxy, ($C_1$-$C_6$ alkoxy)-$C_0$-$C_6$ alkylene, —$(CH_2)_{0-3}$—$NR^dR^d$, —$O(CH_2)_{2-3}$—$NR^dR^d$, —$OR^d$, —C(═O)$OR^d$, and —C(═O)N($R^d$)($R^d$), wherein each occurrence of $R^d$ is independently H, $C_1$-$C_6$ alkyl, or $C_3$-$C_8$ cycloalkyl, or two $R^d$ bound to the same N atom combine with the N atom to form optionally substituted 3- to 8-membered heterocyclyl; each occurrence of $R^e$ is independently $C_1$-$C_6$ alkyl; p is 1, 2, or 3.

Embodiment 2 provides the compound of Embodiment 1, wherein $R^1$ is methyl, ethyl, methoxy, ethoxy, F, Cl, Br, I, CN, or $CF_3$.

Embodiment 3 provides the compound of any of Embodiments 1-2, wherein $R^1$ is CN.

Embodiment 4 provides the compound of any of Embodiments 1-3, wherein $R^2$ is

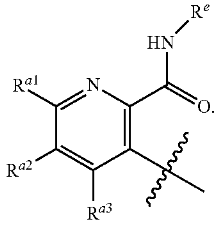

Embodiment 5 provides the compound of any of Embodiments 1-3, wherein $R^2$ is

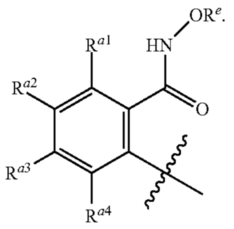

Embodiment 6 provides the compound of any of Embodiments 1-3, wherein $R^2$ is

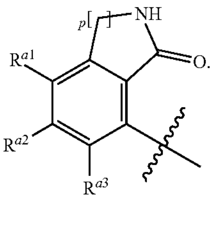

Embodiment 7 provides the compound of any of Embodiments 1-3, wherein $R^2$ is

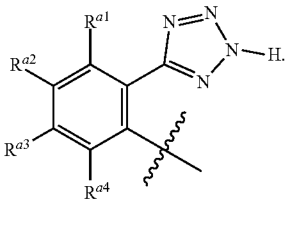

Embodiment 8 provides the compound of any of Embodiments 1-7, wherein

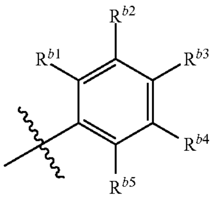

is

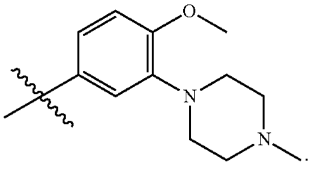

Embodiment 9 provides the compound of any of Embodiments 1-8, wherein the compound is selected from the group consisting of:

6b

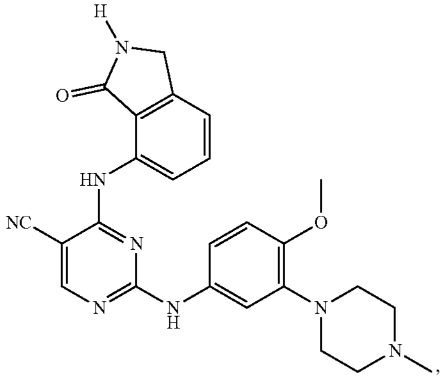

6c

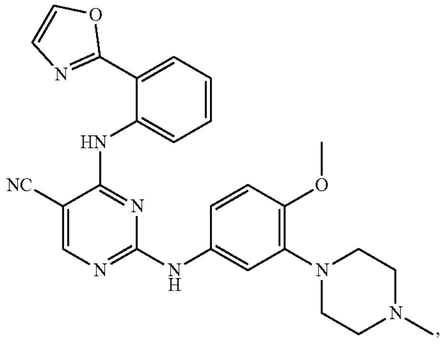

6d

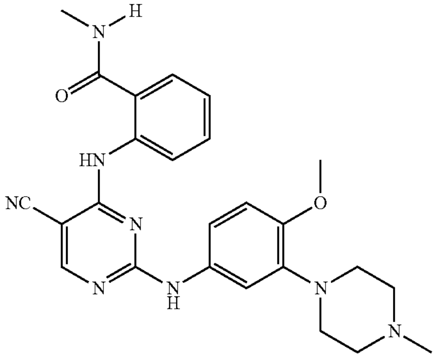

-continued

6e

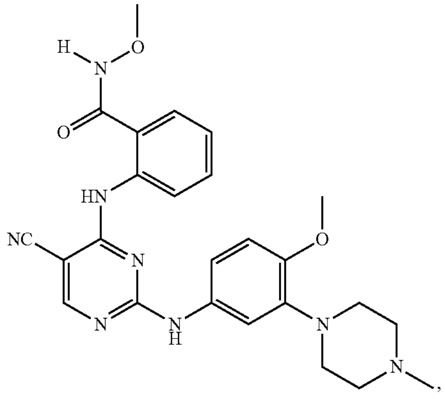

6f

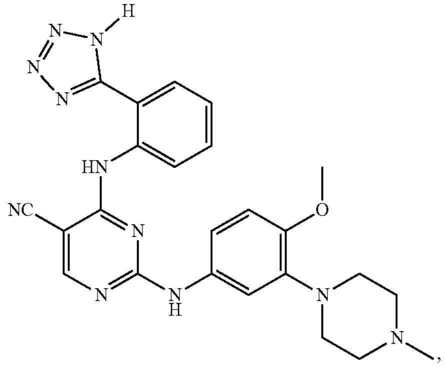

6g

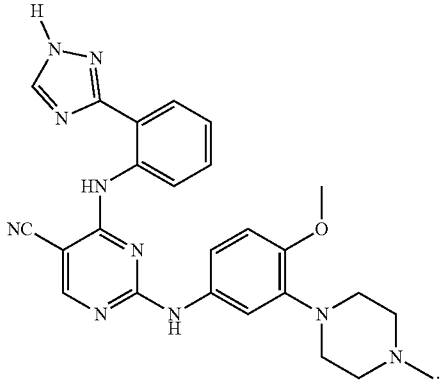

Embodiment 10 provides a pharmaceutical composition comprising at least one pharmaceutically acceptable excipient and a compound of any of Embodiments 1-9.

Embodiment 11 provides a method of inhibiting SPAK and/or OSR activity in a subject, the method comprising administering to the subject a therapeutically effective amount of a compound of any of Embodiments 1-9 and/or a pharmaceutical composition of Embodiment 10.

Embodiment 12 provides a method of treating, ameliorating, and/or preventing cancer in a subject, the method comprising administering to the subject a therapeutically effective amount of a compound of any of Embodiments 1-9 and/or a pharmaceutical composition of Embodiment 10.

Embodiment 13 provides a method of treating, ameliorating, and/or preventing cancer cell migration and/or invasion in a subject, the method comprising administering to the subject a therapeutically effective amount of a compound of any of Embodiments 1-9 and/or a pharmaceutical composition of Embodiment 10.

Embodiment 14 provides a method of reducing or reversing growth and/or viability of a cancer in a subject, the method comprising administering to the subject a therapeutically effective amount of a compound of any of Embodiments 1-9 and/or a pharmaceutical composition of Embodiment 10.

Embodiment 15 provides a method of reducing volume of a cancerous tumor in a subject, the method comprising administering to the subject a therapeutically effective amount of a compound of any of Embodiments 1-9 and/or a pharmaceutical composition of Embodiment 10.

Embodiment 16 provides a method of extending survival in a subject afflicted with a cancer, the method comprising administering to the subject a therapeutically effective amount of a compound of any of Embodiments 1-9 and/or a pharmaceutical composition of Embodiment 10.

Embodiment 17 provides the method of any of Embodiments 11-16, wherein the cancer comprises at least one of melanoma, glioblastoma, pancreatic cancer, thyroid cancer, lung cancer, breast cancer, colorectal cancer, and other invasive and metastatic cancers.

Embodiment 18 provides the method of any of Embodiments 11-17, wherein the compound is administered as part of a pharmaceutical composition.

Embodiment 19 provides the method of any of Embodiments 11-18, further administering to the subject another therapeutic agent that treats, ameliorates, and/or prevents the cancer.

Embodiment 20 provides the method of any of Embodiments 11-19, wherein the subject is a mammal.

Embodiment 21 provides the method of any of Embodiments 11-20, wherein the subject is a human.

Embodiment 22 provides a method of preparing a compound of any of Embodiments 1-9, or a salt, solvate, isotopically labelled derivative, stereoisomer, tautomer, or geometric isomer thereof, wherein the method comprises contacting compound (4)

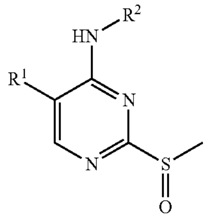

with compound (5)

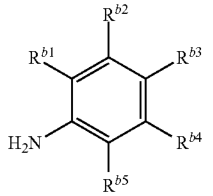

under conditions that allow for forming a compound of formula (I).

Embodiment 23 provides the method of Embodiment 22, wherein (4) is obtained by oxidizing (3)

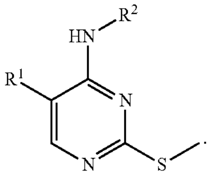

Embodiment 24 provides the method of Embodiment 23, wherein (3) is obtained by contacting (2)

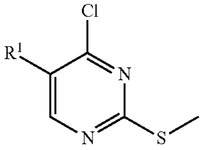

with amine $R^2$—$NH_2$ under conditions that allow for forming (3).

Embodiment 25 provides the method of Embodiment 24, wherein (2) is obtained by reaction (1)

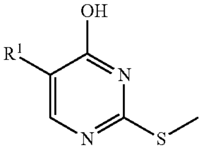

with a chlorinating agent under conditions that allow for forming (2).

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A compound of formula (I), or a salt, solvate, isotopically labelled derivative, stereoisomer, tautomer, or geometric isomer thereof:

(I)

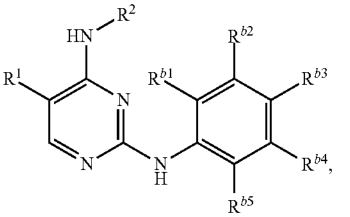

wherein:

$R^1$ is CN;

$R^2$ is selected from the group consisting of:

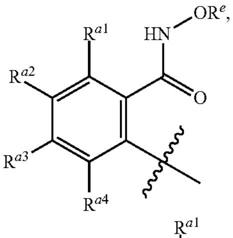

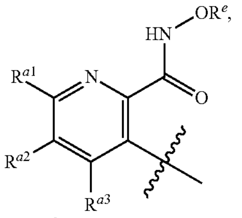

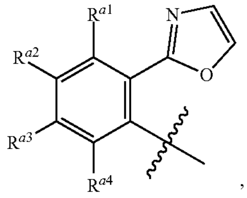

, and

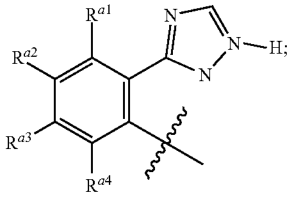

each occurrence of $R^{a1}$, $R^{a2}$, $R^{a3}$, and $R^{a4}$ is independently selected from the group consisting of H, F, Cl, Br, I, $C_1$-$C_6$ alkyl, $C_3$-$C_8$ cycloalkyl, phenyl, $C_1$-$C_6$ hydroxyalkyl, $C_1$-$C_6$ haloalkyl, $C_1$-$C_6$ haloalkoxy, ($C_1$-$C_6$ alkoxy)—$C_0$-$C_6$ alkylene, —$NR^cR^c$, —$OR^c$, —C(═O)$OR^c$, and —C(═O)N($R^c$)($R^c$), wherein each occurrence of $R^e$ is independently H, $C_1$-$C_6$ alkyl, or $C_3$-$C_8$ cycloalkyl, or two $R^c$ bound to the same N atom combine with the N atom to form optionally substituted 3- to 8-membered heterocyclyl;

$R^{b1}$, $R^{b2}$, $R^{b3}$, $R^{b4}$, and $R^{b5}$ are independently selected from the group consisting of H, F, Cl, Br, I, $C_1$-$C_6$ alkyl, $C_3$-$C_8$ cycloalkyl, phenyl, $C_1$-$C_6$ hydroxyalkyl, $C_1$-$C_6$ haloalkyl, $C_1$-$C_6$ haloalkoxy, ($C_1$-$C_6$ alkoxy)-$C_0$-$C_6$ alkylene, —$(CH_2)_{0-3}$—$NR^dR^d$, —$O(CH_2)_{2-3}$—$NR^dR^d$, —$OR^d$, —C(═O)$OR^d$, and —C(═O)N($R^d$)($R^d$), wherein each occurrence of $R^d$ is independently H, $C_1$-$C_6$ alkyl, or $C_3$-$C_8$ cycloalkyl, or two $R^d$ bound to the same N atom combine with the N atom to form optionally substituted 3- to 8-membered heterocyclyl; and each occurrence of $R^e$ is independently $C_1$-$C_6$ alkyl.

2. The compound of claim 1, wherein

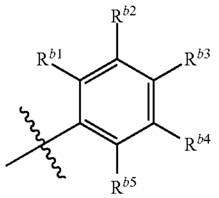

is

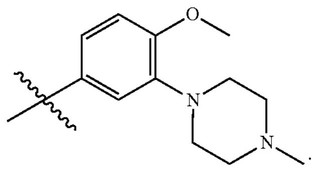

3. A compound selected from the group consisting of:

6c

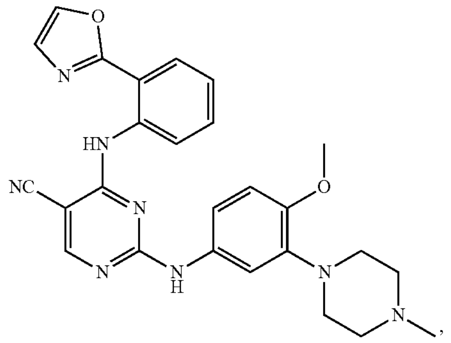

6e

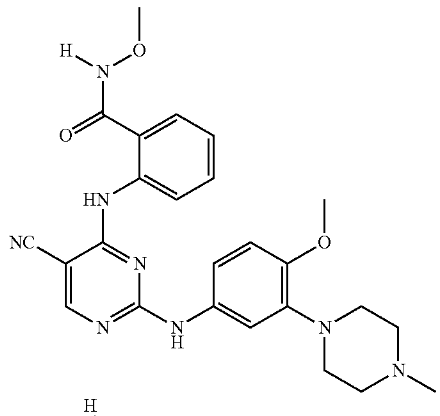

and

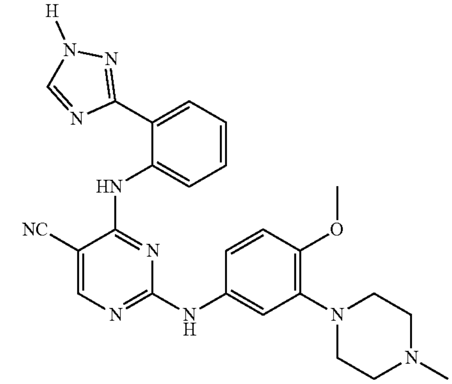

or a salt, solvate, isotopically labelled derivative, or tautomer thereof.

4. A pharmaceutical composition comprising at least one pharmaceutically acceptable excipient and a compound of claim 1.

5. A method of inhibiting SPAK or OSR activity in a subject, the method comprising administering to the subject a therapeutically effective amount of a compound of claim 1.

6. A method of treating or ameliorating cancer in a subject, the method comprising administering to the subject a therapeutically effective amount of a compound of claim 1.

7. A method of treating or ameliorating cancer cell migration or cancer cell invasion in a subject, the method comprising administering to the subject a therapeutically effective amount of a compound of claim 1.

8. A method of reducing or reversing growth or viability of a cancer in a subject, the method comprising administering to the subject a therapeutically effective amount of a compound of claim 1.

9. A method of reducing volume of a cancerous tumor in a subject, the method comprising administering to the subject a therapeutically effective amount of a compound of claim 1.

10. A method of extending survival in a subject afflicted with a cancer, the method comprising administering to the subject a therapeutically effective amount of a compound of claim 1.

11. The method of claim 6, wherein the cancer comprises at least one of melanoma, glioblastoma, pancreatic cancer, thyroid cancer, lung cancer, breast cancer, colorectal cancer, and other invasive and metastatic cancers.

12. The method of claim 6, wherein at least one of the following applies:

(a) the compound is administered as part of a pharmaceutical composition;

(b) the subject is further administered another therapeutic agent that treats or ameliorates the cancer;

(c) the subject is a mammal;

(d) the subject is a human.

13. A method of inhibiting SPAK or OSR activity in a subject, the method comprising administering to the subject a therapeutically effective amount of a compound of claim 3.

14. A method of treating or ameliorating cancer in a subject, the method comprising administering to the subject a therapeutically effective amount of a compound of claim 3.

15. A method of treating or ameliorating cancer cell migration or cancer cell invasion in a subject, the method comprising administering to the subject a therapeutically effective amount of a compound of claim 3.

16. A method of reducing or reversing growth or viability of a cancer in a subject, the method comprising administering to the subject a therapeutically effective amount of a compound of claim 3.

17. A method of reducing volume of a cancerous tumor in a subject, the method comprising administering to the subject a therapeutically effective amount of a compound of claim 3.

18. A method of extending survival in a subject afflicted with a cancer, the method comprising administering to the subject a therapeutically effective amount of a compound of claim 3.

19. The method of claim 14, wherein the cancer comprises at least one of melanoma, glioblastoma, pancreatic cancer, thyroid cancer, lung cancer, breast cancer, colorectal cancer, and other invasive and metastatic cancers.

20. The method of claim 14, wherein at least one of the following applies:

(a) the compound is administered as part of a pharmaceutical composition;

(b) the subject is further administered another therapeutic agent that treats or ameliorates the cancer;

(c) the subject is a mammal;

(d) the subject is a human.

* * * * *

SEQUENCE LISTING

```
<160> NUMBER OF SEQ ID NOS: 35

<210> SEQ ID NO 1
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 1

accgcggccg caaaaaaaat ccttagcttt cg                                 32


<210> SEQ ID NO 2
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 2

aaagcggccg cgcttctttg agcgaac                                       27


<210> SEQ ID NO 3
<211> LENGTH: 18
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: C is acetylated
<220> FEATURE:
<221> NAME/KEY: misc_feature
<222> LOCATION: (14)..(14)
<223> OTHER INFORMATION: Xaa = phosphoserine

<400> SEQUENCE: 3

Cys Gly Leu Ala Thr Leu Lys Arg Ala Ser Phe Ala Lys Xaa Val Ile
1               5                   10                  15

Gly Cys
```

-continued

```
<210> SEQ ID NO 4
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(7)
<223> OTHER INFORMATION: 8 of 9 Xaa in positions 3-7 and 9-12 are
      degenerate mixtures of all 20 amino acids except serine,
      threonine, and cysteine.  The other Xaa position is fixed as one
      of the 20 standard amino acids, phosphothreonine, or
      phosphotyrosine.
<220> FEATURE:
<221> NAME/KEY: misc_feature
<222> LOCATION: (8)..(8)
<223> OTHER INFORMATION: Xaa = serine or threonine
<220> FEATURE:
<221> NAME/KEY: misc_feature
<222> LOCATION: (9)..(12)
<223> OTHER INFORMATION: 8 of the 9 Xaa in positions 3-7 and 9-12 are
      degenerate mixtures of all 20 amino acids except serine,
      threonine, and cysteine. The other Xaa position is fixed as one of
      the 20 standard amino acids, phosphothreonine, or phosphotyrosine.
<220> FEATURE:
<221> NAME/KEY: misc_feature
<222> LOCATION: (16)..(16)
<223> OTHER INFORMATION: Lysine is substituted with biotin

<400> SEQUENCE: 4

Tyr Ala Xaa Xaa Xaa Xaa Xaa Xaa Xaa Xaa Xaa Xaa Gly Ala Lys Lys
1               5                   10                  15


<210> SEQ ID NO 5
<211> LENGTH: 24
<212> TYPE: RNA
<213> ORGANISM: Artificial Sequence
<220> FEATURE:
<223> OTHER INFORMATION: Chemically Synthesized

<400> SEQUENCE: 5

cacaauguau agaucacgac ggca                                            24


<210> SEQ ID NO 6
<211> LENGTH: 10
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(3)
<223> OTHER INFORMATION: Xaa = phosphoserine
<220> FEATURE:
<221> NAME/KEY: misc_feature
<222> LOCATION: (7)..(7)
<223> OTHER INFORMATION: Xaa = phosphoserine

<400> SEQUENCE: 6

Arg Ala Xaa Phe Ala Lys Xaa Val Ile Gly
1               5                   10


<210> SEQ ID NO 7
<211> LENGTH: 5
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(3)
<223> OTHER INFORMATION: Xaa = phosphothreonine
```

<400> SEQUENCE: 7

Arg Lys Xaa Phe Val
1 5

<210> SEQ ID NO 8
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 8

Leu Tyr Met Arg Thr Phe
1 5

<210> SEQ ID NO 9
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 9

Gly Tyr Asn Thr Ile Asp Val
1 5

<210> SEQ ID NO 10
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 10

Phe Cys Met Arg Thr Phe
1 5

<210> SEQ ID NO 11
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 11

Tyr Tyr Leu Arg Thr Phe
1 5

<210> SEQ ID NO 12
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 12

Gly His Asn Thr Met Asp Ala
1 5

<210> SEQ ID NO 13
<211> LENGTH: 6
<212> TYPE: PRT
<213> ORGANISM: Artificial Sequence
<220> FEATURE:
<223> OTHER INFORMATION: Chemically Synthesized -continued

<400> SEQUENCE: 13

Tyr Tyr Leu Gln Thr Phe
1 5

<210> SEQ ID NO 14
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 14

Thr Tyr Glu Arg Thr Leu
1 5

<210> SEQ ID NO 15
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 15

Val His Met Thr Trp Thr Lys
1 5

<210> SEQ ID NO 16
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 16

Thr Tyr Glu Lys Thr Leu
1 5

<210> SEQ ID NO 17
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 17

Ile Gln Met Thr Trp Thr Arg
1 5

<210> SEQ ID NO 18
<211> LENGTH: 21
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(4)
<223> OTHER INFORMATION: Xaa = phosphothreonine

<400> SEQUENCE: 18

Val Arg Lys Xaa Phe Val Gly Thr Pro Cys Trp Met Ala Pro Glu Val
1 5 10 15

Met Glu Gln Val Arg
20

<210> SEQ ID NO 19

-continued

<211> LENGTH: 19
<212> TYPE: PRT
<213> ORGANISM: Artificial Sequence
<220> FEATURE:
<223> OTHER INFORMATION: Chemically Synthesized

<400> SEQUENCE: 19

Lys Thr Phe Val Gly Thr Pro Cys Trp Met Ala Pro Glu Val Met Glu
1 5 10 15

Gln Val Arg

<210> SEQ ID NO 20
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 20

Asn Gly Val Leu Glu Glu Ala Ile Ile Ala Thr Ile Leu Lys
1 5 10

<210> SEQ ID NO 21
<211> LENGTH: 11
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (6)..(6)
<223> OTHER INFORMATION: Xaa = phosphoserine

<400> SEQUENCE: 21

Arg Val Pro Gly Ser Xaa Gly His Leu His Lys
1 5 10

<210> SEQ ID NO 22
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 22

Arg Val Pro Gly Ser Ser Gly His Leu His Lys
1 5 10

<210> SEQ ID NO 23
<211> LENGTH: 22
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (21)..(21)
<223> OTHER INFORMATION: Xaa = phosphothreonine
<220> FEATURE:
<221> NAME/KEY: misc_feature
<222> LOCATION: (22)..(22)
<223> OTHER INFORMATION: Xaa = phosphotyrosine

<400> SEQUENCE: 23

Pro Gly Ala Cys Ser Thr Val Ile Leu Met Phe Tyr Trp His Lys Arg
1 5 10 15

Gln Asn Asp Glu Xaa Xaa
20

<210> SEQ ID NO 24
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 24
accccagagt tcatggcccc 20

<210> SEQ ID NO 25
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 25
ccgctcgagt tatgtttcct cttggaagaa gg 32

<210> SEQ ID NO 26
<211> LENGTH: 36
<212> TYPE: DNA
<213> ORGANISM: Artificial Sequence
<220> FEATURE:
<223> OTHER INFORMATION: Chemically Synthesized

<400> SEQUENCE: 26
gggcttcttt tgccaagtag gtgataggta ccccag 36

<210> SEQ ID NO 27
<211> LENGTH: 36
<212> TYPE: DNA
<213> ORGANISM: Artificial Sequence
<220> FEATURE:
<223> OTHER INFORMATION: Chemically Synthesized

<400> SEQUENCE: 27
ctggggtacc tatcacctac ttggcaaaag aagccc 36

<210> SEQ ID NO 28
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 28
cctgaagcgg gcttagtttg ccaagtaggt g 31

<210> SEQ ID NO 29
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 29
cacctacttg gcaaactaag cccgcttcag g 31

<210> SEQ ID NO 30
<211> LENGTH: 33
<212> TYPE: DNA
<213> ORGANISM: Artificial Sequence
<220> FEATURE:

<223> OTHER INFORMATION: Chemically Synthesized

<400> SEQUENCE: 30
cgggcttctt ttgccaagga tgtgataggt acc 33

<210> SEQ ID NO 31
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 31
ggtacctatc acatccttgg caaaagaagc ccg 33

<210> SEQ ID NO 32
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 32
ccctgaagcg ggctgatttt gccaagagtg 30

<210> SEQ ID NO 33
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 33
cactcttggc aaaatcagcc cgcttcaggg 30

<210> SEQ ID NO 34
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 34
cgggctgatt ttgccaagga tgtgataggt acc 33

<210> SEQ ID NO 35
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 35
ggtacctatc acatccttgg caaaatcagc ccg 33